(12) United States Patent
Bolt et al.

(10) Patent No.: US 9,150,848 B2
(45) Date of Patent: *Oct. 6, 2015

(54) CONJUGATED FACTOR VIII MOLECULES

(71) Applicant: Novo Nordisk A/S, Bagsvaerd (DK)

(72) Inventors: Gert Bolt, Vaerloese (DK); Brian Berg Stidsen Vandahl, Kastrup (DK); Lars Thim, Gentofte (DK); Henning Ralf Stennicke, Kokkedal (DK); Thomas Dock Steenstrup, Gentofte (DK); Shawn DeFrees, North Wales, PA (US)

(73) Assignee: Novo Nordisk A/s, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/272,726

(22) Filed: May 8, 2014

(65) Prior Publication Data

US 2014/0242057 A1 Aug. 28, 2014

Related U.S. Application Data

(63) Continuation of application No. 12/597,473, filed as application No. PCT/US2009/035339 on Feb. 26, 2009, now abandoned.

(60) Provisional application No. 61/032,006, filed on Feb. 27, 2008.

(51) Int. Cl.
| | |
|---|---|
| C12N 9/96 | (2006.01) |
| A61K 47/26 | (2006.01) |
| A61K 38/37 | (2006.01) |
| C07K 14/755 | (2006.01) |

(52) U.S. Cl.
CPC . *C12N 9/96* (2013.01); *A61K 38/37* (2013.01); *A61K 47/26* (2013.01); *C07K 14/755* (2013.01)

(58) Field of Classification Search
None
See application file for complete search history.

(56) References Cited

U.S. PATENT DOCUMENTS

| | | | |
|---|---|---|---|
| 4,055,635 A | 10/1977 | Green et al. | |
| 4,088,538 A | 5/1978 | Schneider | |
| 4,179,337 A | 12/1979 | Davis et al. | |
| 4,385,260 A | 5/1983 | Watts | |
| 4,412,989 A | 11/1983 | Iwashita et al. | |
| 4,414,147 A | 11/1983 | Klibanov et al. | |
| 4,438,253 A | 3/1984 | Casey et al. | |
| 4,451,566 A | 5/1984 | Spencer | |
| 4,496,689 A | 1/1985 | Mitra | |
| 4,565,653 A | 1/1986 | Ives et al. | |
| 4,675,414 A | 6/1987 | DeFusco et al. | |
| 4,704,361 A | 11/1987 | Miccoli et al. | |
| 4,767,702 A | 8/1988 | Cohenford | |
| 4,806,595 A | 2/1989 | Noishiki et al. | |
| 4,826,945 A | 5/1989 | Cohn et al. | |
| 4,847,325 A | 7/1989 | Shadle et al. | |
| 4,879,236 A | 11/1989 | Smith et al. | |
| 4,918,009 A | 4/1990 | Nilsson | |
| 4,925,796 A | 5/1990 | Bergh et al. | |
| 4,970,300 A | 11/1990 | Fulton et al. | |
| 4,980,502 A | 12/1990 | Felder et al. | |
| 5,032,519 A | 7/1991 | Paulson et al. | |
| 5,047,335 A | 9/1991 | Paulson et al. | |
| 5,104,651 A | 4/1992 | Boone et al. | |
| 5,122,614 A | 6/1992 | Zalipsky | |
| 5,147,788 A | 9/1992 | Page et al. | |
| 5,153,265 A | 10/1992 | Shadle et al. | |
| 5,154,924 A | 10/1992 | Friden | |
| 5,164,374 A | 11/1992 | Rademacher et al. | |
| 5,166,322 A | 11/1992 | Shaw et al. | |
| 5,169,933 A | 12/1992 | Anderson et al. | |
| 5,180,674 A | 1/1993 | Roth | |
| 5,182,107 A | 1/1993 | Friden | |
| 5,194,376 A | 3/1993 | Kang | |
| 5,202,413 A | 4/1993 | Spinu | |
| 5,206,344 A | 4/1993 | Katre et al. | |
| 5,219,564 A | 6/1993 | Zalipsky et al. | |
| 5,272,066 A | 12/1993 | Bergh et al. | |
| 5,278,299 A | 1/1994 | Wong et al. | |
| 5,281,698 A | 1/1994 | Nitecki | |
| 5,288,637 A | 2/1994 | Roth | |
| 5,298,643 A | 3/1994 | Greenwald | |
| 5,308,460 A | 5/1994 | Mazid et al. | |
| 5,324,663 A | 6/1994 | Lowe | |
| 5,324,844 A | 6/1994 | Zalipsky | |
| 5,342,940 A | 8/1994 | Ono et al. | |
| 5,346,696 A | 9/1994 | Kim et al. | |
| 5,352,670 A | 10/1994 | Venot et al. | |
| 5,369,017 A | 11/1994 | Wong et al. | |

(Continued)

FOREIGN PATENT DOCUMENTS

| | | |
|---|---|---|
| AU | 1991083760 | 10/1991 |
| AU | 1992017052 | 5/1992 |

(Continued)

OTHER PUBLICATIONS

Lenting, The Life Cycle of Coagulation Factor VIII in View of Its Structure and Function, Blood, vol. 92, No. 11 (1998).*
Shearwater Corporation Catalog 2001 Polyethylene Glycol and Derivatives for Biomedical Applications, 2001.*
Veronese & Pasut, PEGylation, successful approach to drug delivery, DDT, vol. 10, No. 21, Nov. 2005.*
Saenko, Strategies towards a longer acting factor VIII, Haemophilia, 2006, 12, (Suppl. 3), 42-51.*
DeFrees et al., GlycoPEGylation of recombinant therapeutic proteins produced in *Escherichia coli*, Glycobiology, vol. 16, No. 9, pp. 833-843 (2006).*
Philip J. Fay, Activation of factor VIII and mechanisms of cofactor action, Blood Reviews (2004) 18, 1-15.*
Karin Julenius et al., Glycobiology, "Prediction, Conservation Analysis, and Structural Characterization of Mammalian Mucin-Type O-Glycosylation Sites", 2004, vol. 15, No. 2, pp. 153-164.

(Continued)

*Primary Examiner* — Karlheinz R Skowronek
*Assistant Examiner* — Joseph Fischer
(74) *Attorney, Agent, or Firm* — Nonna G. Akopyan

(57) ABSTRACT

The present invention relates to B-domain truncated Factor VIII molecules with a modified circulatory half life, said molecule being covalently conjugated with a hydrophilic polymer. The invention furthermore relates to methods for obtaining such molecules as well as use of such molecules.

12 Claims, 9 Drawing Sheets

(56) References Cited

U.S. PATENT DOCUMENTS

| | | |
|---|---|---|
| 5,374,541 A | 12/1994 | Wong et al. |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer et al. |
| 5,409,817 A | 4/1995 | Ito et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | Defrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,645,860 B2 | 1/2010 | Turecek et al. |
| 7,662,933 B2 | 2/2010 | Kinstler et al. |
| 7,683,158 B2 | 3/2010 | Siekmann et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | Defrees et al. |
| 8,008,252 B2 | 8/2011 | DeFrees et al. |
| 8,063,015 B2 | 11/2011 | DeFrees et al. |
| 8,178,108 B2 | 5/2012 | Buechler et al. |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 | 1/2013 | DeFrees et al. |
| 8,716,239 B2 | 5/2014 | DeFrees et al. |
| 8,716,240 B2 | 5/2014 | DeFrees et al. |
| 8,791,066 B2 | 7/2014 | DeFrees |
| 8,791,070 B2 | 7/2014 | DeFrees et al. |
| 8,841,439 B2 | 9/2014 | Felo et al. |
| 8,911,967 B2 | 12/2014 | DeFrees et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |

(56) References Cited

U.S. PATENT DOCUMENTS

| | | |
|---|---|---|
| 2002/0115833 A1 | 8/2002 | Burg et al. |
| 2002/0137134 A1 | 9/2002 | Gerngross |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0151168 A1 | 8/2004 | Phillips et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0032742 A1 | 2/2005 | DeFrees et al. |
| 2005/0064540 A1 | 3/2005 | Defrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0115876 A1 | 6/2006 | Pan et al. |
| 2006/0165728 A1 | 7/2006 | Young et al. |
| 2006/0177892 A1 | 8/2006 | De Frees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 * | 3/2008 | DeFrees et al. .............. 435/68.1 |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | Defrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | Defrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | Defrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | Defrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |

(56) References Cited

U.S. PATENT DOCUMENTS

| | | |
|---|---|---|
| 2012/0093840 A1 | 4/2012 | Ostergaard et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2014/0294762 A1 | 10/2014 | DeFrees et al. |

FOREIGN PATENT DOCUMENTS

| | | | |
|---|---|---|---|
| CA | 2131703 A1 | 9/1993 | |
| CA | 2110543 A1 | 6/1994 | |
| CA | 2167521 A1 | 2/1995 | |
| CA | 2324616 A1 | 9/1999 | |
| CA | 2500389 A1 | 4/2004 | |
| CA | 2511814 A1 | 7/2004 | |
| DE | 2437388 A1 | 2/1975 | |
| DE | 19709787 A1 | 9/1998 | |
| DE | 19852729 A1 | 5/2000 | |
| EP | 0119539 A2 | 9/1984 | |
| EP | 200421 A2 | 11/1986 | |
| EP | 0370205 A2 | 5/1990 | |
| EP | 0459630 A2 | 12/1991 | |
| EP | 474313 A2 | 3/1992 | |
| EP | 0475354 A2 | 3/1992 | |
| EP | 0577580 A2 | 1/1994 | |
| EP | 585109 A2 | 3/1994 | |
| EP | 605963 A2 | 7/1994 | |
| EP | 775711 A1 | 5/1997 | |
| EP | 863154 A1 | 9/1998 | |
| EP | 1258497 A2 | 11/2002 | |
| EP | 1260582 A1 | 11/2002 | |
| EP | 1270642 A1 | 1/2003 | |
| EP | 1428878 A1 | 6/2004 | |
| EP | 1481985 A1 | 12/2004 | |
| FI | 922515 A | 12/1992 | |
| GB | 2256197 A | 12/1992 | |
| JP | 59-172425 A | 9/1984 | |
| JP | H02-076894 | 3/1990 | |
| JP | 03-503759 T | 8/1991 | |
| JP | H06-160365 A | 6/1994 | |
| JP | H07-196925 A | 8/1995 | |
| JP | H07-223921 A | 8/1995 | |
| JP | H08-506023 A | 7/1996 | |
| JP | 9503905 T | 4/1997 | |
| JP | H09-208461 A | 8/1997 | |
| JP | 10-307356 A | 11/1998 | |
| JP | 2000-501607 A | 2/2000 | |
| JP | 2001-508783 T | 7/2001 | |
| JP | 2001-519784 | 10/2001 | |
| JP | 2003-521930 A | 7/2003 | |
| JP | 2005-521635 A | 7/2005 | |
| JP | 2005-328782 A | 12/2005 | |
| KR | 2002-0010363 A | 2/2002 | |
| KR | 10-0396983 B1 | 9/2003 | |
| NZ | 532027 A | 9/2008 | |
| NZ | 539415 A | 12/2008 | |
| NZ | 547554 A | 9/2009 | |
| RU | 2005/101348 A | 8/2005 | |
| SE | 9501285 A | 10/1996 | |
| WO | 87/00056 A1 | 1/1987 | |
| WO | 87/05330 A1 | 9/1987 | |
| WO | 89/06546 | 7/1989 | |
| WO | 89/10134 A1 | 11/1989 | |
| WO | 90/07572 A1 | 7/1990 | |
| WO | 90/08164 A1 | 7/1990 | |
| WO | 90/08823 A1 | 8/1990 | |
| WO | 90/12090 A1 | 10/1990 | |
| WO | 90/13540 A1 | 11/1990 | |
| WO | 91/06635 A1 | 5/1991 | |
| WO | 91/09122 A1 | 6/1991 | |
| WO | 91/14697 A1 | 10/1991 | |
| WO | 92/01055 A1 | 1/1992 | |
| WO | 92/15686 A1 | 9/1992 | |
| WO | 92/16555 A1 | 10/1992 | |
| WO | 92/16640 A1 | 10/1992 | |
| WO | 92/18135 A1 | 10/1992 | |
| WO | 92/22310 A1 | 12/1992 | |
| WO | 93/08842 A1 | 5/1993 | |
| WO | 93/13198 A1 | 7/1993 | |
| WO | 93/15189 A1 | 8/1993 | |
| WO | 93/18787 A1 | 9/1993 | |
| WO | 94/04193 A1 | 3/1994 | |
| WO | 94/05332 A2 | 3/1994 | |
| WO | 94/09027 A1 | 4/1994 | |
| WO | 94/15625 A1 | 7/1994 | |
| WO | 94/17039 A1 | 8/1994 | |
| WO | 94/18247 A1 | 8/1994 | |
| WO | 94/25614 A1 | 11/1994 | |
| WO | 94/25615 A1 | 11/1994 | |
| WO | 94/26760 A1 | 11/1994 | |
| WO | 94/27631 A1 | 12/1994 | |
| WO | 94/28024 A1 | 12/1994 | |
| WO | 95/02421 A1 | 1/1995 | |
| WO | 95/04278 A1 | 2/1995 | |
| WO | 95/05465 A1 | 2/1995 | |
| WO | WO/95/26750 * | 10/1995 | ............. A61K 38/37 |
| WO | 96/10089 A1 | 4/1996 | |
| WO | 96/11953 A1 | 4/1996 | |
| WO | 96/12800 A1 | 5/1996 | |
| WO | 96/21468 A2 | 7/1996 | |
| WO | 96/21469 A1 | 7/1996 | |
| WO | 96/32491 A1 | 10/1996 | |
| WO | 96/32492 A1 | 10/1996 | |
| WO | 96/34015 A1 | 10/1996 | |
| WO | 96/36357 A1 | 11/1996 | |
| WO | 96/40731 A1 | 12/1996 | |
| WO | 96/40881 A1 | 12/1996 | |
| WO | 97/05330 A1 | 2/1997 | |
| WO | 97/11957 A1 | 4/1997 | |
| WO | 97/21822 A2 | 6/1997 | |
| WO | 97/47651 A1 | 12/1997 | |
| WO | 98/05363 A2 | 2/1998 | |
| WO | 98/31826 A1 | 7/1998 | |
| WO | 98/32466 A1 | 7/1998 | |
| WO | 98/41562 A1 | 9/1998 | |
| WO | 98/51784 A1 | 11/1998 | |
| WO | 98/58964 A1 | 12/1998 | |
| WO | 99/00150 A2 | 1/1999 | |
| WO | 99/13063 A1 | 3/1999 | |
| WO | 99/14259 A1 | 3/1999 | |
| WO | 99/22764 A1 | 5/1999 | |
| WO | 99/28491 A1 | 6/1999 | |
| WO | 99/34833 A1 | 7/1999 | |
| WO | 99/37779 A1 | 7/1999 | |
| WO | 99/45964 A1 | 9/1999 | |
| WO | 99/48515 A1 | 9/1999 | |
| WO | 99/54342 A1 | 10/1999 | |
| WO | 99/55376 A1 | 11/1999 | |
| WO | 00/23114 A2 | 4/2000 | |
| WO | 00/26354 A1 | 5/2000 | |
| WO | 00/29558 A1 | 5/2000 | |
| WO | 00/29603 A2 | 5/2000 | |
| WO | 00/44785 A1 | 8/2000 | |
| WO | 00/46379 A1 | 8/2000 | |
| WO | 00/65087 A1 | 11/2000 | |
| WO | 01/02017 A1 | 1/2001 | |
| WO | 01/05434 A2 | 1/2001 | |
| WO | 01/19955 A2 | 3/2001 | |
| WO | 01/39788 A2 | 6/2001 | |
| WO | 01/49830 A2 | 7/2001 | |
| WO | 01/51510 A2 | 7/2001 | |
| WO | 01/58493 A1 | 8/2001 | |
| WO | 01/58935 A2 | 8/2001 | |
| WO | 01/60411 A1 | 8/2001 | |
| WO | 01/76640 A2 | 10/2001 | |
| WO | 01/83725 A1 | 11/2001 | |
| WO | 01/87329 A1 | 11/2001 | |
| WO | 01/87925 A2 | 11/2001 | |
| WO | 01/88117 A2 | 11/2001 | |
| WO | 02/02597 A2 | 1/2002 | |
| WO | 02/02764 A2 | 1/2002 | |
| WO | 02/13843 A2 | 2/2002 | |
| WO | 02/13873 A2 | 2/2002 | |

(56) References Cited

FOREIGN PATENT DOCUMENTS

| | | | |
|---|---|---|---|
| WO | 02/29025 A2 | 4/2002 | |
| WO | 02/44196 A1 | 6/2002 | |
| WO | 02/49673 A2 | 6/2002 | |
| WO | 02/50099 A2 | 6/2002 | |
| WO | 02/053580 A2 | 7/2002 | |
| WO | 02/074806 A2 | 9/2002 | |
| WO | 02/077218 A1 | 10/2002 | |
| WO | 02/092619 A2 | 11/2002 | |
| WO | 03/006501 A2 | 1/2003 | |
| WO | 03/011879 A1 | 2/2003 | |
| WO | 03/017949 A2 | 3/2003 | |
| WO | 03/029291 A2 | 4/2003 | |
| WO | 03/031464 A2 | 4/2003 | |
| WO | 03/045980 A2 | 6/2003 | |
| WO | 03/046150 | 6/2003 | |
| WO | 03/093448 | 11/2003 | |
| WO | 2004/000366 A1 | 12/2003 | |
| WO | 2004/009838 | 1/2004 | |
| WO | 2004/010327 A2 | 1/2004 | |
| WO | 2004/014417 A2 | 2/2004 | |
| WO | 2004/022004 | 3/2004 | |
| WO | 2004/029090 | 4/2004 | |
| WO | 2004/029091 A2 | 4/2004 | |
| WO | 2004/033651 A2 | 4/2004 | |
| WO | 2004/046222 | 6/2004 | |
| WO | 2004/047858 A1 | 6/2004 | |
| WO | 2004/67566 A1 | 8/2004 | |
| WO | 2004/075923 A2 | 9/2004 | |
| WO | 2004/083258 A2 | 9/2004 | |
| WO | 2004/083259 | 9/2004 | |
| WO | 2004/091499 A2 | 10/2004 | |
| WO | 2004/093823 A2 | 11/2004 | |
| WO | 2004/096148 A2 | 11/2004 | |
| WO | 2004/099231 A2 | 11/2004 | |
| WO | 2004/101597 A2 | 11/2004 | |
| WO | 2004/101740 A2 | 11/2004 | |
| WO | 2004/103275 A2 | 12/2004 | |
| WO | 2004/106373 A1 | 12/2004 | |
| WO | 2005/001025 A2 | 1/2005 | |
| WO | 2005/003171 A2 | 1/2005 | |
| WO | 2005/012484 | 2/2005 | |
| WO | 2005/014024 A2 | 2/2005 | |
| WO | 2005/014035 A2 | 2/2005 | |
| WO | 2005/025606 A1 | 3/2005 | |
| WO | 2005/051327 | 6/2005 | |
| WO | 2005/055946 | 6/2005 | |
| WO | 2005/055950 A2 | 6/2005 | |
| WO | 2005/56760 A2 | 6/2005 | |
| WO | 2005/067601 A2 | 7/2005 | |
| WO | 2005/070138 A2 | 8/2005 | |
| WO | 2005/072371 | 8/2005 | |
| WO | 2005/079363 A2 | 9/2005 | |
| WO | 2005/091944 | 10/2005 | |
| WO | 2005/121331 A2 | 12/2005 | |
| WO | 2006/005058 A2 | 1/2006 | |
| WO | 2006/010143 | 1/2006 | |
| WO | 2006/011839 A1 | 2/2006 | |
| WO | 2006/013202 A2 | 2/2006 | |
| WO | 2006/014349 A2 | 2/2006 | |
| WO | 2006/014466 A2 | 2/2006 | |
| WO | 2006/018204 A1 | 2/2006 | |
| WO | 2006/020372 A2 | 2/2006 | |
| WO | 2006/031811 A2 | 3/2006 | |
| WO | 2006/035057 A1 | 4/2006 | |
| WO | 2006/050247 | 5/2006 | |
| WO | 2006/053299 A2 | 5/2006 | |
| WO | 2006/074279 A1 | 7/2006 | |
| WO | 2006/074467 | 7/2006 | |
| WO | 2006/078645 A2 | 7/2006 | |
| WO | 2006/082517 A1 | 8/2006 | |
| WO | 2006/103298 A2 | 10/2006 | |
| WO | 2006/105426 | 10/2006 | |
| WO | WO/2006/103298 | * 10/2006 | ........... C07K 14/755 |
| WO | 2006/119987 A2 | 11/2006 | |
| WO | 2006/121569 | 11/2006 | |
| WO | 2006/121791 | 11/2006 | |
| WO | 2006/127910 | 11/2006 | |
| WO | 2006/134173 A2 | 12/2006 | |
| WO | 2007/022512 | 2/2007 | |
| WO | 2007/031559 A2 | 3/2007 | |
| WO | 2007/056191 | 5/2007 | |
| WO | 2007/126808 A1 | 11/2007 | |
| WO | 2007/135182 A2 | 11/2007 | |
| WO | 2008/011633 A2 | 1/2008 | |
| WO | WO/2008/011633 | * 1/2008 | ........... A61K 38/16 |
| WO | 2008/025856 A2 | 3/2008 | |
| WO | 2008/057683 | 5/2008 | |
| WO | 2008/60780 A2 | 5/2008 | |
| WO | 2008/073620 | 6/2008 | |
| WO | 2008/124406 | 10/2008 | |
| WO | 2008/151258 | 12/2008 | |
| WO | 2008/154639 | 12/2008 | |
| WO | 2009/089396 | 7/2009 | |

OTHER PUBLICATIONS

P. J. Lenting et al., Haemophilia, "Factor VIII and Von Willebrand Factor—Too Sweet for Their Own Good", 2010, vol. 16, No. 5, pp. 194-199.
Saenko, E. L. et al., Haemophilia, "Strategies Towards a Longer Acting Factor VIII", 2006, vol. 12, No. 3, pp. 42-51.
Anne Jessica Fulton, New York University, "Chemical Modification of Human FVIII by Covalent Linkage of Carbohydrate: Preparetion of a Potential Therapeutic Agent for the Treatment of Hemophilia", 1998, Volume -, Number -, pp. 156.
Fischer et al, PLOS One, "Models for Prediction of Factor VIII Half-Life in Severe Haemophiliacs: Distinct Approaches for Blood Group O and Non-O Patients", 2009, vol. 4, No. 8, pp. e6745.
Hironaka et al, The Journal of Biological Chemistry, "Comparative Studyo F the Sugar Chainosf Factor VI11 Purified From Human Plasma and From the Culture MOEFD RIAE Combinant Baby Hamster Kidney Cells", 1992, vol. 267, No. 12, pp. 8012-8020.
Lairson et al, Annual Review of Biochemistry, "Glycosyltransferases: Structures, Functions, and Mechanisms", 2008, vol. 77, Number , pp. 521-555.
Lenting et al, Blood, "The Life Cycle of Coagulation Factor VIII in View of Its Structure and Function", 1998, vol. 92, Number , pp. 3983-3996.
Mazsaroff et al, Analytical Chemistry, "Quantitative Comparison of Global Carbohydrate Structures of Glycoproteins Using LC-MS and In-Source Fragmentation", 1997, vol. 69, Number , pp. 2517-2524.
Medzihradszky et al, Analytical Chemistry, "Structural Characterization of Site-Specific N-Glycosylation of Recombinant Human Factor VIII by Reversed-Phase High-Performance Liquid Chromatography-Spectrometry Electrospray Ionization Mass", 1997, vol. 69, Number , pp. 3986-3994.
Roberts, M.J et al., Advanced Drug Delivery Reviews, "Chemistry for Peptide and Protein Pegylation", 2002, vol. 54, Number -, pp. 459-476.
Randal J. Kaufman, Thrombosis and Haemostasis, "Post-Translational Modifications Required for Coagulation Factor Secretion and Function", 1998, vol. 79, Number , pp. 1068-1079.
Rostin et al, Bioconjugate Chemistry, "B-Domain Deleted Recombinant Coagulation Factor VIII Modified With Monomethoxy Polyethylene Glycol", 2000, vol. 11, Number , pp. 387-396.
Thim L, et al., Haemophilia, "Purification and Characterization of a New Recombinant Factor VIII(N8)", 2010, vol. 16, No. 2, pp. 349-359.
Vehar, G.A., et al., Nature, "Structure of Human Factor VIII", 1984, vol. 312, Number , pp. 337-342.
Betty W et al. Blood. "The Tertiary Structure and Domain Organization of Coagulation Factor VII." 2008. vol. 111(3). pp. 1240-1247.
DeFrees S et al. Glycobiology. "Glycopegylation of Recombinant Therapeutic Proteins Produced in *Escherichia coli*." 2006. vol. 16(9). pp. 833-843.
Larinova N I et al. "Use of Immobilized Physiologically Active Compounds of Protein Nature in the Medicine, M." Published in MSU V. In Teaching Manual Introduction in Applied Enzomology. 1982. pp. 284-305.

(56) References Cited

OTHER PUBLICATIONS

Veronese F M et al. Drug Discovery Today. "Pegylation Successful Approach to Drug Delivery." 2005. vol. 10(21). pp. 1451-1458.
Shearwater Corporation. Catalog 2001, Polythylene Glycol and Derivatives for Biomedical Applications, 2001.
Treetharnmathurot B.et al.,Effect of PEG molecular weight and linking chemistry on the biological activity and thermal stability of PEGylated trypsin, Journal:International Journal of Pharmaceutics, Year 2008, vol. 357, pp. 252-259.
Kisselev, "Polypeptide Release Factors in Prokaryotes and Eukaryotes: Same Function, Different Structure" 2002, Structure 10(1):8-9.
Heimgartner et al Reversible and irreversible cross-linkin of immunoglobin heavychains through their carbohydrate residues. Biochem J (1990) vol. 267. p. 585-591.
Japanese Biochemical Society, New Biochemical Experiment Course 3, Saccharides I, glycoprotein (Top), Tokyo Kagaky Dojin, May 21, 1990, First Edition p. 340.
Luo et al. "Sponaneous calcification of arteries and cartilage in mice lacking matrix GLA protein" Nature 386: 78-81 (1997).
Manfioletti et al. "The Protein Encoded by a Growth Arrest-Specific Gene (gas6) Is a New Member of the Vitamin K-Dependent Proteins Related to Protein S, a Negative Coregulator in the Blood Coagulation Cascade" Mol. Cell. Biol. 13: 4976-4985 (1993).
N-acetylhucosaminetransferase from, http://www.online-medical-dictionary.org/n-acetylglucosaminyltransferases.asp?q=N-acetylglucosaminyltransferases, p. 1-2. Accessed Apr. 14, 2009.
Nelsestuen, "Vitamin K-Dependent Proteins" Vitam. Norm. vol. 58: 355-389 (2000).
Raju et al. "Glycoengineering of Therapeutic Glycoproteins: In Vitro Galactosylation and Sialylation of Glycoproteins with Terminal N-Acetylglucosamine and Galactose Residues" Biochemistry. Jul. 2001 vol. 40 No. 30. p. 8868-8878.
Sorensen et al. "Incorporation of an Active Site Inhibitor in Factor VIIa Alters the Affinity for Tissue Factor" J. Biol. Chem. 1997 272: 11863-11868.
Tsuboi et al. "6*-Sulfo Sialyl Lex but Not 6-Sulfo Sialyl Lex Expressed on the Cell Surface Supports L-selectin-mediated Adhesion" J Biol Chem. vol. 271(44) 1996 p. 27213-27216.
Gilbert at al. "The Synthesis of Sialylated Oligosaccharides Using a CMP-Neu5Ac Synthetase/Sialyltransferase Fusion," Nature Biotechnology, 16: 769-772 (1998).
Koeller et al. "Complex Carbohydrate Synthesis Tools for Glycobiologists: Enzyme-Based Approach and Programmable One-Pot Strategies," Glycobiology, 10(11): 1157-1169 (2000).
Monfardini et al. "A Branched Monomethoxypoly (ethylene glycol) for Protein Modification," Bioconjug. Chem. 6(1): 62-69 (1995).
Tsuji, "Molecular Cloning and Functional Analysis of Sialytransferases," J. Biochemistry, 120: 1-13 (1996).
Corfield A. P., Analysis of Sugar Sequences in Glycoproteins by Glycosidase Digestion and and Gel Filtration, Methods in Molecular Biology, 1993, vol. 19, 269-286.
Breton et al., "Structure/function studies of glycosyltransferases" 1999, Curr. Opin. Struct. Biol. 9(5):563-571.
Breton et al., "Structural and functional features of glycosyltransferases" 2001, Biochimie 83(8):713-718.
Brinkman-Van der Linden et al., "A Missense Mutation in the FUT6 Gene Results in Total Absence of a3-Fucosylation of Human a1-Acid Glycoprotein" 1996, J. Biol. Chem. 271(24):14492-14495.
Biemann et al., "Characterization by Tandem Mass Spectrometry of Structural Modifications in Proteins" 1987, Science 237(4818):992-998.
Binder et al., "Galactosylation by Use of p=Galactosidase: Chemo-Enzymatic Syntheses of Di- and Trisaccharides" 1994, Tetrahedron 50(35):10407-10418.
Apicella et al., "Phenotypic variation in epitope expression of the *Neisseria gonorrhoeae* lipooligosaccharide." 1987, Infect. Immun. 55(8):1755-1761.
Kerwood et al., "Structural Analysis of Lipooligosaccharide Produced by *Neisseria gonorrhoeae*, Strain MS 1 1 mk (Variant A): A Precursor for a Gonococcal Lipooligosaccharide Associated with Virulence" 1992, Biochemistry 31 (51):12760-12768.
NCBI—Accession No. NP_999299 (2 pgs.) 2011.
NCBI—Accession No. NP_058697 (3 pgs.) 2011.
Abuchowski, A et al, Journal of Biological Chemistry, "Alteration of Immunological Properties of Bovine Serum Albumin by Covalent Attachment of Polyethylene Glycol", 1977, vol. 252, No. 11, pp. 3578-3581.
Abuchowski, A et al, Journal of Biological Chemistry, "Effect of Covalent Attachment of Polyethylene Glycol on Immunogenicity and Circulating Life of Bovine Liver Catalase.", 1977, vol. 252, pp. 3582-3586.
Alam K S M et al, Journal of Biotechnology, "Expression and Purification of a Mutant Human Growth Hormone That Is Resistant to Proteolytic Cleavage by Thrombin, Plasmin and Human Plasma In Vitro", 1998, vol. 65, No. 40942, pp. 183-190.
Abeijon et al., "3'-O-(4-Benzoyl)benzoylcytidine 5'-Triphosphate." Journal of Biological Chemistry, 1986, vol. 261, No. 24, pp. 11374-11377.
Abuchowski et al., Cancer Biochem. Biophys., "Cancer Therapy with Chemically Modified Enzymes. I. Antitumor Properties of Polyethylene Glycol-Asparaginase Conjugates.", 1984, vol. 7, pp. 175-186.
Hoffman et al., "A cell-based model of hemostasis" 2001, Thromb. Haemost. 85(6):958-965.
GE Healthcare, "Ion Exchange Chromatography & Chromatofocusing: Principles and Methods," Edition AA, Amersham Biosciences pp. 7, 11-12, 16-17, 21-23, 26-36, 41, 89, 156, 160, 161 (2004).
Pfaffli et al., "Thioglycosides Having U-Benzyl Blocking Groups as Intermediates for the Systematic, Sequential Synthesis of Oligosaccharides. Synthesis of Isomaltose" 1972, Carbohydr. Res. 23(2):195-206.
Pradel et al., "Structures of the rsfaB, rfaI, rfaJ, and rfaS Genes of *Eschertichia coli* K-12 and Their Roles in Assembly of the Lipopolysaccharide Core" 1992, J. Bacteriol. 174(14):4736-4745.
Keene et al. "Expression of Biologically Active Human Follitropin in Chinese Hamster Ovary Cells" J Biol Chem 264(9): 4769-4775 (1989).
Datta et al., "The Sialyltransferase 'Sialylmotif' Participates in Binding the Donor Substrate CMP-NeuAc" 1995, J. Biol. Chem. 270(4):1497-1500.
Paulson et al., "Tissue-specific Expression of Sialyltransferases" 1989, J. Biol. Chem. 264(19):10931-10934.
Preuss et al., "Purification and Characterization of CMP-N-acetylneuraminic Acid:Lactosylceramide (a2-3) Sialyltransferase (GM3-synthase) from Rat Brain" 1993, J. Biol. Chem. 268(35):26273-26278.
Lonnberg, "Solid Supported Synthesis of Glycoconjugates" Curr. Org. Synth. 6(4): 400-425 (2009).
Probert et al., "Chemoenzymatic Synthesis of GM3, Lewis x and Sialyl Lewis x Oiigosaccharides in 13C-Enriched Form" 1997, Tetrahedron Lett. 38(33):5861-5864.
Monaco et al, "Expression of recombinant human granulocyte colony-stimulating factor in CHO dhfr- cells: new insights into the in vitro amplification expression system" Gene, 180: 145-150 (1996).
Rao et al., "Mutations of endo-b-N-acetylglucosaminidase H active site residues Asp130 and Glu132: Activities and conformations" 1999, Protein Sci. 8(11):2338-2346.
Nagata et al, "The chromosomal gene structure and two mRNAs for human granulocyte colony-stimulating factor" EMBO J, 5(3): 575-581 (1986).
Rearick et al., "Enzymatic Characterization of P-D-Galactoside a2+3 Sialyltransferase from Porcine Submaxillary Gland" 1979, J. Biol. Chem. 254(11):4444-4451.
Natsuka et al. "Molecular cloning of a cDNA encoding a novel human leukocyte alpha-1,3-Fucosyltransferase capable of synthesizing the sialyl Lewis x Determinant" J Biol Chem. 269(24): 16789-16794 (1994).
Rice et al., "Modification of Triantennary Glycopeptide into Probes for the Asialoglycoprotein Receptor of Hepatocytes" 1990, J. Biol. Chem. 265(30):18423-18428.

(56) References Cited

OTHER PUBLICATIONS

Fujita et al., "A novel disaccharide substrate having 1,2-oxazoline moiety for detection of transglycosylating activity of endoglycosidases" 2001, Biochim. Biophys. Acta 1528(1):9-14.

Oh-Eda et al. "O-Linked Sugar Chain of Human Granulocyte Colony-stimulating Factor Protects it Against Polymerization and Denaturation Allowing it to Retain its Biological Activity." J Biol Chem 265: 11432-11435. (1990).

Avigad et al., "The D-Galactose Oxidase of Polyporus circinatus" 1962, J. Biol. Chem 237(9):2736-2743.

GE Healthcare [no author given], 2006, Capto adhere Instructions 28-9064-05 AB.

Orskov et al "Complete Sequences of Glucagon-like Peptide-1 from Human and Pig Small Intestine" J Biol Chem 264 (22): 12826-12829 (1989).

Gross et al., "Enzymatic introduction of a fluorescent sialic acid into oligosaccharide chains of glycoproteins" 1988, Eur. J. Biochem. 177(3):583-589.

Gross et al., "Transfer of Synthetic Sialic Acid Analogues to N- and O-Linked Glycoprotein Glycans Using Four Different Mammalian Sialyltransferases" 1989, Biochemistry 28(18):7386-7392.

Guo et al., "Ultilzation of Glycosyltransferases to Change Oligosaccharide Structures" 1997, Appl. Biochem. Biotechnol. 68(1-2):1-20.

Cohn et al., "Biodegradable PEO/PLA block copolymers" 1988, J. Biomed. Mater. Res. 22(11):993-1009.

Taniguchi et al., "A glycomic approach to the identification and characterization of glycoprotein function in cells transfected with glycosyltransferase genes" 2001, Proteomics 1(2):239.

Amersham Pharmacia Biotech "Hydrophobic Interaction Chromatography: Principles and Methods" p. 104. (2000).

Culajay et al "Thermodynamic Characterization of Mutants of Human Fibroblast Growth Factor 1 with an Increased Physiological Half-Life" Biochem. 39: 7153-7158 (2000).

Hansen et al. "Prediction of O-glycosylation of mammalian proteins: specificity patterns of UDP-GalNAc:polypeptide N-acetylgalactosaminyltransferase" Biochem J. 308: 801-813 (1995).

Liles et al "Augmented mobilization and collection of CD34+ hematopoietic cells from normal human volunteers stimulated with granulocyte-colony-stimulating factor by single-dose administration of AMD3100, a CXCR4 antagonist" Transfusion 45: 295-300 (2005).

Costa et al., "Stable Expression of the Golgi Form and Secretory Variants of Human Fucosyltransferase III from BHK-21 Cells" 1997, J. Biol. Chem. 272(17):11613-11621.

de Vries et al, "Acceptor Specificity of Different Length Constructs of Human Recombinant alpha1.3/4-Fucosyltransferases" 1995, J. Biol. Chem. 270(15):8712-8722.

Maras et al., Journal of Biotechnology, "Molecular Cloning and Enzymatic Characterization of a Trichoderma Reesei 1,2 -Mannosidase", 2000, vol. 77, No. 2-3, pp. 255-263.

Miller et al., Current Opinion in Genetics & Development., "Baculovirus: high-level expression in insect cells", 1993, vol. 3, No. 1, pp. 97-101.

Min et al., Endocrine Journal, "Site-Directed Mutagensis of Recombinant Equine Chorionic Gonadotropin/Luteinzing Hormone: Differetial Role of Oligosaccharides in Luteinizing Hormone- and Follicle-Stimulating Hormone-Like Activities", 1996, vol. 43, No. 5, pp. 585-593.

Mistry et al., Lancet, "Therapeutic delivery of proteins to macrophages: implications for treatment of Gaucher's disease", 1996, vol. 348, No. 9041, pp. 1555-1559.

Morimoto et al., Glycoconjugate Journal, "Biological and physicochemical characterization of recombinant human erythopioetins fractionated by Mono Q column chromatography and their modification with sivalytransferase", 1996, vol. 13, No. 6, pp. 1013-1020.

Nilsson et al., Methods in Enzymology, "Immobilization of Ligands with Organic Sulfonyl Chlorides", 1984, vol. 104, pp. 56-69.

O'Connell, B.C et al, Journal of Biological Chemistry, "The Influence of Flanking Sequence . . . ", 1992, vol. 267, No. 35, pp. 25010-25018.

Oetke et al., Journal of Biological Chemistry, "Versatile Biosynthetic Engineering of Sialic Acid in Living Cells Using Synthetic Sialic Acid Analogues," 2002, vol. 277, No. 8, pp. 6688-6695.

Olson et al., Journal of Biological Chemistry, "Structural Basis for Recognition of Phosphorylated High Mannose Oligosaccharides by the Cation-dependent Mannose 6-Phosphate Receptor", 1999, vol. 274, No. 42, pp. 29889-298996.

Palacpac et al., Proceedings of the National Academy of Sciences of the USA, "Stable expression of human Beta1,4-galactosyltransferase in plant cells modifies N-linked glycosylation patterns", 1999, vol. 96, No. 8, pp. 4692-4697.

Park et al., Journal of Biological Chemistry, "Characterization of the cell surface receptor for a multi-lineage Colony-stimulating Factor (CSF-2alpha)", 1986, vol. 261, No. 1, pp. 205-210.

Paulson et al., Journal of Biological Chemistry, "Reactivation of Asialo-Rabbit Liver Binding Protein Resialyation with B-D-Galactoside a2-6 Sialyltransferase", 1977, vol. 252, No. 23, pp. 8624-8628.

Plummer et al., Journal of Biological Chemistry, "Novel, Specific O-Glycosylation of Secreted *Flavobacterium meningospticum* Proteins", 1995, vol. 270, No. 22, pp. 13192-13196.

Pyatak et al., Res. Commun. Chem. Pathol Pharmacol., "Preperation of a Polyethylene Glycol: Superoxide Dismutase Adduct, and an Examination of its Blood Circulating Life and Anti-Inflammatory Activity", 1980, vol. 29, No. 1, pp. 113-127.

Rabouille et al., Journal of Cell Biology, "The *Drosophila* GMII gene encodes a Golgi alpha-mannosidase II", 1999, vol. 112, No. 19, pp. 3319-3330.

Reff et al., Cancer Control, "Future of Monoclonal Antibodies in the Treatment of Hematologic Malignancies", 2002, vol. 9, No. 2, pp. 152-166.

Reis et al., Biotechnology and Bioengineering, "Industrial Scale Harvest of Proteins from Mammalian Cell Culture by Tangential Flow Filtration", 1991, vol. 38, pp. 413-422.

Rosenthal et al., Methods in Enzymology, "Isolation of Peptidoglycan and Soluble Peptidoglycan Fragments", 1994, vol. 235, pp. 253-285.

Skolnick, J et al, Trends in Biotechnology, "From Genes to Protein Structure and Function: Novel Applications of Computational Approaches in the Genomic Era", 2000, vol. 18, No. 1, pp. 34-39.

Sadler et al., Methods in Enzymology, "Purification of Mammalian Glycosyltransderases", 1982, vol. 83, pp. 458-514.

Sandberg et al., Seminars in Hematology, "Structural and Functional Characterization of B-Domain Deleted Recombinant Factor VIII", 2000, vol. 38, No. 2, pp. 4-12.

Saneyoshi et al., Biology of Reproduction, "Equine Follicle-Stimulating Hormone: Molecular Cloning of Beta Subunit and Biological Role of the Asparagine-Linked Oligosaccharide at Asparagine of alpha Subunit", 2001, vol. 65, No. 6, pp. 1686-1690.

Saxon et al., Science, "Cell Surface Engineering by a Modified Staudinger Reaction", 2000, vol. 287, No. 5460, pp. 2007-2010.

Schlaeger, E., Cytotechnology, "Medium design for insect cell culture", 1996, vol. 20, No. 1-3, pp. 57-70.

Schwientek et al., Gene, "Efficient intra- and extracellular production of human beta-1,4-galactosyltransferase in *Saccharomyces cerevisiae* is mediated by yeast secretion leaders", 1994, vol. 145, No. 2, pp. 299-303.

Schwientek et al., Journal of Biological Chemistry, "Functional Conservation of Subfamilies of Putative UDP-N-acetylgalactosamine:polypeptide N-acetylgalactosaminyltransderases in *Drosophila, Caenorhabditis elegans* and Mammals", 2002, vol. 277, No. 25, pp. 22623-22638.

Scouten, Methods in Enzymology, "A Survey of Enzyme Coupling Techniques", 1987, vol. 135, pp. 30-65.

Hedner et al. "Recombinant Activated Factor VII in the Treatment of Bleeding Episodes in Patients With Inherited and Acquired Bleeding Disorders" Trans. Med. Rev, 7: 78-83 (1993).

Shah et al., Journal of Pharmaceutical Sciences, "Transcellular Delivery of an Insulin-Transferrin Conjugate in Enterocyte-like Caco-2 cells", 1996, vol. 85, No. 12, pp. 1306-1311.

(56) References Cited

OTHER PUBLICATIONS

Shapiro et al., Blood, "The Safety and Efficacy of Recombinant Human Blood Coagulation Factor IX in Previously Untreated Patients With Severe or Moderately Severe Hemophilia B", 2005, vol. 105, No. 2, pp. 518-525.
Singh et al., Chemical Communications, "Glycosidase-catalysed synthesis of oligosaccharides: a two-step synthesis of the core triaccharide of N-linked glycoproteins using the beta-N-acetylhexosaminidase and the betamannosidase from *Aspergillus oryzae*", 1996, vol. 1996, No. 8, pp. 993-994.
Sinha et al., Infection and Immunity, "Release of Soluble Peptidoglycan from Growing Gonococci: Demonstration of Anhydro-Muramyl-Containing Fragments", 1980, vol. 29, No. 3, pp. 914-925.
Smith et al., Nature Biotechnology (Continuation of Bio/Technology), "The Challenges of genome sequence annotation or the devil is inside the details", 1997, vol. 15, No. 12, pp. 1222-1223.
Song et al., The Journal of Pharmacology and Experimental Therapeutics, "Enhanced Neuroprotective Effects of Basic Fibroblast Growth Factor in Regional Brain Ischemia after COnjugation to Blood-Brain Barrier Delivery Vector", 2002, vol. 301, No. 2, pp. 605-610.
Srinivasachar et al., Biochemistry, "New Protein Cross-Linking Reagents that Are Cleaved by Mild Acid", 1989, vol. 28, No. 6, pp. 2501-2509.
Stephen et al., European Journal of Biochemistry, "The Pyruvate Dehydrogenase Complex of *Escherichia coli* K12", 1983, vol. 133, No. 3, pp. 481-489.
Stephens et al., European Journal of Biochemistry, "The Pyruvate Dehydrogenase Complex of *Escherichia coli* K12", 1983, vol. 133, No. 1, pp. 155-162.
Stephens et al., European Journal of Biochemistry, "Nucleotide sequence of the lipoamide dehydrogenase gene of *Escherichia coli* K12", 1983, vol. 135, No. 3, pp. 519-527.
Takane et al., The Journal of Pharmacology and Experimental Therapeutics, "Chronopharmacology of Antitumor Effect Induced by Interferon-Beta in Tumor-Bearing Mice", 2000, vol. 294, No. 2, pp. 746-752.
Takeda et al., Trends in Biochemical Sciences., "GPI-anchor biosynthesis", 1995, vol. 20, No. 9, pp. 367-371.
Takeuchi et al., The Journal of Biological Chemistry, "Role of Sugar Chains in the in Vitro Biological Activity of Human Erythropoietin Produced in Recombinant Chinese Hamster Ovary Cells", 1990, vol. 265, No. 21, pp. 12127-12130.
Tanner et al., Biochimica Et Biophysica Acta, "Protein Glycosylation in Yeast", 1987, vol. 906, No. 1, pp. 81-91.
Tenno et al., Journal of Biological Chemistry, "The Lectin Domain of UDP-GalNAc:Polypeptide N-Acetylgalactosaminyltransferase 1 is Involved in O-Glycosylation of a Polypeptide with Multiple Acceptor Sites", 2002, vol. 277, No. 49, pp. 47088-47096.
Thotakura et al., Methods in Enzymology, "Enzymatic Deglycosylation of Glycoproteins", 1987, vol. 138, pp. 350-359.
Tsuboi et al., Archives of Biochemistry and Biophysics, "Acquisitions of P-selectin Binding Activity by en Bloc Transfer of Sulfo Le Trisaccharide to the Cell Surface: Comparison to a Sialyl Le Tetrasaccharide Transferred on the Cell Surface", 2000, vol. 374, No. 1, pp. 100-106.
Tuddenham, E., Nature, "RNA as Drug and Antidote", 2002, vol. 419, No. 6902, pp. 23-24.
Udenfriend et al., Annual Review of Biochemistry, "How Glycosyl-Phosphatidylinostiol-Anchored Membrane Proteins are Made", 1995, vol. 64, pp. 563-591.
Ulloa-Aguirre et al., Endocrine Journal, "Role of Glycosylation in Function of Follicle-Stimulating Hormone", 1999, vol. 11, No. 3, pp. 205-215.
Uludag et al., Biotechnology Progress, "Targeting Systemically Administered Proteins to Bone by Bisphosphonate Conjugation", 2002, vol. 18, No. 3, pp. 604-611.

Urdal et al., Journal of Chromatography, "Lymphokine Purification by Reversed-Phase High-Performance Liquid Chromatography", 1984, vol. 296, pp. 171-179.
Van Berkel et al., Biochemical Journal, "Heterogeneity in utilization of N-glycosylation sites Asn624 and Asn138 in human lactoferrin: a study with glycosylation-site mutants", 1996, vol. 319, No. 1, pp. 117-122.
Veronese et al., Applied Biochemistry and Biotechnology, "Surface Modification of Proteins", 1985, vol. 11, No. 2, pp. 141-152.
Vyas et al., Critial Reviews in Therapeutic Drug Carrier Systems, "Ligand-Receptor-Mediated Drug Delivery: An Emerging Paradigm in Cellular Drug Targeting", 2001, vol. 18, No. 1, pp. 1-76.
Wang et al., Tetrahedron Letters, "Chemoenzymatic Synthesis of a High-Mannose-Type N-Glycopeptide Analog with C-Glycosidic Linkage", 1996, vol. 37, No. 12, pp. 1975-1978.
Wang, M., Protein Engineering, "Single-chain Fv with manifold N-glycans as bifunctional scaffolds for immunomolecules", 1998, vol. 11, No. 12, pp. 1277-1283.
Wellhoner et al., Journal of Biological Chemistry, "Uptake and COncentration of Bioactive Macromolecules by K562 Cells via the Transferrin Cycle Utilizing an Acid-labile Transferrin Conjugate", 1991, vol. 226, No. 7, pp. 4309-4314.
Wells, J. A., Biochemistry, "Additivity of Mutational Effects in Proteins", 1990, vol. 29, No. 37, pp. 8509-8517.
Witte K. et al., Journal of the American Chemical Society, "Enzymatic Glycoprotein Synthesis: Preperation of Ribonuclease Glycoforms via Enzymatic Glycopeptide Condensation and Glycosylation", 1997, vol. 119, No. 9, pp. 2114-2118.
Woghiren et al., Bioconjugate Chemistry, "Protected Thiol-Polythylene Glycol: A New Activated Polymer for Reversible Protein Modification", 1993, vol. 4, No. 5, pp. 314-318.
Wong et al., Biotechnology and Bioengineering, "Low Multiplicity Infection of Insect Cells with a Recombinant Baculovirus: The Cell Yield Concept", 1996, vol. 49, No. 6, pp. 659-666.
Wong et al., Enzyme and Microbial Technology, "Chemical crosslinking and the stabilization of proteins and enzymes", 1992, vol. 14, No. 11, pp. 866-874.
Detty et al., Journal of Organic Chemistry, "Enzyme-Catalyzed Synthesis of N-Acetyllactosamine with in Situ Regeneration of Uridine 5'-Diphosphate Glucose and Uridine 5'-Diphosphate Galactose", 1982, vol. 47, No. 27, pp. 5415-5418.
Woods et al., European Journal of Cell Biology, "Transferrin receptors and cation-independent mannose-6-phosphate receptors deliver their ligands to two distinct subpopulations of multivesicular endsomes", 1989, vol. 50, No. 1, pp. 132-143.
Wright et al., Journal of Immunology, "Effect of C2-Associated Carbohydrate Structure on Ig Effector Function: Studies with Chimeric Mouse-Human IgG1 Antibodies in Glycosylation Mutants of Chinese Hamster Ovary Cells", 1998, vol. 160, No. 7, pp. 3393-3402.
Wu et al., Journal of Drug Targeting, "Pharmacokintics and Brain Uptake of Biotinylated Basic Fibroblast Growth Factor Conjugated to a Blood-Brain Barrier Drug Delivery System", 2002, vol. 10, No. 3, pp. 239-245.
Xing et al., Biochemical Journal, "Design of a transferrin-proteinase inhibitor conjugate to probe for active cysteine proeinases in endsomes", 1998, vol. 336, No. 3, pp. 667-673.
Yamamoto et al., Carbohydrate Research, "Chemoenzymatic Synthesis of a Novel Glycopeptide using a Microbial Endoglycosidase", 1998, vol. 305, No. 3-4, pp. 415-422.
Yarema et al., Journal of Biological Chemistry, "Metabolic Delivery of Ketone Groups to Sialic Acid Residues", 1998, vol. 47, No. 47, pp. 31168-31179.
Gotschlich, Emil C., Journal of Experimental Medicine, "Genetic Locus for the Biosynthesis of the Variable Portion of *Neisseria gonorrhoeae* Lipooligosaccharide", 1994, vol. 180, No. 6, pp. 2181-2190.
Grabenhorst et al., European Journal of Biochemistry, "Biosynthesis and Secretion of Human Interleukin 2 Glycoprotein Varients From Baculovirus Infected SF21 Cells", 1993, vol. 215, No. 1, pp. 189-197.

(56) References Cited

OTHER PUBLICATIONS

Grodberg et al., European Journal of Biochemistry, "Alanine Scanning mutagensis of Human erythropietin identifies four amino acids which are critical for biological activity", 1993, vol. 218, No. 2, pp. 597-601.

Gross et al., European Journal of Biochemistry, "Fluorescent CMP-sialic acids as a toll to study the specificity of the CMP-sialic acid carrier and the glycoconjugate sialylation in permeabilized cells", 1992, vol. 203, No. 40910, pp. 269-275.

Hagen et al., Journal of Biological Chemistry, "Cloning and Characterization of a Ninth Member of the UDP-GaINAc: Polypeptide N-Acetylgalactosaminyltranseferase Family, ppGaNTase-T9", 2001, vol. 276, Number -, pp. 17395-17404.

Hagen et al., Journal of Biological Chemistry, "Structure-FUnction Analysis of the UDP-N-acetyl-D-galactosamine: Polypeptide N-Acetylgalactosaminyltranseferase", 1999, vol. 274, No. 10, pp. 6797-6803.

Hall et al., Methods in Molecular Biology, "Immunotoxin Treatment of Brain Tumors", 2001, vol. 166, pp. 139-154.

Haneda et al., Carbohydrate Research, "Transglycosylation of intact sialo complex-type oligosaccharides to the N-acetylglucosamine moieties of glycopeptides by *Mucor hiemalis* endo-Beta-N-Acetylglucosaminidase", 1996, vol. 292, pp. 61-70.

Hang et al., Journal of the American Chemical Society, "Ketone Isosteres of 2-N-Acetamidosugars as Substrates for Metabolic Cell Surface Engineering", 2001, vol. 123, No. 6, pp. 1242-1243.

Harris, Macronol. Chem. Phys., "Laboratory Synthesis of Polythylene Glycol Derivatives", 1985, vol. C25, No. 3, pp. 325-373.

Harris et al., Abstracts of Papers—American Chemical Society., "Synthesis of Polyethylene Glycol Thiol", 1991, vol. 201, pp. 154-155.

Harris et al., Nature Reviews. Drug Discovery., "Effect of Pegylation on Pharmaceuticals", 2003, vol. 2, No. 3, pp. 214-221.

Hassan et al., Journal of Biological Chemistry, "The Lectin Domain of UDP-N-acetyl-D-galactosamine: Polypeptide N-acetylgalactosaminyltranseferase-T4 Directs its Glycopeptide Specificities", 2000, vol. 275, No. 49, pp. 38197-38205.

Hayes et al., Journal of Biological Chemistry, "The biosynthesis of Oligosaccharides in Intact Golgi Preparations from Rat Liver", 1993, vol. 268, No. 22, pp. 16170-16178.

Hellstrom et al., Methods in Molecular Biology, "Development and Activities of the BR96-Doxorubicin Immunoconjugate", 2001, vol. 166, pp. 3-6.

Hermentin et al., Glycobiology, "The hypothetical N-Glycan Charge: A Number that Characterizes Protein Glycosulation", 1996, vol. 6, No. 2, pp. 217-230.

Hills et al., American Biotechnology Laboratory, "Control of Therapeutic Monoclonal Antibody Glycosylation Through the Addition of Sugar Media Components and In Vitro Remodeling", 2002, vol. 20, No. 11, pp. 30.

Hink et al., Biotechnology Progress, "Expression of Three Recombinant Proteins Using Baculovirus Vectors in 23 Insect Cell Lines." 1991, vol. 7, pp. 9-14.

Hollister et al., Glycobiology, "Engineering lepidopteran insect cells for sialglycoprotein production by genetic transformation with mammalian beta1,4-galactosyltransferase and alpha2,6-sialytransferase genes", 2001, vol. 11, No. 1, pp. 1-9.

Hounsell et al., Glycoconjugate Journal, "O-linked Protein Glycosylation Structure and Function", 1996, vol. 13, No. 1, pp. 19-26.

Ichikawa et al., Journal of the American Chemical Society, "Chemical-Enzymatic Synthesis and Conformational Analysis of Sialyl Lewis x and Derivatives", 1992, vol. 114, No. 24, pp. 9283-9298.

Ikonomou et al., In Vitro Cellular & Developmental Biology Animal, "Design of an Efficient Medium for Insect Cell Growth and Recombinant Protein Production", 1991, vol. 37, No. 9, pp. 549-559.

Inlow et al., J. Tissue Culture Meth., "Insect Cell Culture and Baculovirus Propagation in Protein-Free Medium", 1989, vol. 12, No. 1, pp. 13-16.

Inoue et al., Biotechnology Annual Review, "The Production of Recombinant Human Erythropoetin", 1995, vol. 1, pp. 297-313.

Ito et al., Pure and Applied Chemistry, "Synthesis of Bioactive Sialosides", 1993, vol. 65, No. 4, pp. 753-762.

Jackson et al., Analytical Biochemistry, "Synthesis, Isolation and Characterization of Conjugates of Ovalbumin with Monomethoxypolyethylene Gycol Using Cyanuric Chloride as the Coupling Agent", 1987, vol. 165, No. 1, pp. 114-127.

Jarvis et al., Current Opinion in Biotechnology, "Engineering N-glycosylation Pathways in the Baculovirus-Insect Cell System.", 1998, vol. 9, No. 5, pp. 528-533.

Joppich et al., Makromol Chem., "Peptides Flanked by Two Polymer Chains, 1 Synthesis of Glycycl-L-tryptophylglycine Substituted by Poly(ethylene oxide) at both the Carboxy and the Amino End Groups", 1979, vol. 180, pp. 1381-1384.

Joshi et al., Journal of Biological Chemistry, "ATP Synthase Complex from Bovine Heart Mitochondria", 1990, vol. 265, No. 24, pp. 14518-14525.

Jung et al., Biochemical and Biophysical Acta, "Crosslinking of Platelet Glycoprotein Ib by N-Succinimidyl(4-Azidophenyldithio)Propionate and 3,3'-Dithiobis(Sulfosuccinimidyl Propionate)", 1983, vol. 761, No. 2 pp. 152-162.

Kalsner et al., Glycoconjugate Journal, "Insertion into *Aspergillus nidulans* of Functional UDP-GIuNAcL Aplha3-D-mannoside Beta-1,2-N-acetylglucosaminyltransferase I, the enzyme catalysing the first committed step from oligomannose to hybrid and complex N-glycans", 1995, vol. 12, No. 3, pp. 360-370.

Kasina et al., Bioconjugate Chemistry, "Simplified Preformed Chelate Protein Radiolabeling with Technetium-99m Mercaptoacetamidoadipoylglycylglycine (N3S-Adipate)", 1998, vol. 9, No. 1, pp. 108-117.

Katre et al., Proceedings of the National Academy of Sciences of the USA, "Chemical Modification of recombinant interleukin 2 by polythylene glycol increases its potency in the murine Meth A sarcoma model", 1987, vol. 84, No. 6, pp. 1487-1491.

Keppler et al., Glycobiology, "Biochemical Engineering of the N-acyl side Chain of Sialic Acid: Biological Implications", 2001, vol. 11, No. 2, pp. 11R-18R.

Kitamura et al., Biochemical and Biophysical Research Communications, "Polyethylene Glycol Modification of the Monoclonal Antibody at Enhances its Tumor Localization", 1990, vol. 171, No. 3, pp. 1387-1394.

Kitamura et al., Cancer Research, "Chemical Engineering of the Monoclonal Antibody A7 by polyethylene Glycol for Targeting Cancer Chemotherapy", 1991, vol. 51, No. 16, pp. 4310-4315.

Kodama et al., Tetrahedron Letters, "Synthesis of UDP-6-Deoxy and -6-Fluoro-D-Galactoses and their Enzymatic Glycosul Transfer to Mono- and Blantennary Carbohydrate Chains", 1993, vol. 34, No. 40, pp. 6419-6422.

Koeller et al., Nature, "Enzyme for Chemical Synthesis", 2001, vol. 409, No. 6817, pp. 232-240.

Koeller et al., Nature Biotechnology (Continuation of Bio/Technology), "Emerging Themes in Medicinal Glycoscience", 2000, vol. 18, No. 8, pp. 835-841.

Koide et al., Biochemical and Biophysical Research Communications, "Modification of Amino Groups in Porcine Pancreatic Elastase With Polythylene Glycol in Relation to Binding Ability Towards Anti-Serum and to Enzymic Activity", 1983, vol. 111, No. 2, pp. 659-667.

Kreitmann, Current Pharmaceutical Biotechnology, "Toxin Labeled Monoclonal Antibodies", 2001, vol. 2, No. 4, pp. 313-325.

Kuhn et al., Journal of Biological Chemistry, "Active Site and Oligosaccharide Recognition Residues of Peptide-N4-(N-acetyl-beta-D-glucosaminyl)asparagine Amidase F", 1995, vol. 270, No. 49, pp. 29493-29497.

Lai et al., Journal of Biological Chemistry, "Structural Characterization of Human Erythropoietin", 1986, vol. 261, No. 7, pp. 3116-3121.

Lau et al., Journal of Biotechnology, "Quantitative Competitive Reverse Transcription-PCR as a Method to Evaluate Retrovirus Removal During Chromatography Procedures", 1999, vol. 75, No. 2-3, pp. 105-115.

(56) References Cited

OTHER PUBLICATIONS

Lee et al., Biochemistry, "Efficient Coupling of Glycopeptides to Proteins with a Heterobifunctional Reagent", 1989, vol. 28, No. 4, pp. 1856-1861.
Lee-Huang et al., Proceedings of the National Academy of Sciences of the USA, "Cloning and Expression of Human Erythropoietin cDNA in *Escherichia coli*", 1984, vol. 81, No. 9, pp. 2708-2712.
Leung, S., Journal of Immunology, "Engineering a Unique Glycosylation Site for Site-Specific Conjugation of Haptens to Antibody Fragments", 1995, vol. 154, No. 11, pp. 5919-5926.
Li et al., Medicinal Research Reviews., "Transferrin/Transferrin Receptor-Mediated Drug Delivery", 2002, vol. 22, No. 3, pp. 225-250.
Li et al., Trends in Pharmacological Sciences., "The role of transferrin-transferrin-receptor system in drug delivery and targeting", 2002, vol. 23, No. 5, pp. 206-209.
Licari P. et al., Biotechnology and Bioengineering, "Baculovirus-Infected Cells: Optimizing Infection Strategies for Enhanced Recombinant Protein Yields", 1992, vol. 39, No. 4, pp. 432-441.
Seitz, "Glycopeptide Synthesis and the Effects of Glycosylation on Protein Structure and Activity." 2000, Chembiochem 1(4):214-246.
Shen et al., "CIS-Aconityl Spacer Between Daunomycin and Macromolecular Carriers: A Model of PH-Sensitive Linkage Releasing Drug From a Lysomotropic Conjugate" 1981, Biochem. Biophys. Res. Commun. 102(3):1048-1054.
Rudikoff et al., "Single amino acid substitution altering antigen-binding specificity" 1982, Proc. Natl. Acad. Sci. USA 79 (6):1979-1983.
PNGase-F Amidase Sequence from *F. meningosepticum* (Registry Nos. 128688-70-0) 2007.
PNGase-F Amidase Sequence from *F. meningosepticum* (Registry Nos. 128688-71-1) 2007.
Prieels et al., "Co-Purification of the Lewis Blood Group N-Acetylglucasminide alphal-4 Fucosyltransferase and an N-Acetylglucasminide alpha1-3 Fucosyltransferase from Human Milk" 1981, J. Biol. Chem. 256(20):10456-10463.
Palcic et al., "Enzymic Synthesis of Oligosaccharides Terminating in the Tumor-Associated Sialyl-Lewis-a Determinant" 1989, Carbohydr. Res. 190(1):1-11.
Nunez et al., "The Synthesis and Characterization of alpha and beta-L-fucopyranosyl phosphates and GDP fucose" 1981, Can. J. Chem. 59(14):2086-2095.
Mollicone et al., "Acceptor specificty and tissue distribution of three human alpha-3-fucosyltranferases" 1990, Eur. J. Biochem. 191(1):169-176.
Muller et al., "Localization of O-Glycosylation Sites on Glycopeptide Fragments from Lactation-associated MUC1" 1997, J. Biol. Chem., 272(40):24780-24793.
Muller et al., "High Density O-Glycosylation on Tandem Repeat Peptide from Secretory MUC1 of T47D Breast Cancer Cells" 1999, J. Biol. Chem., 274(26):18165-18172.
NCBI—Accession No. NCAA26095 (2 pgs.) Accessed Sep. 29, 2011.
NCBI Database hits for erythropoietin protein sequences (3 pgs.) Accessed Sep. 29, 2011.
Ngo et al., 1994, "The Protein Folding Problem and Tertiary Structure Prediction, Chapter 14: Computational Complexity Protein Structure Prediction, and the Levinthal Paradox" pp. 433-440 and 492-495.
Meynial-Salles et al., "In vitro glycosylation of proteins: An enzymatic approach" 1996, J. Biotechnol. 46(1):1-14.
Malissard et al., "Expression of Functional Soluble Forms of Human Beta-1, 4-Galactosyltransferase I, alpha-2, 6-Sialyltransferase and alpha-1,3-Fucosyltranserase VI in the Methylotrophic Yeast *Pichia pastoris.*" 2000, Biochem. Biophys. Res. Commun. 267(1):169-173.
Broun et al., "Catalytic Plasticity of Fatty Acid Modification Enzymes Underlying Chemical Diversity of Plant Lipids" 1998, Science 282(5392):1315-1317.
Harker 1997 "Antithrombotic strategies targeting thrombin activities, thrombin receptors and thrombin generation." Throm. and Haemo. 1997 vol. 78(1): 736-741.
Schachter and Brockhausen, "The Biosynthesis of Branched O-Linked Glycans." 1989. Society for Experimental Biology. p. 1-26.
Hoglund, "Glycosylated and non-glycosylated recombinant human granulocyte colony-stimulating factor (rhG-CSF)—what is the difference?" 1998, Med. Oncol. 15(4):229-233.
Ghose, TI. Cytotoxicty Tests and Cytotoxic Agents. Methods in Enzymology. Academic Press Inc. San Diego CA 1983 vol. 93 pp. 280-333.
Sigma Chemical Company Catalog. 1990 pp. 217, 461, 729.
Wong et al. 1982, "Enzyme Catayzed Synthesis of N-Acetyl-lactosamine with in Situ Regeneration of Uridine 5'-Diphosphate Glucose and Uridine 5'-Diphosphate Galactose" J. Org. Chem. 47(27): 5416-5418.
Weerapana et al., "Investigating Bacertial N-Linked Glycosylation: Synthesis and Glycosyl Acceptor Activity of the Undecaprenyl Pyrophosphate-Linked Bacillosamine," J. Am. Chem. Soc., 127(40): 13766-13767 (2005).
Seely et al. "Use of ion-exchange chromatography and hydrophobic interaction chromatography in the preparation and recovery of polyethylene glycol-linked proteins" J Chromatog. 908: 235-241 (2001).
Kurosawa et al., "Molecular cloning and expression of chick embryo Gal/?l,4GlcNAca2,6-sialyltransferase Comparison with the mammalian enzyme" 1994, Eur. J. Biochem. 219(1-2):375-381.
Shinkai et al. "High level Expression and Purification of a Recombinant Human alpha-1,3-Fucosyltransferase in Baculovirus-Infected Insect Cells" Prot Exp Purif, 10: 379-385 (1997).
Larsen et al, "Isolation of a cDNA encoding a murine UDPgalactose:1B-D-galactosyl- 1,4-N-acetyl-D-glucosaminide at-1,3-galactosyltransferase: Expression cloning by gene transfer" 1989, Proc. Natl. Acad. Sci. USA 86(21):8227-8231.
Yamada et al., "Selective Modification of Aspartic Acid-101 in Lysozyme by Carbodiimide Reaction" 1981, Biochemistry 20(17):4836-4842.
Hassan et al., "Control of Mucin-Type O-Glycosylation: O-glycan Occupancy is Directed by Substrate Specificities of Polypeptide GaINAc-Transferases" 2000, Carbohydrates in Chemistry and Biology, Part II, 3:273-292.
Swiss-Prot Accession No. P27129 (Aug. 1, 1992).
Takegawa et al. "Synthesis of Neoglycoproteins Using Oligosaccharide-transfer Activity with Endo-Beta-N-Acetylglucosaminidase", 1995, J. Biol. Chem. 270(7):3094-3099.
Parsons et al., "Sialylation of lipopolysaccharide and loss of absorption of bactericidal antibody during conversion of gonococci to serum resistance by cytidine 5'-monophospho-N-acetyl neuraminic acid" 1989, Microb. Pathog. 7(1):63-72.
Patra et al., "Optimication of Inclusion Body Solubilization and Renaturation of Recombinant Human Growth Hormonoe from *Escherichia coli*" 2000, Protein Expr. Purif. 18(2):182-192.
Mandrell, "Further Antigenic Similarities of *Neisseria gonorrhoeae* Lipooligosaccharides and Human Glycosphingolipids" 1992, Infect. Immun. 60(7)3017-3020.
Marinier et al. "Sulfated Galactocerebrosides as Potential Antiinflammatory Agents", 1997, J. Med. Chem. 40 (20):3234-3247.
Mathews et al., "Mass Spectrometrically Derived Amino Acid Sequence of Thioredoxin from Chlorobium, an Evolutionarily Prominent Photosynthetic Bacterium" 1987, J. Biol. Chem. 262(16):7537-7545.
Wikipedia (2007, updated) Image:Ceramide.svg, http://en.wikipedia.org/wiki/Ceramide, pp. 1-2.
Wong et al., "Regeneration of Sugar Nucleotide for Enzymatic Oligosaccharide Synthesis: Use of Gal-1-Phosphate Uridyltransferase in the Regeneration of UDP-Galactose, UDP-2-Deoxygalactose, and UDP-Galactosamine" 1992, J. Org. Chem. 57(16):4343-4344.
Wang et al., "The role of the Cys191-Cys220 disulfide bond in trypsin: ew targets for engineering substrate specificity" 1997, Protein Eng. 10(4):405-411.

(56) References Cited

OTHER PUBLICATIONS

Webster et al., "Primary Structures of Both Subunits of *Escherichia coli* Glycyl-tRNA Synthetase" 1983, J. Biol. Chem. 258(17):10637-10641.
Weinstein et al., "Purification of a Gal/31+4GlcNAc a2+6 Sialyltransferase and a Gal/I1-,3(4)GlcNAc a2+3 Sialyltransferase to Homogeneity from Rat Liver" 1982, J. Biol. Chem. 257(22):13835-13844.
Weinstein et al., "Sialylation of Glycoprotein Oligosaccharides N-linked to Asparagine" 1982, J. Biol. Chem. 257 (22):13845-13853.
Tsujihara et al., "A New Class of Nitrosoureas" 1981, Chem. Pharm. Bull. (Tokyo) 29(11):3262-3273.
Van den Eijnden et al., "Detection of P-Galactosyl(I+4)Nacetylglucosaminide 4 2+3)-Sialyltransferase Activity in Fetal Calf Liver and OtherT issues" 1981, J. Biol. Chem. 256(7):3159-3162.
Yamasaki et al., "Neuraminic Acid Is a2->3 Linked in the Lipooligosaccharide of *Neisseria meningitidis* Serogroup B Strain 6275" 1993, J. Bacteriol. 175(14):4565-4568.
Yoshikawa et al., "Aroma Glycosides From *Hovenia* Dulsis" 1993, Phytochemistry 34(5):1431-1433.
Zalipsky et al., "Preparation of Polythylene Glycol Derivatives with Two Different Functional Groups at the Termini" 1986, Polymer Prepr. 2:1-2.
Sandlin et al., "Role of Phosphoglucomutase in Lipooligosaccharide Biosynthesis in *Neisseria gonorrhoeae*" 1994, J. Bacteriol. 176(10):2930-2937.
Kitagawa et al., "Cloning and Expression of Human GalBeta1,3(4)GlcNAc alpha2,3-Sialyltransferase" 1993, Biochem. Biophys. Res. Commun. 194(1):375-382.
Kitagawa et al., "Differential Expression of Five Sialyltransferase Genes in Human Tissues" 1994, J. Biol. Chem. 269 (27):17872-17878.
Knight et al., "Identification and characterization of a novel insertion sequence, IS1106, downstream of the porA gene in B15 *Neisseria meningitidis*" 1992, Mol. Microbiol. 6(11):1565-1573.
Kogan, "The Synthesis of Substituted Methoxy-Poly(Ethlenglycol) Derivatives Suitable for Selective Protein Modification" 1992, Synth. Commun. 22(16):2417-2424.
Lee et al., "Generation of cDNA Probes Directed by Amino Acid Sequence: Cloning of Urate Oxidase" 1988, Science 239(4845):1288-1291.
Lin et al, "Cloning and expression of the human erythropoietin gene" Proc Natl Acad Sci USA 82: 7580-7584 (1985).
Witkowski et al., "Conversion of a beta-Ketoacyl Synthase to a Malonyl Decarboxylase by Replacement of the Active-Site Cysteine with Glutamine" 1999, Biochemistry 38(36):11643-11650.
Lidholt et al, "Biosynthesis of heparin" 1989, Biochem. J. 261(3):999-1007.
Rotondaro et al, "Purification and Characterization of Two Recombinant Human Granuiocyte Colony-Stimulating Factor Glycoforms" Mol Biotech, 11: 117-128 (1999).
Livingston et al., "Polymerase Chain Reaction Cloning of a Developmentally Regulated Member of the Sialyltransferase Gene Family" 1993, J. Biol. Chem. 268(16):11504-11507.
Sasaki et al, "Carbohydrate Structure of Erythropoietin Expressed in Chinese Hamster Ovary Cells by a Human Erythropoietin cDNA" J Biol Chem 262(25): 12059-12076 (1987).
Lundstrom-Ljung et al., "Glutaredoxin Accelerates Glutathione-dependent Folding of Reduced Ribonuclease A Together with Protein Disulfide-isomerase" 1995, J. Biol. Chem. 270(14):7822-7828.
Sasaki et al. "Expression Cloning of a Novel alpha1,3-Fucosyltransferase that is involved in Biosynthesis of the Sialyl Lewis X Carbohydrate Determinants in Leukocytes." J Biol Chem 269: 14730-14737 (1994).
Maccioni et al., "Organization of ganglioside synthesis in the Golgi apparatus" 1999, Biochim Biophys Acta. 1437(2):101-118.
Mackenzie et al., "Glycosynthases: Mutant Glycosidases for Oligosaccharide Synthesis" 1998, J. Am. Chem. Soc. 120 (22):5583-5584.
Fan et al., Journal of Biological Chemistry, "Detailed Studies on Substrate Structure Requirements of Glycoamidases A and F", 1997, vol. 272, No. 43, pp. 27058-27064.
Fibi et al., Cells Blood, "N- and O-Glycosylation Muteins of Recombinant Human Erythropoietin Secreted from BHK-21 Cells", 1995, vol. 85, No. 5, pp. 1229-1236.
Fischer et al., Thrombosis Research, "Recominant Coagulation Factor IX: Glycosylation Analysis and In Vitro Conversion into Human-Like Sialylation Pattern", 1998, vol. 89, No. 3, pp. 147-150.
Flynn et al., Current Opinion in Oncology, "Campath-1H monoclonal antibody therapy", 2000, vol. 12, No. 6, pp. 574-581.
Fritz et al., Journal of Biological Chemistry, "Dynamic Association between the Catalytic and Lectin Domains of Human UDP__GalNAc: Polypeptide alpha-N-Acetylgalactosaminyltransferase-2", 2006, vol. 281, No. 13, pp. 8613-8619.
Fritz et al., Proceedings of the National Academy of Sciences of the USA, "Adaptor Protein Protects Against Cerebral Ischemia", 2004, vol. 101, No. 43, pp. 15307-15312.
Garnett et al., Advanced Drug Delivery Reviews, "Targeted Drug Conjugates: Principles and Progress", 2002, vol. 53, No. 2, pp. 171-216.
Gatot et al., Journal of Biological Chemistry, "Conservative Mutations in the Immunosuppressive Region of the Bovine Leukemia Virus Transmembrane Protein Affect Fusion but not Infectivity in Vivo", 1998, vol. 273, No. 21, pp. 12870-12880.
Gilbert et al., Cytotechnology, "Effect of Lipids on Insect Cell Growth and Expression of Recombinant Proteins in Serum-Free Medium", 1996, vol. 22, No. 1-3, pp. 211-216.
Gillis et al., Behring Inst. Mitt. August, "Production of Recombinant Human Colony Stimulating Factors in Yeast", 1988, vol. 83, pp. 1-7.
Brockhausen et al. "Glycoproteins and Their Relationship to Human Disease" Glycoconj J. 15: 595-603 (1998).
Fu et al., "Carbohydrate-Directed Conjugation of Cobra Venom Factor to Antibody by Selective Derivatization of the Terminal Galactose Residues" 2001, Bioconjug. Chem. 12(2):271-279.
Ichikawa et al., "Enzyme-Catalyzed Synthesis of Sialyl Oligosaccharide with in Situ Regeneration of CMP-Sialic Acid" 1991, J. Am. Chem. Soc. 113(12):4698-4700.
Keana et al., "New Reagents for Photoaffinity Labeling: Synthesis and Thotolysis of Functionalized Pertluorophenyl Azides." 1990, J. Org. Chem. 55(11):3640-3647.
Danaher et al., "Genetic Basis of *Neisseria gonorrhoeae* Lipooligosaccharide Antigenic Variation" 1995, J. Bacteriol. 177(24):7275-7279.
Borman, "Glycosylation Engineering: Controlling personalities tame wild sugars on proteins and natural products" 2006, Chem. Eng. News 84(36):13-22.
Factor IX of *Homo sapien*, GenBank Accession No. CAA01607 p. 1-2 Accessed Apr. 14, 2009.
Factor IX, Genbank Accession No. AAA98726 p. 1-3 Accessed Apr. 14, 2009.
Arsequell et al., "Recent advances in the synthesis of complex N-glycopeptides" 1999, Tetrahedron: Asymmetry 10(16):3045-3094.
Bertozzi et al., "Carbon-Linked Calactosphingolipid Analogs Bind Specifically to HIV-1 gpl20" 1992, J. Am. Chem. Soc. 114(26):10639-10641.
Greenwell et al., "UDP-N-Acetyl-D-Galactosamine as a Donor Substrate for the Glycosyltransferase Encoded by the B Gene at the Human Blood Group ABO Locus" 1986, Carbohydr. Res. 149(1):149-170.
Hakomori et al., 1974, "Methods in Enzymology" Fleischer et al. (eds.), Chapter 33, pp. 345-367, vol. 32, Biomembranes Part B, Elsevier USA.
Mandrell et al., "In Vitro and In Vivo Modification of *Neisseria gonorrhoeae* Lipooligosaccharide Epitope Structure by Sialylation" 1990, J. Exp. Med. 171(5):1649-1664.
Nucci et al., "The therapeutic value of poly(ethylene glycol)-modified proteins" 1991, Adv. Drug Deily. Rev. 6(2):133-151.
Paulson et al., "Purification of a sialyltransferase from bovine colostrum by affinity chromatography on CDP-agarose" 1977, Chemical Abstracts 86(25), 213 [abstract No. 185016b].

(56) References Cited

OTHER PUBLICATIONS

Simon et al., "Synthesis of CMP-NeuAc from N-Acetylglucosamine: Generation of CTP from CMP Using Adenylate Kinase" 1988, J. Am. Chem. Soc. 110(21):7159-7163.
Suzuki et al., "N-Acetylneuraminyllactosylceramide, GM3-NeuAc, a New Influenza A Virus Receptor Which Mediates the Adsorption-Fusion Process of Viral Infection" 1985, J. Biol. Chem. 260(3):1362-1365.
van den Eijnden et al., "Novikoff ascites tumor cells contain N-acetyllactosaminide beta 1 leads to 3 and beta 1 leads to 6 N-acetylglucosaminyltransferase activity." 1983, J. Biol. Chem. 258(6):3435-3437.
Wakarchuk et al., "Functional Relationships of the Genetic Locus Encoding the Glycosyltransferase Enzymes Involved in Expression of the Lacto-N-neotetraose Terminal Lipopolysaccharide Structure in *Neisseria meningitidis*" 1996, J. Biol. Chem. 271(32):19166-19173.
Whisstock et al., "Prediction of proteinfunction fromprotein sequence and structure" 2003, Q. Rev. Biophys. 36 (3):307-340.
Yamamoto et al., "Molecular genetic Basis of Histo-blood group ABO System" 1990, Nature 345(6272):229-233.
Zhou et al., "Lipooligosaccharide Biosynthesis in Pathogenic *Neisseria*" 1994, J. Biol. Chem. 269(15):11162-11169.
Orlean, 1997, "vol. III: The Molecular and Cellular Biology of the Yeast *Saccharomyces:* Cell Cycle and Cell Biology", Chapter 3 "Biogenesis of Yeast Wall and Surface Components", pp. 229-362, Cold Spring Harbor Laboratory Press.
Rasko et al., "Cloning and Characterization of the a(1,3/4) Fucosyltransferase of *Helicobacter pylori*" 2000, J. Biol. Chem. 275(7):4988-4994.
Schwarz et al., "Transfer of 131I and Fluoresceinyl Sialic Acid Derivatives into the Oligosaccharide Chains of IgG: A New Method for Site-Specific Labeling of Antibodies" 1999, Nucl. Med. Biol. 26(4):383-388.
Vijay et al., "Properties of Membrane-associated Sialyltransferase of *Escherichia coli*" 1975, J. Biol. Chem. 250 (1):164-170.
Waddling et al., "Structural Basis for the Substrate Specificity of Endo-â-N-acetylglucosaminidase F3" 2000, Biochemistry 39(27):7878-7885.
Schneider et al., "Expression of Paragloboside-like Lipooligosaccharides May Be a Necessary Component of Gonococcal Pathogenesis in Men" 1991, J. Exp. Med. 174(6):1601-1605.
Schram et al., "The Identity of a-Galactosidase B From Human Liver" 1977, Biochim. Biophys. Acta 482(1):138-144.
Sears et al., "Toward Automated Synthesis of Oligosaccharides and Glycoproteins" 2001, Science 291(5512):2344-2350.
Sogin et al., "Binding of Cytochalasin E3 to Human Erythrocyte Glucose Transporter" 1980, Biochemistry 19(23):5417-5420.
Stamenkovic et al., "The B Cell Antigen CD75 Is a Cell Surface Sialyltransferase" 1990, J. Exp. Med. 172(2):641-643.
Stennicke et al., "C-Terminal Incorporation of Fluorogenic and Affinity Labels Using Wild-Type and Mutagenized Carboxypeptidase Y" 1997, Anal. Biochem. 248(1):141-148.
Stephens et al., "Tn916-Generated, Lipooligosaccharide Mutants of *Neisseria meningitidis* and *Neisseria gonorrhoeae*" 1994, Infect Immun. 62(7):2947-2952.
Stoolmiller et al., "The Biosynthesis of Hyaluronic Acid by *Streptococcus*" 1969, J. Biol. Chem. 244(2):236-246.
Swiss-Prot Accession No. P19817 (Feb. 1, 1991).
Takeya et al., "Bovine Factor VII" 1988, J. Biol. Chem. 263(29):14868-14877.
Takeya et al., "Biosynthesis of the Blood Group P Antigen-like GalNAcBeta1-3GalBeta1-4GlcNAc/Glc Structure: Kinetic Evidence for the Responsibility of N-Acetylglucosaminyl-Transferase" 1993, Jpn. J. Med. Sci. Biol. 46(1):1-15.
Tarui et al., "A Novel Cell-Free Translation/Glycosylation System Prepared from Insect Cells" 2000, J. Biosci. Bioeng. 90(5):508-514.
Toone et al., "Enzyme-Catalyzed Syntehsis of Carbohydrates" 1989, Tetrahedron 45(17):5365-5422.

Tsai et al., "Eight Lipooligosaccharides of *Neisseria meningitidis* React with a Monoclonal Antibody Which Binds Lacto-N-Neotetraose (Ga131-4G1cNAcl1-3Gal31-4Glc)" 1991, Infect. Immun. 59(10):3604-3609.
van Putten et al., "Phase variation of lipopolysaccharide directs interconversion of invasive and immuno-resistant phenotypes of *Neisseria gonorrhoeae*" 1993, EMBO J. 12(11):4043-4051.
Van Roey al., "Crystal Structure of Endo-P-N-acetylglucosaminidaseF 1 , an a/P-Barrel Enzyme Adapted for a Complex Substrate" 1994, Biochemistry 33(47):13989-13996.
Vann et al., "Purification, Properties, andG enetic Location of *Escherichia coli* Cytidine 5'-Monophosphate N-Acetylneuraminic Acid Synthetase" 1987, J Biol Chem. 262(36):17556-17562.
Verheul et al., "Meningococcal Lipopolysaccharides: Virulence Factor and Potential Vaccine Component" 1993, Microbiol. Rev. 57(1):34-49.
White et al. "Purification and cDNA cloning of a human UDP-N-acetyl-alpha-D-galactosamine: polypeptide N-Acetylgalactosaminyltransferase" J Biol Chem 270(41): 24156-24165 (1995).
Schmidt et al., 2003, "Structure-Function Relationships in Factor IX and Factor IXa" Trends Cardiovasc. Med. 13(1):39-45.
Witte et al. "Monoclonal antibodies targeting the VEGF receptor-2 (Flk1/KDR) as an anti-angiogenic therapeutic strategy" Cancer and Metastasis Rev, 17: 155-161 (1998).
Schneider et al., "Instability of Expression of Lipooligosaccharides and Their Epitopes in *Neisseria gonorrhoeae*" 1988, Infect. Immun. 56(4):942-946.
Shames et al., "CMP-iY-acetylneuraminic acid synthetase of *Escherichia coli*: high level expression, purification and use in the enzymatic synthesis of CMP-iV-acetylneuraminic acid and CMP-neuraminic acid derivatives" 1991, Glycobiology 1(2):187-191.
Rabina, J et al. "Analysis of nucleotide sugars from cell lysates by ion-pair solid-phase extraction and reversed-phase high-performance liquid chromatography" Glycoconjugate Journal. vol. 18: 799-805. 2001.
Yoshida et al., Glycobiology, "Expression and Characterization of rat UDP-N-acetylglucosamine: alpha-3-D-mannoside beta-1,2-N-acetylhlucosaminyltransferase I in *Saccharomyces cerevisiae*", 1999, vol. 9, No. 1, pp. 53-58.
Yoshitake et al., Biochemistry, "Nucleotide Sequence of the Gene for Human Factor IX (Antihemophilic Factor B)", 1985, vol. 24, No. 14, pp. 3736-3750.
Zheng et al., Biotechnology and Bioengineering, "Optimized Production of Recombinant Bluetongue Core-Like Particles Produced by the Baculovirus Expression System", 1999, vol. 65, No. 5, pp. 600-604.
Zhou et al., Molecular Microbiology, "Lipooligosaccharide biosynthesis in *Neisseria gonorrhoear*: cloning, identification and characterization of the alpha1,5 heptosyltransferase I gen (rfaC)", 1994, vol. 14, No. 4, pp. 609-618.
Bijsterbosch et al., "Quantitative analysis of the targeting of mannose-terminal glucocerebrosidase Predominant uptake by liver endothelial cells" 1996, Eur. J. Biochem. 237(2):344-349.
Zalipsky et al., "A convenient general method for systhesis of Na-or N.-dithiasuccionoyl (Dts) amino acids and dipeptides: application of polyethylene glycol as a carrier for functional purification," 1987, Int. J. Pept. Protein Res. 30(6):740-783.
van Tetering et al., "Characterization of a core K1C3-fucosyltransferase from the snail *Lymnaea stagnalis* that is involved in the synthesis of complex-type N-glycans" 1999, FEBS Letters, 461(3):311-314.
Veronese, "Peptide and protein PEGylation: a review of problems and solutions" 2001, Biomaterials 22(5):405-417.
Vocadlo et al., 2000, "Carbohydrate Chemistry and Biology, vol. 2", Chapter 29 "Glycosidase-Catalysed Oligosaccharide Synthesis", pp. 723-844.
Wang et al., "Identification of a GDP-L-fucose:polypeptide fucosyltransferase and enzymatic addition of O-linked fucose to EGF domains" 1996, Glycobiology 6(8):837-842.
Wang et al., "Novel Helicobacter pylori a1,2- fucosyltransferase, a key enzyme in the synthesis of Lewis antigens" 1999, Microbiology 145(Pt. 11):3245-3253.

(56) References Cited

OTHER PUBLICATIONS

Weston et al., "Molecular Cloning of a Fourth Member of a Human alpha(1,3)Fucosyltransferase Gene Family" 1992, J. Biol. Chem. 267(34):24575-24584.

Wishart et al., "A Single Mutation Converts a Novel Phosphotyrosine Binding Domain into a Dual-specificity Phosphatase" 1995, J. Biol. Chem. 270(45):26782-26785.

Zapata et al., "Sequence of the Cloned *Escherichia coli* K1 CMP-N-acetylneuraminic Acid Synthetase Gene" 1989, J. Biol. Chem. 264(25):14769-14774.

Xiao et al., "Catalysis of Thiol/Disulfide Exchange" 2005, J. Biol. Chem. 280(22):21099-21106.

Yamamoto et al., "Sugar-nucleotide Donor Specificity of Histo-blood Group A and B Transferases Is Based on Amino Acid Substitutions" 1990, J. Biol. Chem. 265(31):19257-19262.

Wen et al., "Primary Structure of GalBeta1,3(4) GlcNAc Alpha 2,3-Sialyltransferase Reveals a Conserved Region in the Sialyltransferase Family" 1992, FASEB Journal 6(1), A231. [abstract No. 1329].

Wen et al., "Primary Structure of GalBeta1,3(4)GlcNAcAlpha 2,3-Sialyltransferase Determined by Mass Spectrometry Sequence Analysis and Molecular Cloning" 1992, J. Biol. Chem. 267(29):21011-21019.

Taylor et al., 1991, Protein Immobilization Fundamentals and Applications, Manual.

Ten Hagen et al. "Characterization of a UDP-GalNAc:Polypeptide N-Acetylgalactosaminyltransferase That Displays Glycopeptide N-Acetylgalactosaminyltransferase Activity", 1999, J. Biol. Chem. 274(39):27867-27874.

Trottein et al., "Molecular cloning of a putative a3-fucosyltransferase from *Schistosoma mansoni*" 2000, Mol. Biochem. Parasitol. 107(2):279-287.

van Reis et al., "Industrial Scale Harvest of Proteins from Mammalism Cell Culture by Tangential Flow Filtration" 1991, Biotechnol. Bioeng. 38(4):413-422.

ATCC Catalog of Bacteria and Bacteriophages, 17th ed., 1989, p. 150.

Barrios et al., "Length of the antibody heavy chain complementarity determining region 3 as a specificity-determining factor" 2004, J. Mol. Recognit. 17(4):332-338.

Drucker et al. "Glucagon Gene Expression in Vertebrate Brain" J Biol Chem 263(27) pp. 13475-13478 (1988).

Song et al. "Reassembled Biosynthetic Pathway for a Large Scale Synthesis of CMP-Neu5Ac" Mar Drugs 1: 34-45 (2003).

Legault et al "Human alpha(1,3/1,4)-Fucosyltransferases Discriminate between Different Oligosaccharide Acceptor Substrates Through a Discrete Peptide Fragment." J Biol Chem 270(36): 20987-20996 (1995).

Vitetta et al. "Considering Therapeutic Antibodies" Science 313: 308-309 (2006).

Bhadra et al., "Pegnology: a review of PEG-ylated systems" 2002, Pharmazie 57(1):5-29.

Bocci, 1989, "Catabolism of therapeutic proteins and peptides with implications for drug delivery" Adv. Drug Deliv. Rev. 4(2):149-169.

Definition of Insect cells, p. 1 Accessed Apr. 14, 2009.

Kajihara et al., "Enzymatic synthesis of Kdn oligosaccharides by a bacterial a-(2-6)-sialyltransferase" 1999, Carbohydr Res. 315(1-2):137-141.

Kaneko et al., "Assignment of the human alpha 1,3-fucosyltransferase IX gene (FUT9) to chromosome band 6q16 by in situ hybridization" 1999, Cytogenet. Cell Genet. 86(3-4):329-330.

Hermanson, 1996, Bioconjugate Techniques, Academic Press, San Diego.

Herscovics et al., "Glycoprotein biosynthesis in yeast" 1993, FASEB J., 7(6):540-550.

Kaneko et al., "Alpha 1,3-Fucoslytransferase IX (Fuc-TIX) is very highly conserved between human and mouse; molecular cloning, characterization and tissue distribution of human Fuc-TIX" 1999, FEBS Lett. 452(3):237-242.

Leiter et al., "Purification, cDNA Cloning, and Expression of GDP-L-Fuc:Asn-linked GlcNAc a1,3-Fucosyltransferase from Mung Beans" 1999, J. Biol. Chem. 274(31):21830-21839.

Lewis et al., "Structure and Properties of Members of the hGH Family: A Review" 2000, Endocrine J. 47(suppl.):S1-S8.

Kobayashi et al., "Monoclonal antibody-dendrimer conjugates enable radiolabeling of antibody with markedly high specific activity with minimal loss of immunoreactivity" 2000, Eur. J. Nucl. Med. 27(9):1334-1339.

Kornfeld et al., "Assembly of Asparagine-Linked Oligosaccharides" 1985, Annu. Rev. Biochem. 54:631-664.

Kukowska-Latallo et al., "A cloned human cDNA determines expression of a mouse stage-specific embryonic antigen and the Lewis blood group (1,3/1,4)-fucosyltransferase" 1990, Genes Dev. 4(8):1288-1303.

Kukuruzinska et al., 1987, Proc. Natl. Acad. Sci. USA 84(8):2145-2149.

Kukuruzinska et al., "Protein glycosylation in yeast: Transcript heterogeneity of the ALG7 gene" 1987, Proc. Natl. Acad. Sci. USA 84(8):2145-2149.

Langer, "New Methods of Drug Delivery" 1990, Science 249(4976):1527-1533.

Gombotz et al "PEGylation: A Tool for Enhanced Protein Delivery," in Controlled Drug Delivery Park et al (eds) Chapter 12 pp. 110-123, ACS Symposium Series American Chemical Society, Washington DC (2000).

Ginns, PEG Glucocerebrosidase, Internet page from www.gaucher.org.uk/peg2.prg, printed Jun. 21, 2002.

Swiss-Prot Accession No. P25740 (May 1, 1992).

Strausberg et al. "Generation and initial analysis of more than 15,000 full-length human and mouse cDNA sequences" Proc Natl Acad Sci USA, 99(26): 16899-16903 (2002).

Paulson et al., "Purification of a sialyltransferase from bovine colostrum by affinity chromatography on CDP-agarose." 1977, J. Biol. Chem. 252(7):2356-2362.

Chang et al, "Analysis of Erythropoietin Glycoform Produced by Recombinant CHO Cells Using the Lectin-Blotting Technique." 1998, Biotechnol. Bioprocess Eng. 3(1):40-43.

Shao et al., "O-glycosylation of EGF repeats: identification and initial characterization of a UDP-glucose:protein O-glucosyltransferase" 2002, Glycobiology 12(11):763-770.

John et al., "The Structural Basis for Pyocin Resistance in *Neisseria gonorrhoeae* Lipooligosaccharides" 1991, J. Biol. Chem. 266(29):19303-19311.

Jonsson et al., "Phase variation of gonococcal pili by frameshift mutation in pilC, a novel gene for pilus assembly" 1991, EMBO J. 10(2):477-488.

Joziasse et al., "Purification and Enzymatic Characterizatioonf CMP-sialic Acid: Beta-Galactosyl1-3-N-Acetylgalactosaminide a2-3-Sialyltransferase from Human Placenta" 1985, J. Biol. Chem. 260(8):4941-4951.

Joziasse et al., "Bovine a1-3-Galactosyltransferase: Isolation and Characterization of a cDNA Clone" 1989, J. Biol. Chem. 264(24):14290-14297.

Kawai et al., "Structure of biologically active and inactive cerebrosides prepared from *Schizophyllum commune*" 1985, J. Lipid Res. 26(3):338-343.

Khidekel et al., "A Chemoenzymatic Approach toward the Rapid and Sensitive Detection of O-GlcNAc Posttranslational Modifications" 2003, J. Am. Chem. Soc. 125(52):16162-16163.

Prati et al. "Engineering of Coordinated Up- and Down-Regulation of Two Glycosyltransferases of the O-Glycosylation Pathway in Chinese Hamster Ovary (CHO) Cells" Biotech and Bioeng. 79(5): 580-585 (2002).

Uptima, Detergents: Solubilization of Biomolecules, Internet page from www.interchim.com/interchim/bio/produits_uptima/product_line/p1p_detergents.htm, 2001, Printed Nov. 14, 2011.

Dinter et al., "Glycosylation engineering in Chinese hamster ovary cells using tricistronic vectors" 2000, Biotechnol. Lett 22(1):25-30.

Dumas et al., "Enzymatic Synthesis of Sialyl Lex and Derivatives Based on a Recombinant Fucosyltransferase" 1991, Bioorg. Med. Chem. Lett. 1(8):425-428.

(56) References Cited

OTHER PUBLICATIONS

Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Edge et al., "Deglycosylation of Glycoproteins by Trifluoromethanesultonic" 1981, Anal. Biochem. 118(1):131-137.
Elhalabi et al. "Synthesis and Applications for Unnatural Sugar Nucleotides", 1999, Curr. Med. Chem. 6(2):93-116.
Fairhall et al., "Growth hormone (GH) binding protein and GH interactions in vivo in the guinea pig" 1992, Endocrinology 131(4):1963-1969.
Feldman et al., "Engineering N-linked protein glycosylation with diverse O antigen lipopolysaccharide structures in *Escherichia coli*" 2005, Proc. Natl. Acad. Sci. USA 102(8):3016-3021.
Kimura et al., "Reconstitution of functional L-selectin ligands on a cultured human endothelial cell line by cotransfection of a133 fucosyltransferase VII and newly cloned GlcNAcb:6-sulfotransferase cDNA" 1999, Proc. Natl. Acad. Sci. USA 96(8):4530-4535.
Gervais et al. "Glycosylation of human recombinant gonadotrophins: characterization and batch-to-batch consistency" Glycobiology 13(3): 179-189 (2003).
Hermanson et al., 1992, Immobilized Affinity Ligand Techniques, Academic Press.
Auge et al., "The Use of an Immobilised Cyclic Multi-Enzyme System to Synthesise Branched Penta- and Hexa-Saccharides Associated With Blood-Group I Epitopes" 1986, Carbohydr. Res. 151:147-156.
Auge et al., "The use of immobilised glycosyltransferases in the synthesis of sialyloligosaccharides" 1990, Carbohydr. Res. 200:257-268.
Ajisaka et al., "Efficient Synthesis of O-linked Glycopeptide by a transglycosylation Using Endo Alpha0N-Acetylgalactosaminidase from *Streptomyces* sp" 2001, Biosci. Biotechnol. Biochem. 65(5):1240-1243.
Genbank Accession No. U02304 (Mar. 8, 1994).
Genbank Accession No. U18918 (Oct. 1, 1995).
Gibson et al., "Investigation of the Structural Heterogeneity of Lipooligosaccharides from Pathogenic *Haemophilus* and *Neisseria* Species and of R-Type Lipopolysaccharides from *Salmonella typhimurium* by Electrospray Mass Spectrometry" 1993, J. Bacteriol. 175(9):2702-2712.
Gilbert, 1995, "Methods in Enzymology" Packer (ed.), Chapter 2, pp. 8-28, vol. 251, Biothiols Part A,Elsevier.
Gillespie et al., "Cloning of a Sialyltransferase involved in biosynthesis of 0-linked carbohydrate groups" 1990, FASEB Journal 4(7):A2068. [abstract No. 2173].
Gillespie et al., "Cloning and Expression of the Gal/31,3GalNAac2,3-Sialyltransferase" 1992, J. Biol. Chem. 267 (29):21004-21010.
Dudziak et al., "Cyclodextrin-assisted Glycan Chain Extension on a Protected Glycosyl Amino Acid" 2000, Tetrahedron 56(32):5865-5869.
Edano et al., "Importance of Sialic Acid in Recombinant Thrombomdulin in Terms of Pharmacokinetics and Separation of Desialyzed Glycoprotein" 1998, Biol. Pharm. Bull. 21(4):382-385.
Ellis, 1988, "Vaccines" Plotkin et al. (eds.), Chapter 29, W.B. Saunders Co., Philadelphia.
Gross et al., "Activation and transfer of novel synthetic 9-substituted sialic acids" 1987, Eur. J. Biochem. 168 (3):595-602.
Grundmann et al., "Complete cDNA sequence encoding human beta-galactoside ca-2,6-sialyltransferase" 1990, Nucleic Acids Res. 18(3):667.
Gu et al., "Purification and characterization of CMP-NeuAc:GM 1(Gal-beta1-4GalNAc) a2-3 sialyltransferase from rat brain" 1990, FEBS Lett. 275(1-2):83-86.
Guivisdalsky et al., "Synthesis and Antineoplastic Properties of Ether-Linked Thioglycolipids" 1990, J. Med. Chem. 33(9):2614-2621.
De Vries et al "Acceptor specificity of GDP-Fuc:Galpl->4GlcNAc-R a3-fucosyltransferase VI (FucTVI) expressed in insect cells as soluble, secreted enzyme" Glycobiology, 7(7) 921-927 (1997).

EMBL Accession No. U00039 (Jun. 2, 1994).
Dube et al. "Glycosylation at Specific Sites of Erythropoietin Is Essential for Biosynthesis Secretion and Biological Function" J Biol Chem 263(33): 17516-17521 (1988).
Ernst et al., "Substrate and donor specificity of glycosyltransferases" 1999, Glycoconj. J. 16(2):161-170.
Espuelas et al. "Synthesis of an Amphiphilic Tetraantennary Mannosyl Conjugate and Incorporation Into Liposome Carriers" Bioorg Med Chem Lett. 12(15): 2557-2560 (2003).
Perrin et al. "Common Physical Techniques Used in Purification," in Purification of Laboratory Chemicals, pp. 30-31, Pergamon (1980).
Tsunoda et al. "Enhanced Antitumor Potency of Polyethylene Glycolylated Tumor Necrosis Factor-a: A Novel Polymer-Conjugation Technique with a Reversible Amino-Protective Reagent" J Pharmcol Exp Ther. 209(1) 368-372 (1999).
Staudacher, "Alpha 1,3-Fucosyltransferases" 1996, Trends Glycosci. Glycotechnol. 8(44):391-408.
Stemmer, "Rapid Evolution of a Protein in vitro by DNA Shuffling" 1994, Nature 370(6488):389-391.
Stemmer, "DNA shuffling by random fragmentation and reassembly: In vitro recombination for molecular evolution" 1994, Proc. Natl. Acad. Sci. USA 91(22)10747-10751.
Zarling et al., "Mapping of Lymphocyte Surface Polypeptide Antigens by Chemical Cross-Linking with Bsocoes" 1980, J. Immunol. 124(2):913-920.
Andree et al., "Glucosyl Transferase Activity of Bovine Galactosyl Transferase" 1978, Biochim. Biophys. Acta 544(3):489-495.
Hällgren et al., "An Aminated GDP-Fucose Analog Useful in the Fucosyltransferase Catalyzed Addition of Biological Probes onto Oligosaccharide Chains" 1995, J. Carbohydr. Chem. 14(4-5):453-464.
Haro et al., "Glycoslated Human Growth Hormone (hGH): A Novel 24 kDa hGH-N Variant" 1996, Biochem. Biophys. Res. Comm. 228(2):549-556.
Harris (ed.), 1992, "Poly(Ethylene Glycol) Chemistry: Biotechnical and Biomedical Applications", Plenum Press, New York.
Ailor et al., Glycobiology, "N-glycan Patterns of Human Transferrin Produced in *Trichoplusia ni* Insect Cells: effects of Mammalian galactoslytransferase.", 2000, vol. 10, pp. 837-847.
Allegre et al., J. Membrane Science, "Cholesterol Removal by Nanofiltration: Applications in Nutraceutics and Nutritional Supplements." , 2006, vol. 269, pp. 109-117.
Altmann et al., Glycoconjugate Journal, "Insect Cells as hosts for the expression of recombinant glycoproteins.", 1999, vol. 16, pp. 109-123.
Aplin et al., CRC Critical Reviews in Biochemistry, "Preperation, Properties and Applications of Carbohydrate Conjugates of Proteins and Lipids.", 1981, vol. 10, No. 4, pp. 259-306.
Beauchamp et al., Analytical Biochemistry, "A New Procedure for the Synthesis of Polythylene Glycol-Protein Adducts; Effects on Function, Receptor Recognition and Clearance of Superoxide Dismutase, Lactoferrin and alpha2-Macroglobulin.", 1983, vol. 131, No. 1, pp. 25-33.
Bedard et al., Cytotechnology, "Maximization of Recombinant Protein Yield in the Insect cell/baculovirus system by one-time addition of nutrients to high-density batch cultures.", 1994, vol. 15, No. 1-3, pp. 129-138.
Bennett et al., FEBS, "A Novel Human UDP-N-Acetyl-D-Galactosamine: Polypeptide N-Acetylgalactosaminyltransferase, GalNAc-T7, with specificity for partial GalNAc-glycosylated acceptor substrates.", 1999, vol. 460, No. 2, pp. 226-230.
Bennett et al., Journal of Biological Chemistry, "Cloning of a Human UDP-N-Acetyl-D-Galactosamine: Polypeptide N-Acetylgalactosaminyltransferase That Complements other GalNAc Transferases in Complete O-Glycosylation of MUC1 Tandem Repeat", 1998, vol. 273, No. 46, pp. 30472-30481.
Berg-Fassman et al., Journal of Biological Chemistry, "Human Acid Beta-Glucosidase", 1993, vol. 268, No. 20, pp. 14861-14866.
Berger et al., Blood, "Preparation of Polythylene glycol-tissue plasminogen activator adducts that retain functional activity: characteristics and behavior in three animal species", 1988, vol. 71, No. 6, pp. 1641-1647.

(56) References Cited

OTHER PUBLICATIONS

Bhatia et al., Analytical Biochemistry, "Uses of Thiol-terminal Silanes and Heterobifunctional Crosslinkers for Immobilization of Antibodies on Silica Surfaces.", 1989, vol. 178, No. 2, pp. 408-413.
Bickel et al., Advanced Drug Delivery Reviews, "Delivery of Peptides and Proteins through the blood brain barrier.", 2001, vol. 46, No. 1-3, pp. 247-279.
Boime et al., Recent Prog. Horm. Res., "Glycoprotein Hormone Structure-Function and Analog Design", 1999, vol. 54, pp. 271-289.
Bjoern et al., Journal of Biological Chemistry, "Human Plasma and Recombinant Factor VII", 1991, vol. 266, No. 17, pp. 11051-11057.
Boccu et al., Z. Naturforsch, "Coupling of Monomethoxypolyethyleneglycois to Proteins via Active Esters.", 1983, vol. 38C, pp. 94-99.
Bishop et al.,"Both of beta-subunit carbohydrate residues of follicle-stimulating hormone determine the metabolic clearance rate and in vivo potency." Endocrinology, 1995, vol. 136, pp. 2635-2640.
Boissel et al., Journal of Biological Chemistry, "Erythropoietin Structure-Function Relationships.", 1993, vol. 268, No. 21, pp. 15983-15993.
Bork, Genome Research, "Powers and Pitfalls in Sequence Analysis: The 70% Hurdle", 2000, vol. 10, No. 4, pp. 398-400.
Bork et al., Trends in Genetics, "Go hunting in sequence databases but watch out for traps.", 1996, vol. 12, No. 10, pp. 425-427.
Bouizar et al., European Journal of Biochemistry, "Purification and Characterization of calcitonin receptors in rat kidney membranes by covalent cross-linking techniques.", 1986, vol. 155, No. 1, pp. 141-147.
Boyd et al., Molecular Immunology, "The Effect of the Removal of Sialic Acid, Galactose and Total Carbohydrate on the Functional Activity of Campath-1H.", 1995, vol. 32, No. 17-18, pp. 1311-1318.
Brenner, Trends in Genetics, "Errors in Genome Annotation", 1999, vol. 15, No. 4, pp. 132-133.
Browning et al., Journal of Immunology, "Studies on the differing effects of tumor necrosis factor and lymphotoxin on the growth of several human tumor lines.", 1989, vol. 143, No. 6, pp. 1859-1867.
Burns et al., Blood, "Purification and Characterization of the yeast-expressed erythropoietin mutant Epo (R103A), a specific inhibitor of human primary hematopoietic cell erythropoiesis.", 2002, vol. 99, No. 12, pp. 4400-4405.
Butnev et al., Biology of Reproduction, "Hormone-Specific Inhibitory Influence of Aplha-Subunit ASN Oligosccharide on In Vitro Subunit Association and Follicle-Stimulating Hormone Receptor Binding of Equine Gonadotropins.", 1998, vol. 58, No. 2, pp. 458-469.
Byun et al., ASAIO Journal, "Binding Kinetics of Thrombin and Antithrombin III with Immobilized Heparin Using a Spacer", 1992, vol. 23, No. 3, pp. M649-M653.
Bückmann et al., Angewandte Makromolekulare Chem, "Functionalization of Poly(ethylene glycol) and Monomethoxy-Poly(ethylene glycol)", 1981, vol. 182, No. 5, pp. 1379-1384.
Clark, R et al., The Journal of Biological Chemistry, "Long-Acting Growth Hormones . . . ", 1996, vol. 271, No. 36, pp. 21969-21977.
Casares et al., Nature Biotechnology (Continuation of Bio/Technology), "Antigen-specific downregulation of T cells by doxorubicin delivered through a recombinant MHC II-Peptide Chimera.", 2001, vol. 19, No. 2, pp. 142-147.
Chaffee et al., Journal of Clinical Investigation, "IgG Antibody Response to Polyethylene Glycol-modified Adenosine Deaminase in Patients with Adenosine Deaminase Deficiency", 1992, vol. 89, No. 5, pp. 1643-1651.
Charter et al., Glycobiology, "Biosynthetic incorporation of unnatural sialic acids into polysialic on neutral cells.", 2000, vol. 10, No. 10, pp. 1049-1056.
Chern et al., European Journal of Biochemistry, "Structural role of Amino Acids 99-110 in Recombinant Human Erythropoietin.", 1991, vol. 202, No. 2, pp. 225-229.
Chiba et al., Biochemical Journal, "Cloning and expression of the carboxypeptidase gene from *Aspergillus saitoi* and determination of the catalytic residues by site-directed mutagenesis", 1995, vol. 308, No. 2, pp. 405-409.
Chrisey et al., Nucleic Acids Research, "Covalent attachment of synthetic DNA to self-assembled monolayer films", 1996, vol. 24, No. 15, pp. 3031-3039.
Cointe et al., Glycobiology, "Unusual N-glycosylation of a recombinant human erythropoietin expressed in a human lymphoblastoid cell line does not alter its biological properties.", 2000, vol. 10, No. 5, pp. 511-519.
Conradt et al., Journal of Biological Chemistry, "Structure of the Carbohydrate Moiety of Human Interferon-Beta Secreted by a Recombinant Chinese Hamster Ovary Cell Line", 1987, vol. 262, No. 30, pp. 14600-14605.
Cope et al., Molecular Microbiology, "Molecular cloning of a gene involved in lipooligosaccharide biosynthesis and virulence expression by *Haemophilus influenzae* type B", 1991, vol. 5, No. 5, pp. 1113-1124.
Copeland, Robert A., Enzymes, "Chemical Mechanisms in Enzyme Catalysis", 2000, 2nd ed, pp. 146-150.
Crout et al., Current Opinion in Chemical Biology, "Glycosidases and Glycosyl Transferases in Glycoside and Oligosaccharide Synthesis", 1998, vol. 2, No. 1, pp. 98-111.
Delgado, C et al, Critial Reviews in Therapeutic Drug Carrier Systems, "The Uses and Properties of PEG-Linked Proteins", 1992, vol. 9, No. 3,4, pp. 249-304.
Durieux, P et al., Tetrahedron Letters., "Synthesis of Biotinylated Glycosulfopeptides Bychemoselective Ligation", 2001, vol. 42, No. 12, pp. 2297-2299.
Delgado et al., Biotechnology and Applied Biochemistry, "Coupling of Poly(ethylene glycol) to Albumin Under Very Mild Conditions by Activation with Tresyl Chloride: Characterization of the Conjugate by Partitioning in Aqueous Two-Phase Systems.", 1990, vol. 12, No. 2, pp. 119-128.
Doerks et al., Trends in Genetics, "Protein Annotation: Detective Work for Function Prediction", 1998, vol. 14, No. 6, pp. 248-250.
Douglas et al., Journal of the American Chemical Society, "Polymer-Supported Synthesis of Oligosaccharides", 1991, vol. 113, No. 13, pp. 5095-5097.
Dwek et al., J. Anat., "Glycobiology: The Function of Sugar in the IgG molecule", 1995, vol. 187, No. 2, pp. 279-292.
Eavarone et al., J. Biomed. Mater. Res., "Targeted Drug Delivery to C6 Glioma by Transferrin-Coupled Liposiomes", 2000, vol. 51, No. 1, pp. 10-14.
Ichikawa et al., "A Highly Efficient Multienzyme System for the One-Step Synthesis of a Sialyl Trisaccharide: In Situ Generation of Sialic Acid and N-Acetyllactosamine Coupled with Regeneration of UDP-Glucose, UDP-Galactose, and CMP-Sialic Acid" 1991, J. Am. Chem. Soc. 113(16):6300-6302.
Koike et al., "Total Synthesis of Sialosylcerebroside, GM4" 1987, Carbohydr. Res. 162(2):237-246.
Licari P. et al., Biotechnology and Bioengineering, "Production of a Discrete Heterogeneous Population of Beta-Galactosidase Polypeptides Using Baculovirus Expression Vectors", 1992, vol. 39, No. 9, pp. 932-944.
Liu et al., Chemistry—A European Journal, "A Paradigm Case for the Merging of Glycal and Enzymatic Assembly Methods in Glycoconjugate Synthesis: A Highly Efficient Chem-Enzymatic Synthesis of GM3", 1996, vol. 2, No. 11, pp. 1359-1362.
Long et al., Experimental Hematology, "Design of Homogeneous, Monopegylated erythropioetin analogs with preserved in vitro bioactivity", 2006, vol. 34, No. 6, pp. 697-704.
Lord et al., Clinical Cancer Research: Journal of the American Association, "Kinetics of Neutrophil Production in Normal and Neutropenic Animals during the Response to Filgrastim (r-metHu G-CSF) or Filgrastim SD/01 (PEG-r-metHu G-CSF)", 2001, vol. 7, No. 7, pp. 2085-2090.
Lougheed et al., Journal of Biological Chemistry, "Glycosyl Fluorides Can Function as Substrates for Nucleotide Phosphosugar-dependent Glycosyltransferases", 1999, vol. 274, No. 53, pp. 37717-37722.

(56) References Cited

OTHER PUBLICATIONS

Luckow et al., Current Opinion in Biotechnology, "Baculovirus systems for the expression of human gene products", 1993, vol. 4, No. 5, pp. 564-572.
Lund et al., Journal of Immunology, "Multiple Interactions of IgG with its core oligosaccharide can modulate recognition by complement and human Fc gamma receptor I and influence the synthesis of its oligosaccharide chains", 1996, vol. 157, No. 11, pp. 4963-4969.
Lund et al., The FASEB Journal, "Oligosaccharide-protein interactions in IgG can modulate recognition by Fc gamma receptors.", 1995, vol. 9, No. 1, pp. 115-119.
Mahal et al., Science, "Engineering Chemical Reactivity on Cell Surfaces Through Oligosaccharide Biosynthesis", 1997, vol. 276, No. 5315, pp. 1125-1128.
Maranga et al., Biotechnology and Bioengineering, "Virus Like Particle Production at Low Multiplicities of Infection With the Baculovirus Insect Cell System", 2003, vol. 84, No. 2, pp. 245-253.
Helling et al., "GD3 Vaccines for Melanoma: Superior Immunogenicity of Keyhole Limpet Hemocyanin Conjugate Vaccines" 1994, Cancer Res. 54(1):197-203.
Adelhorst et al. "Structure-Activity Studies of Glucagon-like Peptide-1" J. Biol. Chem. 269(9): 6275-6278 (1994).
Higa et al., "Sialylation of Glycoprotein Oligosaccharides with N-AcetylN-,Glycolyl-, and N-O-Diacetylneuraminic Acids" 1985, J. Biol. Chem. 260(15):8838-8849.
Leist et al. "Derivatives of Erythropoietin That Are Tissue Protective But Not Erythropoietic" Science 305: 239-242 (2004).
DeAngelis et al., "Immunochemical Confirmation of the Primary Structure of Streptococcal Hyaluronan Synthase and Synthesis of High Molecular Weight Product by the Recombinant Enzyme" 1994, Biochemistry 33(31):9033-9039.
DeLuca et al., "Enzymatic Synthesis of Hyaluronic Acid with Regeneration of Sugar Nucleotides" 1995, J. Am. Chem. Soc. 117(21):5869-5870.
Arslan et al "Mobilization of peripheral blood stem cells". Transf Apher Sci, 37: 179-185 (2007).
Dennis et al., "Albumin Binding as a General Strategy for Improving the Pharmacokinetics of Proteins" 2002, J. Biol. Chem. 277(38)35035-35043.
Dickinson et al., "Identification of surface residues mediating tissue factor binding and catalytic function of the serine protease factor VIIa" 1996, Proc. Natl. Acad. Sci. USA 93(25):14379-14384.
Dreyfus et al., "Successive Isolation and Separation of the Major Lipid Fractions Including Gangliosides from Single Biological Samples." 1997, Anal. Biochem. 249(1):67-78.
Broxmeyer et al. "Rapid mobilization of murine and human hematopoietic stem and progenitor cells with AMD3100, a CXCR4 antagonist" J Exp. Med. 201(8): 1307-1318 (2005).
Dudas et al., "Selection and Immunochemical Analysis of Lipooligosaccharide Mutants of *Neisseria gonorrhoeae*" 1988, Infect. Immun. 56(2):499-504.
Robertson et al., "The role of galE'm the biosynthesis and function of gonococcal lipopolysaccharide" 1993, Mol. Microbiol. 8(5):891-901.
Brumeanu et al. "Enzymatically mediated glycosidic conjugation of immunoglobulins with viral epitopes" J Immunol Meth. 183: 185-197 (1995).
Rosevear et al., "Synthesis and Solution Conformation of the Type 2 Blood Group Oligosaccharide AlphaLFuc-(1-2) BetaDGal(1-4)BetaDGlcNAc" 1982, Biochemistry 21(6):1421-1431.
Cantin et al. "Polyethylene Glycol Conjugation at Cys232 Prolongs the Half-Life of Alpha1 Proteinase Inhibitor" Am J Respir. Cell Mol. Biol. 27(6): 659-665 (2002).
Sadler et al., "Purification to homogeneity of a beta-galactoside alpha2 leads to 3 sialyltransferase and partial purification of an alpha-N-acetylgalactosaminide alpha2 leads to 6 sialyltransferase from porcine submaxillary glands." 1979, J. Biol. Chem. 254(11):4434-4442.
Sadler et al., "Purification to Homogeneity and Enzymatic Characterization of an cx-IV-Acetylgalactosaminide (x2+6 Sialyltransferase from Porcine Submaxillary Glands" 1979, J. Biol. Chem. 254(13):5934-5941.
Capoccia et al. "G-CSF andAMD3100 mobilize monocytes into the blood that stimulate angiogenesis in vivo through a paracrine mechanism" Blood 108(7): 2438-2445 (2006).
Cashen et al. "Mobilizing stem cells from normal donors: is it possible to improve upon G-CSF?" Bone Marrow Trans. 39: 577-588 (2007).
Sambrook et al., 1989, "Molecular Cloning: A Laboratory Manual" 2nd ed., Cold Spring Harbor Laboratory Press, Cold Spring Harbor, New York, p. 9.50-9.51.
EMBL Accession No. M80599 and M86935 (Jan. 23, 1992).
Deacon, "Therapeutic Strategies Based on Glucagon-Like Peptide 1" Diabetes 54: 2181-2189 (2004).
EMBL Accession No. S56361 (May 4, 1993).
Rathnam et al, "Conjugation of a Fetuin Glycopeptide to Human Follicle-Stimulating Hormone and Its Subunits by Photoactivation" Biochim Biophys Acta 624(2): 436-442 (1980).
Chang et al., "Engineered Recombinant Factor VII Q217 Variants with Altered Inhibitor Specificities" 1999, Biochemistry 38(34):10940-10948.
Broquet et al., "Substrate Specificity of Cerebral GDP-fucose : Glycoprotein Fucosyltransferase" 1982, Eur. J. Biochem. 123(1):9-13.
Hill et al. "Allogeneic Stem Cell Transplantation with Peripheral Blood Stem Cells Mobilized by Pegylated G-CSF" Biol. Blood Marrow Trans. 12: 603-607 (2006).
Burczak et al., "Characterization of a CMP-Sialic Acid: Lactosylceramide Sialyltransferase Activity in Cultured Hamster Cells" 1984, Biochim. Biophys. Acta 804(4):442-449.
Hu et al. "FGF-18, a Novel Member of the Fibroblast Growth Factor Family, Stimulates Hepatic and Intestinal Proliferation" Mol Cell Biol 18(10): 6063-6074 (1998).
Burns et al., "Selective Reduction of Disulfides by Tris(2-carboxyethyl)phosphine" 1991, J. Org. Chem. 56(8):2648-2650.
Hubei et al, "Clinical applications of granulocyte colony-stimulating factor: an update and summary" Ann Hematol 82: 207-213 (2003).
Clogston et al., "Glycosidase digestion, electrophoresis and chromatographic analysis of recombinant human granulocyte colony-stimulating factor glycoforms produced in Chinese hamster ovary cells" 1993, J. Chromatogr. A 637(1):55-62.
Jezek et al "Solid Phase Synthesis of Glycopeptide Dendrimers with Tn Antigenic Structure and their Biological Activities. Part I" J Peptide Sci, 5: 46-55 (1999).
Dabkowski et al., "Characterisation of a cDNA Clone Encoding the Pig alpha1,3 Galactosyltransferase: Implications for Xenotransplantation" 1993, Transplant Proc. 25(5):2921.
Higashi et al., "Conformation of Factor VIIa Stabilized by a Labile Disulfide Bond (Cys-310-Cys-329) in the Protease Domain Is Essential for Interaction with Tissue Factor" 1997, J. Biol. Chem. 272(41)25724-25730.
Flomenberg et al. "The use ofAMD3100 plus G-CSF for autologous hematopoietic progenitor cell mobilization is superior to G-CSF alone" Blood 106(5): 1867-1874 (2005).
High et al., "The role of a repetitive DNA motif (5*-CAAT-3') in the variable expression of the *Haemophilus influenzae* lipopolysaccharide epitope aGal(1-4)BetaGal" 1993, Mol. Microbiol. 9(6):1275-1282.
Francis et al "PEGylation of Cytokines and other therapeutic proteins and peptides: the importance of biological optimisation of coupling techniques." Intl J Hematol 68(1): 1-18 (1998).
DeFrees, Glycobiology, "GlycoPEGylation of Recombinant Therapeutic Proteins Produced in *Escherichia coli*", 2006, vol. 16, No. 9, pp. 833-843.
Detty et al., Journal of Organic Chemistry, "Telluropyrylium Dyes. 1. 2,6-Diphemyltelluropyrylium Dyes", 1982, vol. 47, pp. 5416-5418.
Saenko et al.,"Strategies towards a longer acting factor VIII" 2006, Haemophilia 12(suppl. 3):42-51.
E. Markovsky et al., "Administration, distribution, metabolism and elimination of polymer therapeutics", Journal of Controlled Release, Year 2012, vol. 161, pp. 446-460.

(56) References Cited

OTHER PUBLICATIONS

Mehvar R, "Modulation of the Pharmacokinetics and Pharmacodynamics of Proteins by Polyethylene Glycol Conjugation", J. Pharm. Pharmaceut. Sci., Year 2000, vol. 3, No. 1, pp. 125-136.

Ana I. Fernandes et al., "The effect of polysialylation on the immunogenicity and antigenicity of asparaginase: mplication its pharmacokinetics", International Journal of Pharmaceutics, year 2001, vol. 217, No. 1, pp. 215-224.

Jessica Y. Shu et al., "Peptide-Polymer Conjugates: From Fundamental Science to Application", Annual Review of Physical Chemistry, Year 2013, vol. 64, pp. 631-657.

R. Satchi et al., "PDEPT: polymer-directed enzyme prodrug therapy I.HPMA copolymer-cathepsin B and PK1 as a model combination", British Journal of Cancer, Year Sep. 28, 2001, vol. 85, No. 7, pp. 1070-1076.

Tian-Lu Cheng et al., "Poly(ethylene glycol) . modification of beta-glucuronidase-antibody conjugates for solid-tumor therapy by targeted activation of glucuronide prodrugs", Cancer Immunol. Immunother, Year 1997, vol. 44, pp. 305-315.

Yasuhiro Matsumura et al., "A new concept for macromolecular therapeutics in cancer chemotherapy: mechanism of tumoritropic accumulation of proteins and the antitumor agent smancs", Cancer Research., year Dec. 1986, vol No. 46 pp. 6387-6392.

Paul. A. Vasey et al., "Phase I clinical and pharmacokinetic study of PK1 [N-(2-hydroxypropyl)methacrylamide copolymer doxorubicin]: first member of a new class of chemotherapeutic agents-drug-polymer conjugates", Clinical. Cancer Research., Year Jan. 1999, vol. 5, No. 1, pp. 83-94.

Ruth Duncan, "The drawing era of polymer therapeutics", Nature. Review. Drug Discovery., Year May 2003, vol. 2, No. 5, pp. 347-360.

Polymeric Drugs and Drug Delivery Systems, edited by Richard L. Dunn and Raphael M. Ottenbrite, American Chemical Society, Year Aug. 15, 1991, pp. 3-23.

\* cited by examiner

FIGURE 2
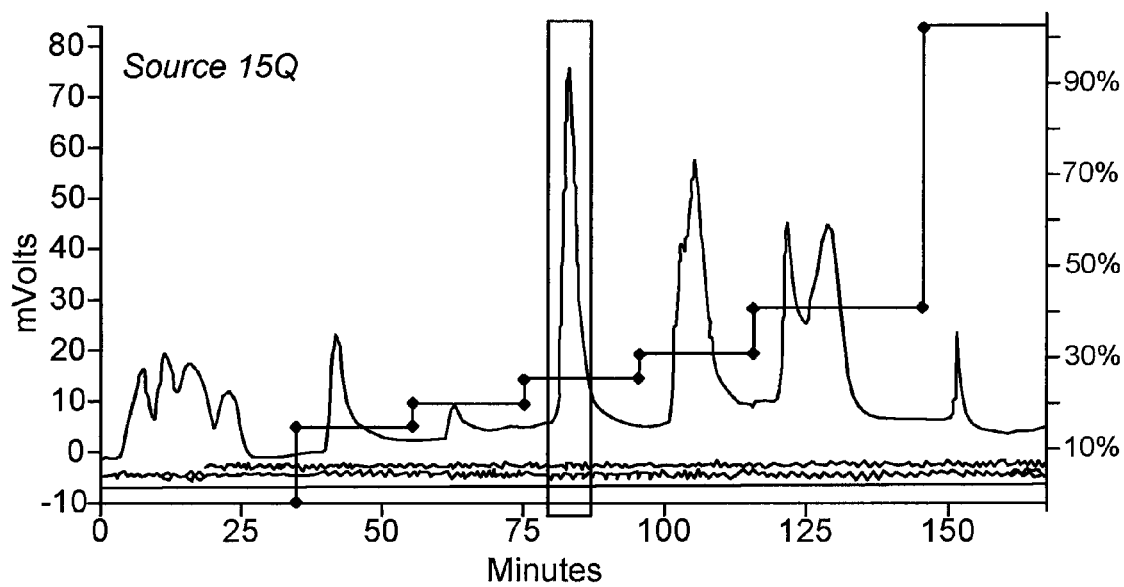
Product Fraction

FIGURE 3
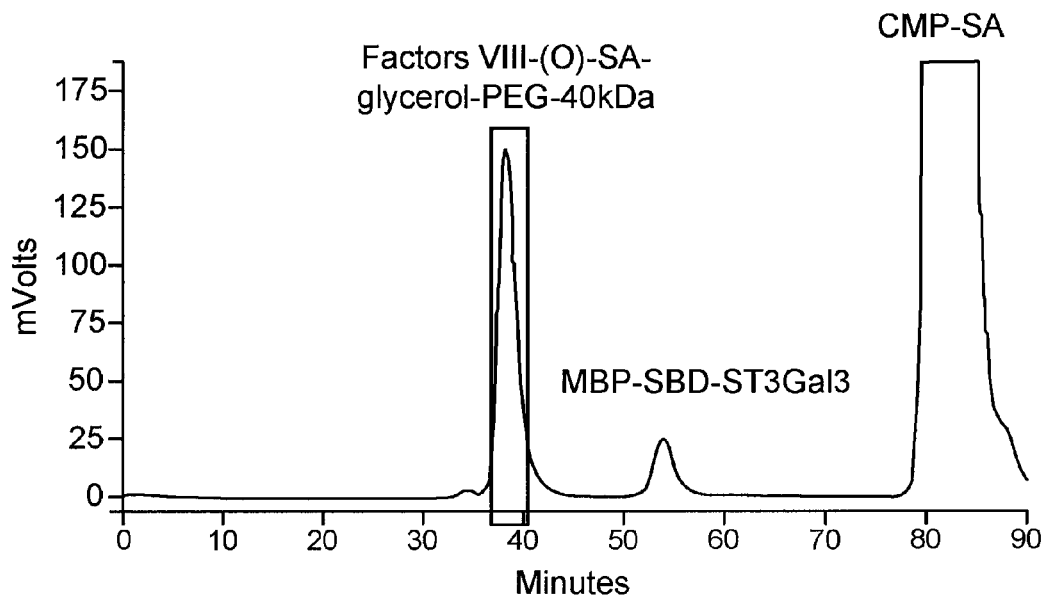
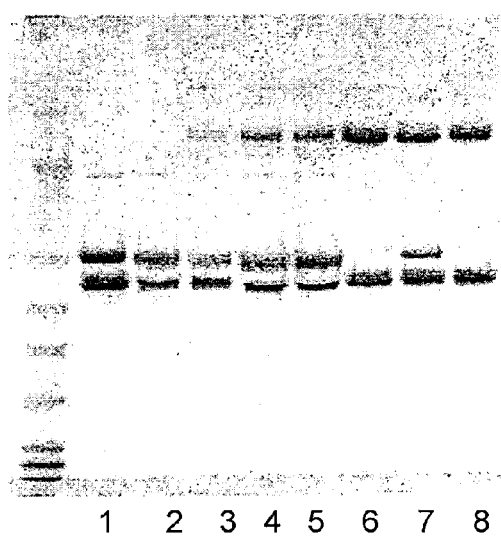
Lane 1; Factor VIII (concentrated)
Lane 2; GlycoPEGylation, 0hrs
Lane 3; GlycoPEGylation, 30hrs
Lane 4; GlycoPEGylatioin, 43hrs
Lane 5; GlycoPEGylation, 49hrs
Lane 6; Source 15Q Product
Lane 7; Capping Reaction (11 hrs)
Lane 8; Superdex 200 Purified Product n > 400 (eg ~ 455); n > 900 (eg ~ 910)

SEQUENCE LISTING

```
<160> NUMBER OF SEQ ID NOS: 3

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
```

```
                20                  25                  30
Arg Val Pro Lys Ser Phe Pro Phe Asn Thr Ser Val Val Tyr Lys Lys
                35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
                115                 120                 125

Phe Pro Gly Gly Ser His Thr Tyr Val Trp Gln Val Leu Lys Glu Asn
            130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445
```

```
Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
850                 855                 860
```

-continued

```
Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
    915                 920                 925

Leu Thr Glu Ser Gly Gly Pro Leu Ser Leu Ser Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
        980                 985                 990

Val Ser Ile Ser Leu Leu Lys Thr  Asn Lys Thr Ser Asn  Asn Ser Ala
    995                 1000                1005

Thr Asn  Arg Lys Thr His Ile  Asp Gly Pro Ser Leu  Leu Ile Glu
1010                1015                1020

Asn Ser  Pro Ser Val Trp Gln  Asn Ile Leu Glu Ser  Asp Thr Glu
1025                1030                1035

Phe Lys  Lys Val Thr Pro Leu  Ile His Asp Arg Met  Leu Met Asp
1040                1045                1050

Lys Asn  Ala Thr Ala Leu Arg  Leu Asn His Met Ser  Asn Lys Thr
1055                1060                1065

Thr Ser  Ser Lys Asn Met Glu  Met Val Gln Gln Lys  Lys Glu Gly
1070                1075                1080

Pro Ile  Pro Pro Asp Ala Gln  Asn Pro Asp Met Ser  Phe Phe Lys
1085                1090                1095

Met Leu  Phe Leu Pro Glu Ser  Ala Arg Trp Ile Gln  Arg Thr His
1100                1105                1110

Gly Lys  Asn Ser Leu Asn Ser  Gly Gln Gly Pro Ser  Pro Lys Gln
1115                1120                1125

Leu Val  Ser Leu Gly Pro Glu  Lys Ser Val Glu Gly  Gln Asn Phe
1130                1135                1140

Leu Ser  Glu Lys Asn Lys Val  Val Val Gly Lys Gly  Glu Phe Thr
1145                1150                1155

Lys Asp  Val Gly Leu Lys Glu  Met Val Phe Pro Ser  Ser Arg Asn
1160                1165                1170

Leu Phe  Leu Thr Asn Leu Asp  Asn Leu His Glu Asn  Asn Thr His
1175                1180                1185

Asn Gln  Glu Lys Lys Ile Gln  Glu Glu Ile Glu Lys  Lys Glu Thr
1190                1195                1200

Leu Ile  Gln Glu Asn Val Val  Leu Pro Gln Ile His  Thr Val Thr
1205                1210                1215

Gly Thr  Lys Asn Phe Met Lys  Asn Leu Phe Leu Leu  Ser Thr Arg
1220                1225                1230

Gln Asn  Val Glu Gly Ser Tyr  Asp Gly Ala Tyr Ala  Pro Val Leu
1235                1240                1245

Gln Asp  Phe Arg Ser Leu Asn  Asp Ser Thr Asn Arg  Thr Lys Lys
1250                1255                1260

His Thr  Ala His Phe Ser Lys  Lys Gly Glu Glu Glu  Asn Leu Glu
```

```
                    1265                1270                1275

Gly Leu Gly Asn Gln Thr Lys Gln Ile Val Glu Lys Tyr Ala Cys
                    1280                1285                1290

Thr Thr Arg Ile Ser Pro Asn Thr Ser Gln Gln Asn Phe Val Thr
                    1295                1300                1305

Gln Arg Ser Lys Arg Ala Leu Lys Gln Phe Arg Leu Pro Leu Glu
                    1310                1315                1320

Glu Thr Glu Leu Glu Lys Arg Ile Ile Val Asp Asp Thr Ser Thr
                    1325                1330                1335

Gln Trp Ser Lys Asn Met Lys His Leu Thr Pro Ser Thr Leu Thr
                    1340                1345                1350

Gln Ile Asp Tyr Asn Glu Lys Glu Lys Gly Ala Ile Thr Gln Ser
                    1355                1360                1365

Pro Leu Ser Asp Cys Leu Thr Arg Ser His Ser Ile Pro Gln Ala
                    1370                1375                1380

Asn Arg Ser Pro Leu Pro Ile Ala Lys Val Ser Ser Phe Pro Ser
                    1385                1390                1395

Ile Arg Pro Ile Tyr Leu Thr Arg Val Leu Phe Gln Asp Asn Ser
                    1400                1405                1410

Ser His Leu Pro Ala Ala Ser Tyr Arg Lys Lys Asp Ser Gly Val
                    1415                1420                1425

Gln Glu Ser Ser His Phe Leu Gln Gly Ala Lys Lys Asn Asn Leu
                    1430                1435                1440

Ser Leu Ala Ile Leu Thr Leu Glu Met Thr Gly Asp Gln Arg Glu
                    1445                1450                1455

Val Gly Ser Leu Gly Thr Ser Ala Thr Asn Ser Val Thr Tyr Lys
                    1460                1465                1470

Lys Val Glu Asn Thr Val Leu Pro Lys Pro Asp Leu Pro Lys Thr
                    1475                1480                1485

Ser Gly Lys Val Glu Leu Leu Pro Lys Val His Ile Tyr Gln Lys
                    1490                1495                1500

Asp Leu Phe Pro Thr Glu Thr Ser Asn Gly Ser Pro Gly His Leu
                    1505                1510                1515

Asp Leu Val Glu Gly Ser Leu Leu Gln Gly Thr Glu Gly Ala Ile
                    1520                1525                1530

Lys Trp Asn Glu Ala Asn Arg Pro Gly Lys Val Pro Phe Leu Arg
                    1535                1540                1545

Val Ala Thr Glu Ser Ser Ala Lys Thr Pro Ser Lys Leu Leu Asp
                    1550                1555                1560

Pro Leu Ala Trp Asp Asn His Tyr Gly Thr Gln Ile Pro Lys Glu
                    1565                1570                1575

Glu Trp Lys Ser Gln Glu Lys Ser Pro Glu Lys Thr Ala Phe Lys
                    1580                1585                1590

Lys Lys Asp Thr Ile Leu Ser Leu Asn Ala Cys Glu Ser Asn His
                    1595                1600                1605

Ala Ile Ala Ala Ile Asn Glu Gly Gln Asn Lys Pro Glu Ile Glu
                    1610                1615                1620

Val Thr Trp Ala Lys Gln Gly Arg Thr Glu Arg Leu Cys Ser Gln
                    1625                1630                1635

Asn Pro Pro Val Leu Lys Arg His Gln Arg Glu Ile Thr Arg Thr
                    1640                1645                1650

Thr Leu Gln Ser Asp Gln Glu Glu Ile Asp Tyr Asp Asp Thr Ile
                    1655                1660                1665
```

Ser Val Glu Met Lys Lys Glu Asp Phe Asp Ile Tyr Asp Glu Asp
1670             1675                 1680

Glu Asn Gln Ser Pro Arg Ser Phe Gln Lys Lys Thr Arg His Tyr
1685             1690                 1695

Phe Ile Ala Ala Val Glu Arg Leu Trp Asp Tyr Gly Met Ser Ser
1700             1705                 1710

Ser Pro His Val Leu Arg Asn Arg Ala Gln Ser Gly Ser Val Pro
1715             1720                 1725

Gln Phe Lys Lys Val Val Phe Gln Glu Phe Thr Asp Gly Ser Phe
1730             1735                 1740

Thr Gln Pro Leu Tyr Arg Gly Glu Leu Asn Glu His Leu Gly Leu
1745             1750                 1755

Leu Gly Pro Tyr Ile Arg Ala Glu Val Glu Asp Asn Ile Met Val
1760             1765                 1770

Thr Phe Arg Asn Gln Ala Ser Arg Pro Tyr Ser Phe Tyr Ser Ser
1775             1780                 1785

Leu Ile Ser Tyr Glu Glu Asp Gln Arg Gln Gly Ala Glu Pro Arg
1790             1795                 1800

Lys Asn Phe Val Lys Pro Asn Glu Thr Lys Thr Tyr Phe Trp Lys
1805             1810                 1815

Val Gln His His Met Ala Pro Thr Lys Asp Glu Phe Asp Cys Lys
1820             1825                 1830

Ala Trp Ala Tyr Phe Ser Asp Val Asp Leu Glu Lys Asp Val His
1835             1840                 1845

Ser Gly Leu Ile Gly Pro Leu Leu Val Cys His Thr Asn Thr Leu
1850             1855                 1860

Asn Pro Ala His Gly Arg Gln Val Thr Val Gln Glu Phe Ala Leu
1865             1870                 1875

Phe Phe Thr Ile Phe Asp Glu Thr Lys Ser Trp Tyr Phe Thr Glu
1880             1885                 1890

Asn Met Glu Arg Asn Cys Arg Ala Pro Cys Asn Ile Gln Met Glu
1895             1900                 1905

Asp Pro Thr Phe Lys Glu Asn Tyr Arg Phe His Ala Ile Asn Gly
1910             1915                 1920

Tyr Ile Met Asp Thr Leu Pro Gly Leu Val Met Ala Gln Asp Gln
1925             1930                 1935

Arg Ile Arg Trp Tyr Leu Leu Ser Met Gly Ser Asn Glu Asn Ile
1940             1945                 1950

His Ser Ile His Phe Ser Gly His Val Phe Thr Val Arg Lys Lys
1955             1960                 1965

Glu Glu Tyr Lys Met Ala Leu Tyr Asn Leu Tyr Pro Gly Val Phe
1970             1975                 1980

Glu Thr Val Glu Met Leu Pro Ser Lys Ala Gly Ile Trp Arg Val
1985             1990                 1995

Glu Cys Leu Ile Gly Glu His Leu His Ala Gly Met Ser Thr Leu
2000             2005                 2010

Phe Leu Val Tyr Ser Asn Lys Cys Gln Thr Pro Leu Gly Met Ala
2015             2020                 2025

Ser Gly His Ile Arg Asp Phe Gln Ile Thr Ala Ser Gly Gln Tyr
2030             2035                 2040

Gly Gln Trp Ala Pro Lys Leu Ala Arg Leu His Tyr Ser Gly Ser
2045             2050                 2055

```
Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 2
<211> LENGTH: 1445
<212> TYPE: PRT
<213> ORGANISM: Artificial Sequence
<220> FEATURE:
<223> OTHER INFORMATION: B-domain truncated human Factor VIII

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60
```

```
Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
```

-continued

```
            485                 490                 495
His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Gln Asn
            740                 745                 750

Pro Pro Val Leu Lys Arg His Gln Arg Glu Ile Thr Arg Thr Thr Leu
                755                 760                 765

Gln Ser Asp Gln Glu Glu Ile Asp Tyr Asp Asp Thr Ile Ser Val Glu
            770                 775                 780

Met Lys Lys Glu Asp Phe Asp Ile Tyr Asp Glu Asp Glu Asn Gln Ser
785                 790                 795                 800

Pro Arg Ser Phe Gln Lys Lys Thr Arg His Tyr Phe Ile Ala Ala Val
                805                 810                 815

Glu Arg Leu Trp Asp Tyr Gly Met Ser Ser Ser Pro His Val Leu Arg
            820                 825                 830

Asn Arg Ala Gln Ser Gly Ser Val Pro Gln Phe Lys Lys Val Val Phe
                835                 840                 845

Gln Glu Phe Thr Asp Gly Ser Phe Thr Gln Pro Leu Tyr Arg Gly Glu
            850                 855                 860

Leu Asn Glu His Leu Gly Leu Leu Gly Pro Tyr Ile Arg Ala Glu Val
865                 870                 875                 880

Glu Asp Asn Ile Met Val Thr Phe Arg Asn Gln Ala Ser Arg Pro Tyr
                885                 890                 895

Ser Phe Tyr Ser Ser Leu Ile Ser Tyr Glu Glu Asp Gln Arg Gln Gly
            900                 905                 910
```

```
Ala Glu Pro Arg Lys Asn Phe Val Lys Pro Asn Glu Thr Lys Thr Tyr
        915                 920                 925

Phe Trp Lys Val Gln His His Met Ala Pro Thr Lys Asp Glu Phe Asp
    930                 935                 940

Cys Lys Ala Trp Ala Tyr Phe Ser Asp Val Asp Leu Glu Lys Asp Val
945                 950                 955                 960

His Ser Gly Leu Ile Gly Pro Leu Leu Val Cys His Thr Asn Thr Leu
                965                 970                 975

Asn Pro Ala His Gly Arg Gln Val Thr Val Gln Glu Phe Ala Leu Phe
            980                 985                 990

Phe Thr Ile Phe Asp Glu Thr Lys Ser Trp Tyr Phe Thr Glu Asn Met
        995                 1000                1005

Glu Arg Asn Cys Arg Ala Pro Cys Asn Ile Gln Met Glu Asp Pro
    1010                1015                1020

Thr Phe Lys Glu Asn Tyr Arg Phe His Ala Ile Asn Gly Tyr Ile
    1025                1030                1035

Met Asp Thr Leu Pro Gly Leu Val Met Ala Gln Asp Gln Arg Ile
    1040                1045                1050

Arg Trp Tyr Leu Leu Ser Met Gly Ser Asn Glu Asn Ile His Ser
    1055                1060                1065

Ile His Phe Ser Gly His Val Phe Thr Val Arg Lys Lys Glu Glu
    1070                1075                1080

Tyr Lys Met Ala Leu Tyr Asn Leu Tyr Pro Gly Val Phe Glu Thr
    1085                1090                1095

Val Glu Met Leu Pro Ser Lys Ala Gly Ile Trp Arg Val Glu Cys
    1100                1105                1110

Leu Ile Gly Glu His Leu His Ala Gly Met Ser Thr Leu Phe Leu
    1115                1120                1125

Val Tyr Ser Asn Lys Cys Gln Thr Pro Leu Gly Met Ala Ser Gly
    1130                1135                1140

His Ile Arg Asp Phe Gln Ile Thr Ala Ser Gly Gln Tyr Gly Gln
    1145                1150                1155

Trp Ala Pro Lys Leu Ala Arg Leu His Tyr Ser Gly Ser Ile Asn
    1160                1165                1170

Ala Trp Ser Thr Lys Glu Pro Phe Ser Trp Ile Lys Val Asp Leu
    1175                1180                1185

Leu Ala Pro Met Ile Ile His Gly Ile Lys Thr Gln Gly Ala Arg
    1190                1195                1200

Gln Lys Phe Ser Ser Leu Tyr Ile Ser Gln Phe Ile Ile Met Tyr
    1205                1210                1215

Ser Leu Asp Gly Lys Lys Trp Gln Thr Tyr Arg Gly Asn Ser Thr
    1220                1225                1230

Gly Thr Leu Met Val Phe Phe Gly Asn Val Asp Ser Ser Gly Ile
    1235                1240                1245

Lys His Asn Ile Phe Asn Pro Pro Ile Ile Ala Arg Tyr Ile Arg
    1250                1255                1260

Leu His Pro Thr His Tyr Ser Ile Arg Ser Thr Leu Arg Met Glu
    1265                1270                1275

Leu Met Gly Cys Asp Leu Asn Ser Cys Ser Met Pro Leu Gly Met
    1280                1285                1290

Glu Ser Lys Ala Ile Ser Asp Ala Gln Ile Thr Ala Ser Ser Tyr
    1295                1300                1305
```

-continued

```
Phe Thr Asn Met Phe Ala Thr Trp Ser Pro Ser Lys Ala Arg Leu
    1310                1315                1320

His Leu Gln Gly Arg Ser Asn Ala Trp Arg Pro Gln Val Asn Asn
    1325                1330                1335

Pro Lys Glu Trp Leu Gln Val Asp Phe Gln Lys Thr Met Lys Val
    1340                1345                1350

Thr Gly Val Thr Thr Gln Gly Val Lys Ser Leu Leu Thr Ser Met
    1355                1360                1365

Tyr Val Lys Glu Phe Leu Ile Ser Ser Ser Gln Asp Gly His Gln
    1370                1375                1380

Trp Thr Leu Phe Phe Gln Asn Gly Lys Val Lys Val Phe Gln Gly
    1385                1390                1395

Asn Gln Asp Ser Phe Thr Pro Val Val Asn Ser Leu Asp Pro Pro
    1400                1405                1410

Leu Leu Thr Arg Tyr Leu Arg Ile His Pro Gln Ser Trp Val His
    1415                1420                1425

Gln Ile Ala Leu Arg Met Glu Val Leu Gly Cys Glu Ala Gln Asp
    1430                1435                1440

Leu Tyr
    1445

<210> SEQ ID NO 3
<211> LENGTH: 21
<212> TYPE: PRT
<213> ORGANISM: Artificial Sequence
<220> FEATURE:
<223> OTHER INFORMATION: Truncated B-domain of human factor VIII

<400> SEQUENCE: 3

Ser Phe Ser Gln Asn Ser Arg His Pro Ser Gln Asn Pro Pro Val Leu
1               5                   10                  15

Lys Arg His Gln Arg
            20
```

CONJUGATED FACTOR VIII MOLECULES

CROSS REFERENCE TO RELATED APPLICATIONS

This application is a continuation of U.S. patent application Ser. No. 12/597,473, filed Oct. 23, 2009, which is a 35 U.S.C. §371 national stage application of International Patent Application PCT/US2009/035339 (published as WO 2009/108806), filed Feb. 26, 2009; this application further claims priority under 35 U.S.C. §119 of U.S. Provisional Application 61/032,006, filed Feb. 27, 2008; the contents of all above-named applications are incorporated herein by reference.

FIELD OF THE INVENTION

The present invention relates to conjugated coagulation Factor VIII molecules. In particular, the present invention relates to conjugated Factor VIII molecules having a modified circulatory half life.

BACKGROUND OF THE INVENTION

Haemophilia A is an inherited bleeding disorder caused by deficiency or dysfunction of coagulation Factor VIII (FVIII) activity. The clinical manifestation is not on primary haemostasis—formation of the blood clot occurs normally—but the clot is unstable due to a lack of secondary thrombin formation. The disease is treated by intravenous injection of coagulation Factor FVIII which is either isolated from blood or produced recombinantly.

Current treatment recommendations are moving from traditional on-demand treatment towards prophylaxis. The circulatory half life of endogenous FVIII is 12-14 hours and prophylactic treatment is thus to be performed several times a week in order to obtain a virtually symptom-free life for the patients. IV administration is for many, especially children and young persons, associated with significant inconvenience and/or pain. There is thus a need in the art for novel Factor VIII products with Factor VIII activity that are preferably homogenous in structure, preferably safe and preferably having a significantly prolonged circulatory half life in order to reduce the number of Factor VIII administration per week. There is furthermore a need in the art for relatively simple methods for obtaining and producing such molecules.

PEGylation of Factor VIII in order to prolong circulatory half life is known in the art. It has however been an obstacle to obtain safe products having a homogenous structure as well as a significantly improved circulatory half life. The available methods of producing conjugated Factor VIII molecules are often laborious, and/or tend to result in low yields and/or products that are not homogenous in structure. The use of artificially engineered O-linked glycosylation sites for obtaining therapeutic proteins having a prolonged circulatory half life of therapeutic proteins has been suggested in WO2008011633, however, no conjugated Factor VIII molecules are disclosed therein.

SUMMARY OF THE INVENTION

In a first aspect, the present invention relates to a B domain truncated Factor VIII molecule with a modified circulatory half life, said molecule being covalently conjugated with a hydrophilic polymer via an O-linked oligosaccharide in the truncated B domain, wherein Factor VIII activation results in removal of the covalently conjugated side group.

In other aspects, the present invention furthermore relates to methods for obtaining such molecules, use of such molecules and pharmaceutical compositions comprising such molecules.

What is thus provided is a conjugated Factor VIII molecule with modified circulatory half life, wherein the conjugated side group (e.g. hydrophilic polymer) is removed upon activation. The molecules according to the invention are preferably homogenous in structure—at least with regard to position of the hydrophilic polymer in the truncated B-domain—and preferably have an advantageous safety profile. Likewise, relatively simple methods for obtaining such molecules are furthermore provided herein. Preferably, activated Factor VIII molecules according to the invention are similar to endogenous activated Factor VIII.

DETAILED DESCRIPTION OF THE INVENTION

Definitions

Factor VIII molecules: FVIII/Factor VIII is a large, complex glycoprotein that primarily is produced by hepatocytes. FVIII consists of 2351 amino acids, including signal peptide, and contains several distinct domains, as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

Endogenous Factor VIII molecules circulate in vivo as a pool of molecules with B domains of various sizes. What probably occurs in vivo is a gradual enzymatic removal of the B domain resulting in a pool of molecules with B-domains of various sizes. It is generally believed that cleavage at position 740, by which the last part of the B-domain is removed, occurs in connection with thrombin activation. However, it cannot be ruled out that a Factor VIII variant in which e.g. the cleavage site at position 740 has been impaired may be active.

"Factor VIII" or "FVIII" as used herein refers to a human plasma glycoprotein that is a member of the intrinsic coagulation pathway and is essential to blood coagulation. "Native FVIII" is the full length human FVIII molecule as shown in SEQ ID NO. 1 (amino acid 1-2332). The B-domain spans amino acids 741-1648 in SEQ ID NO 1.

```
SEQ ID NO 1:
ATRRYYLGAVELSWDYMQSDLGELPVDARFPPRVPKSFPFNTSVVYKKTLFVEFTDHLFNIA

KPRPPWMGLLGPTIQAEVYDTVVITLKNMASHPVSLHAVGVSYWKASEGAEYDDQTSQREK

EDDKVFPGGSHTYVWQVLKENGPMASDPLCLTYSYLSHVDLVKDLNSGLIGALLVCREGSL

AKEKTQTLHKFILLFAVFDEGKSWHSETKNSLMQDRDAASARAWPKMHTVNGYVNRSLPG
```

-continued

```
LIGCHRKSVYWHVIGMGTTPEVHSIFLEGHTFLVRNHRQASLEISPITFLTAQTLLMDLGQFLL

FCHISSHQHDGMEAYVKVDSCPEEPQLRMKNNEEAEDYDDDLTDSEMDVVRFDDDNSPSFI

QIRSVAKKHPKTWVHYIAAEEEDWDYAPLVLAPDDRSYKSQYLNNGPQRIGRKYKKVRFM

AYTDETFKTREAIQHESGILGPLLYGEVGDTLLIIFKNQASRPYNIYPHGITDVRPLYSRRLPKG

VKHLKDFPILPGEIFKYKWTVTVEDGPTKSDPRCLTRYYSSFVNMERDLASGLIGPLLICYKES

VDQRGNQIMSDKRNVILFSVFDENRSWYLTENIQRFLPNPAGVQLEDPEFQASNIMHSINGYV

FDSLQLSVCLHEVAYWYILSIGAQTDFLSVFFSGYTFKHKMVYEDTLTLFPFSGETVFMSMEN

PGLWILGCHNSDFRNRGMTALLKVSSCDKNTGDYYEDSYEDISAYLLSKNNAIEPRSFSQNSR

HPSTRQKQFNATTIPENDIEKTDPWFAHRTPMPKIQNVSSSDLLMLLRQSPTPHGLSLSDLQEA

KYETFSDDPSPGAIDSNNSLSEMTHFRPQLHHSGDMVFTPESGLQLRLNEKLGTTAATELKKL

DFKVSSTSNNLISTIPSDNLAAGTDNTSSLGPPSMPVHYDSQLDTTLFGKKSSPLTESGGPLSLS

EENNDSKLLESGLMNSQESSWGKNVSSTESGRLFKGKRAHGPALLTKDNALFKVSISLLKTN

KTSNNSATNRKTHIDGPSLLIENSPSVWQNILESDTEFKKVTPLIHDRMLMDKNATALRLNH

MSNKTTSSKNMEMVQQKKEGPIPPDAQNPDMSFFKMLFLPESARWIQRTHGKNSLNSGQGP

SPKQLVSLGPEKSVEGQNFLSEKNKVVVGKGEFTKDVGLKEMVFPSSRNLFLTNLDNLHENN

THNQEKKIQEEIEKKETLIQENVVLPQIHTVTGTKNFMKNLFLLSTRQNVEGSYDGAYAPVLQ

DFRSLNDSTNRTKKHTAHFSKKGEEENLEGLGNQTKQIVEKYACTTRISPNTSQQNFVTQRSK

RALKQFRLPLEETELEKRIIVDDTSTQWSKNMKHLTPSTLTQIDYNEKEKGAITQSPLSDCLTR

SHSIPQANRSPLPIAKVSSFPSIRPIYLTRVLFQDNSSHLPAASYRKKDSGVQESSHFLQGAKKN

NLSLAILTLEMTGDQREVGSLGTSATNSVTYKKVENTVLPKPDLPKTSGKVELLPKVHIYQK

DLFPTETSNGSPGHLDLVEGSLLQGTEGAIKWNEANRPGKVPFLRVATESSAKTPSKLLDPLA

WDNHYGTQIPKEEWKSQEKSPEKTAFKKKDTILSLNACESNHAIAAINEGQNKPEIEVTWAK

QGRTERLCSQNPPVLKRHQREITRTTLQSDQEEIDYDDTISVEMKKEDFDIYDEDENQSPRSFQ

KKTRHYFIAAVERLWDYGMSSSPHVLRNRAQSGSVPQFKKVVFQEFTDGSFTQPLYRGELNE

HLGLLGPYIRAEVEDNIMVTFRNQASRPYSFYSSLISYEEDQRQGAEPRKNFVKPNETKTYFW

KVQHHMAPTKDEFDCKAWAYFSDVDLEKDVHSGLIGPLLVCHTNTLNPAHGRQVTVQEFA

LFFTIFDETKSWYFTENMERNCRAPCNIQMEDPTFKENYRFHAINGYIMDTLPGLVMAQDQRI

RWYLLSMGSNENIHSIHFSGHVFTVRKKEEYKMALYNLYPGVFETVEMLPSKAGIWRVECLI

GEHLHAGMSTLFLVYSNKCQTPLGMASGHIRDFQITASGQYGQWAPKLARLHYSGSINAWS

TKEPFSWIKVDLLAPMIIHGIKTQGARQKFSSLYISQFIIMYSLDGKKWQTYRGNSTGTLMVFF

GNVDSSGIKHNIFNPPIIARYIRLHPTHYSIRSTLRMELMGCDLNSCSMPLGMESKAISDAQITA

SSYFTNMFATWSPSKARLHLQGRSNAWRPQVNNPKEWLQVDFQKTMKVTGVTTQGVKSLL

TSMYVKEFLISSSQDGHQWTLFFQNGKVKVFQGNQDSFTPVVNSLDPPLLTRYLRIHPQSWV

HQIALRMEVLGCEAQDLY
```

The Factor VIII molecules according to the present invention are B domain truncated Factor FVIII molecules wherein the remaining domains correspond to the sequence as set forth in amino acid no 1-740 and 1649-2332 in SEQ ID NO. 1. It follows that molecules according to the invention are recombinant molecules produced in transformed host cells, preferably of mammalian origin. However, the remaining domains (i.e. the three A-domains and the two C-domains) may differ slightly e.g. about 1%, 2%, 3%, 4% or 5% from the amino acid sequence as set forth in SEQ ID NO 1 (amino acids 1-740 and 1649-2332). In particular, it is plausible that amino acid modifications (substitutions, deletions, etc.) are introduced in the remaining domains e.g. in order to modify the binding capacity of Factor VIII with various other components such as e.g. vW factor, LPR, various receptors, other coagulation factors, cell surfaces, etc. Furthermore, it is plausible that the Factor VIII molecules according to the invention comprise other post-translational modifications in e.g. the truncated B-domain and/or in one or more of the other domains of the molecules. These other post-translational modifications may be in the form of various molecules conjugated to the Factor VIII molecule according to the invention such as e.g. polymeric compounds, peptidic compounds, fatty acid derived compounds, etc.

Factor VIII molecules according to the present invention, regardless of whether they are modified outside the B domain or not, have other posttranslational modifications or not, all have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. clot analysis, endogenous thrombin potential analysis, etc. Factor VIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

B domain: The B-domain in Factor VIII spans amino acids 741-1648 in SEQ ID NO 1. The B-domain is cleaved at several different sites, generating large heterogeneity in circulating plasma FVIII molecules. The exact function of the heavily glycosylated B-domain is unknown. What is known is that the domain is dispensable for FVIII activity in the coagulation cascade. This apparent lack of function is supported by the fact that B domain deleted/truncated FVIII appears to have in vivo properties identical to those seen for full length native FVIII. That being said there are indications that the B-domain may reduce the association with the cell membrane, at least under serum free conditions.

B domain truncated/deleted Factor VIII molecule: Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferable derived from the FVIII B-domain. The linker must comprise a recognition site for the protease that separates the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain.

The truncated B-domain may contain several O-glycosylation sites. However, according to a preferred embodiment, the molecule comprises only one, alternatively two, three or four O-linked oligosaccharides in the truncated B-domain.

According to a preferred embodiment, the truncated B domain comprises only one potential O-glycosylation site and the hydrophilic polymer is covalently conjugated to this O-glycosylation site.

The O-linked oligosaccharides in the B-domain truncated molecules according to the invention may be attached to O-glycosylation sites that were either artificially created by recombinant means and/or by exposure of "hidden" O-glycosylation sites by truncation of the B-domain. In both cases, such molecules may be made by designing a B-domain trunctated Factor VIII amino acid sequence and subsequently subjecting the amino acid sequence to an in silico analysis predicting the probability of O-glycosylation sites in the truncated B-domain. Molecules with a relatively high probability of having such glycosylation sites can be synthesized in a suitable host cell followed by analysis of the glycosylation pattern and subsequent selection of molecules having O-linked glycosylation in the truncated B-domain. Suitable host cells for producing recombinant Factor VIII protein are preferably of mammalian origin in order to ensure that the molecule is glycosylated. In practicing the present invention, the cells are mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk-ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk-ts13 BHK cell line is also available from the ATCC under accession number CRL 1632. A preferred CHO cell line is the CHO K1 cell line available from ATCC under accession number CC161 as well as cell lines CHO-DXB11 and CHO-DG44.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

The inventors of the present invention have thus shown that it is possible to activate "hidden" O-glycosylation sites in the Factor VIII B-domain by truncating the B-domain. While not wishing to be bound by any theory, this phenomenon could be attributable to the tertiary structure of the molecule in the truncated B-domain being altered. "Hidden" O-glycosylation sites are thus "made accessible" to glycosylation in the truncated B-domain. One advantage of this approach is the provision of recombinant molecules with an advantageous safety profile with respect to e.g. allergenicity. Another advantage could be that it may represent a simpler approach of obtaining B-domain truncated variants with an O-linked oligosaccharide in the B-domain due to the inherent abundance of glycosylation sites in the B-domain as it has previously proven difficult to engineer artificial O-glycosylation sites in recombinant proteins.

The length of the B domain in the wt FVIII molecule is about 907 amino acids. The length of the truncated B domain in molecules according to the present invention may vary from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B-domain may comprise fragments of the heavy chain and/or the light chain and/or an artificially introduced sequence that is not found in the wt FVIII molecule. The terms "B-domain truncated" and "B-domain deleted" may be used interchangeably herein.

Modified circulatory half life: Molecules according to the present invention have a modified circulatory half life compared to the wild type Factor VIII molecule, preferably an increased circulatory half life. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700% relative to the circulatory half life of the wild type FVIII.

Hydrophilic polymer: The modifying group/hydrophilic polymer according to the present invention is preferably non-naturally occurring. In one example, the "non-naturally occurring modifying group" is a polymeric modifying group, in which at least one polymeric moiety is non-naturally occurring. In another example, the non-naturally occurring modifying group is a modified carbohydrate. The locus of functionalization with the modifying group is selected such that it does not prevent the "modified sugar" from being added enzymatically to a polypeptide. "Modified sugar" also refers to any glycosyl mimetic moiety that is functionalized with a modifying group and which is a substrate for a natural or modified enzyme, such as a glycosyltransferase.

The polymeric modifying group added to a polypeptide can alter a property of such polypeptide, for example, its bioavailability, biological activity or its half-life in the body. Exemplary polymers according to the invention include water-soluble polymers that can be linear or branched and can include one or more independently selected polymeric moieties, such as poly(alkylene glycol) and derivatives thereof. The polymeric modifying group according to the invention may include a water-soluble polymer, e.g. poly(ethylene glycol) and derivatives thereof (PEG, m-PEG), poly(propylene glycol) and derivatives thereof (PPG, m-PPG) and the like.

The term "water-soluble" refers to moieties that have some detectable degree of solubility in water. Methods to detect and/or quantify water solubility are well known in the art. Exemplary water-soluble polymers according to the invention include peptides, saccharides, poly(ethers), poly (amines), poly(carboxylic acids) and the like. Peptides can have mixed sequences and be composed of a single amino acid, e.g., poly(lysine). An exemplary polysaccharide is poly (sialic acid). An exemplary poly(ether) is poly(ethylene glycol), e.g., m-PEG. Poly(ethylene imine) is an exemplary polyamine, and poly(acrylic) acid is a representative poly (carboxylic acid).

The polymer backbone of the water-soluble polymer according to the invention can be poly(ethylene glycol) (i.e. PEG). The term PEG in connection with the present invention includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine or cysteine. In one example, the branched poly(ethylene glycol) can be represented in general form as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

FIG. 8 shows a representative branched PEG polymer of use in embodiments of the invention, referred to herein as "SA-glycerol-PEG." FIG. 8A shows an exemplary SA-glycerol-PEG component of CMP-SA-glycerol-PEG or of a SA-glycerol-PEG linked to a glycan or an amino acid of a polypeptide. FIG. 8B shows the SA-glycerol-PEG moiety linked to a glycan or polypeptide through a Gal residue. FIG. 8C shows the SA-glycerol-PEG moiety linked to a glycan or polypeptide through a Gal-GalNAc residue. FIG. 8D shows the SA-glycerol-PEG moiety linked to an amino acid of a polypeptide through a Gal-GalNAc moiety. In various embodiments, AA is threonine or serine. In an exemplary embodiment, AA is converted to an O-linked glycosylation site by deletion of the B-domain of the FVIII polypeptide. The discussion regarding the molecular weight of the polymer hereinbelow is generally applicable to the branched PEG shown in FIG. 8. In FIG. 8, the index "n" represents any integer providing a linear (and thus a branched) m-PEG of the desired molecular weight as discussed. In various embodiments, "n" is selected such that the linear m-PEG moiety is about 20 KDa to about 40 KDa, for example, about 20 KDa, about 30 KDa or about 40 KDa. Integers corresponding to these m-PEG molecular weights correspond to about 400 (e.g. about 455) to about 900 (e.g. about 910). Accordingly, "n" is selected to provide a branched PEG that is about 40 KDa to about 80 KDa, e.g., about 40 KDa, about 50 KDa, about 60 KDa, about 70 KDa, or about 80 KDa.

Many other polymers are also suitable for the invention. Polymer backbones that are non-peptidic and water-soluble, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly ([alpha]-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof.

Although the molecular weight of each chain of the polymer backbone can vary, it is typically in the range of from about 100 Da to about 160,000 Da, such as e.g., from about 5,000 Da to about 100,000 Da. More specifically, the size of each conjugated hydrophilic polymer according to the present invention may vary from about 500 Da to about 80,000 Da, such as e.g. about 1000 Da to about 80,000 Da; about 2000 Da to about 70,000 Da; about 5000 to about 70,000 Da; about 5000 to about 60,000 Da; about 10,000 to about 70,000 Da; about 20,000 to about 60,000 Da; about 30,000 to about 60,000 Da; about 30,000 to about 50,000 Da; or about 30,000 to about 40,000 Da. It should be understood that these sizes represent estimates rather than exact measures. According to a preferred embodiment, the molecules according to the invention are conjugated with a heterogeneous population of hydrophilic polymers, such as e.g. PEG of a size of e.g. 10,000, 40,000, or 80,000 Da+/−about 5000, about 4000, about 3000, about 2000, or about 1000 Da.

O-linked oligosaccharide: Both N-glycans and O-glycans are attached to proteins by the cells producing the protein. The cellular N-glycosylation machinery recognizes and glycosylates N-glycosylation signals (N—X—S/T motifs) in the amino acid chain, as the nascent protein is translocated from the ribosome to the endoplasmic reticulum (Kiely et al. 1976; Glabe et al. 1980).

Likewise, O-glycans are attached to specific O-glycosylation sites in the amino acid chain, but the motifs triggering O-glycosylation are much more heterogeneous than the N-glycosylation signals, and our ability to predict O-glycosylation sites in amino acid sequences is still inadequate (Julenius et al. 2004). The construction of artificial O-glycosylation sites it is thus associated with some uncertainty. The general assumption is that the native FVIII molecule does not contain any O-glycosylation sites, and the skilled man would therefore expect that at least one artificial O-glycosylation site would have to be constructed and inserted into the B domain in connection with practicing the present invention.

The O-linked oligosaccharide in a truncated Factor VIII B domain may thus be covalently linked to a naturally occurring O-linked glycosylation sequence or an O-linked glycosylation sequence which has been artificially constructed by recombinant techniques.

According to a preferred embodiment of the present invention, the O-linked oligosaccharide is linked to a naturally occurring O-linked glycosylation sequence which is not exposed to glycosylation in the wild type Factor VIII molecule but is becoming accessible to O-glycosylation as a consequence of truncation of the B domain. An example thereof is shown in the examples and in SEQ ID NO 2 (the truncated B-domain corresponds to amino acids 742-763). It is plausible that the "hidden" O-glycosylation site in SEQ ID NO 2 will also become glycosylated even if the B-domain is truncated at a somewhat different place, i.e. if the truncated B domain is somewhat shorter (e.g. 1, 2, 3, 4, or 5 amino acids shorter than SEQ ID NO 2) or longer (such as e.g. 1, 2, 3, 4, 5, 6, 7, 8, 9, 10, 15, 20, 25, 30, 35, 40, 45, or 50 amino acids) compared to SEQ ID NO 2. This approach by activating a "hidden" O-glycosylation site by truncation of a B-domain rather than creation of an artificial O-glycosylation site has the advantage of creating a molecule with an advantageous safety profile (i.e. reduced allergenicity, etc.). Other O-glycosylation sites in the Factor VIII B-domain may likewise become activated by truncating the molecules in different ways.

Glyco-PEGylation of O-linked oligosaccharide: The biosynthesis of O-glycans can be modified and terminated with the addition of sialic acid residues relatively early in biosynthesis. Certain sialyltransferase enzymes are capable of acting on GalNAcα-Ser/Thr, or early O-glycan core subtypes after Core 1 GalT action. The term T antigen is associated with the presence of the Galβ1-3GalNAcα-Ser/Thr disaccharide. Production of these structures involves a competition among glycosyltransferases for the same substrate and thus the expression levels and subcellular distributions of glycosyltransferases within the Golgi apparatus determines the structural outcome in O-glycan biosynthesis and diversification. As illustrated in FIG. 1, only the Galβ1-3GalNAcα-Ser/Thr disaccharide is amenable for glycoPEGylation.

However, the available amount of this structure may be greatly enhanced through treatment of the protein with sialidase or Core1 GalT or a combination thereof. As a result of the glycoPEGylation process the Sialic acid PEG is added to the native structure through an α3 bond to the Galβ1-3GalNAcα-Ser/Thr disaccharide of the target protein (FIG. 1).

Other hydrophilic polymers can also be attached to O-linked oligosaccharides. The basic requirement for enzymatically conjugating other hydrophilic polymers to FVIII via the O-glycan is the ability to couple them to the glycyl-Sialic acid derivative via the free amino group as disclosed in WO03031464. This may be achieved through a large variety of coupling chemistries known to those skilled in the art. Examples of activated biocompatible polymer includes polyalkylene oxides such as without limitation polyethylene glycol (PEG), 2-(methacryloyloxy)ethyl phosphorylcholine (mPC) polymers (as described in WO03062290), dextrans, colominic acids or other carbohydrate based polymers, polymers of amino acids or of specific peptides sequences, biotin derivatives, polyvinyl alcohol (PVA), polycarboxylates, polyvinylpyrrolidone, polyethylene-co-maleic acid anhydride, polystyrene-co-malic acid anhydride, polyoxazoline, poly-acryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof.

Pharmaceutical composition: A pharmaceutical composition is herein preferably meant to encompass compositions comprising Factor VIII molecules according to the present invention suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the FVIII compound in the form of a nasal or pulmonal spray. As a still further option, the pharmaceutical compositions containing the FVIII compound of the invention may also be adapted to transdermal administration, e.g. by needle-free injection or from a patch, optionally an iontophoretic patch, or transmucosal, e.g. buccal, administration.

In a first aspect the present invention thus relates to a B-domain truncated Factor VIII molecule with a modified circulatory half life, said molecule being covalently conjugated with a hydrophilic polymer via an O-linked oligosaccharide in the truncated B domain, wherein Factor VIII activation (activation of the molecule) results in removal of the covalently conjugated hydrophilic polymer.

According to one embodiment, the hydrophilic polymer is PEG. The size of the PEG polymer may vary from about 10,000 to about 160,000 Da; such as 10,000 to 80,000 Da, such as e.g. about 10,000; 15,000, 20,000; 25,000; 30,000; 35,000; 40,000; 45,000; 50,000; 55,000; 60,000; 65,000; 70,000; 75,000; or 80,000 Da. Preferably, the O-linked oligosaccharide is attached to an O-glycosylation site that is made by truncation of the B-domain and not by inserting an artificial O-glycosylation site that is not found in the wt FVIII molecule.

According to a particularly preferred embodiment, the molecule according to the present invention comprises the amino acid sequence as set forth in SEQ ID NO 2. Such molecules have a unique feature in that the activated FVIII molecule is identical to the native active FVIII molecule. This feature appears to have advantageous properties in safety assessments.

The present invention also relates to pharmaceutical compositions comprising molecules according to the present invention.

The present invention furthermore relates to a method of obtaining a molecule according to the present invention, wherein said method comprises conjugating a B-domain truncated Factor VIII molecule with a hydrophilic polymer, such as e.g. a PEG group, via an O-linked oligosaccharide in the truncated B domain. It follows that the present invention also relates to molecules obtained by or obtainable by such methods.

In another aspect, the present invention relates to a method of treatment of a haemophilic disease comprising administering to a patient in need thereof a therapeutically effective amount of a molecule according to the invention.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In yet another aspect, the present invention relates to use of a molecule according to the invention as a medicament as well as use of a molecule according to the invention for manufacture of a medicament for treatment of haemophilia.

In a final aspect, the present invention relates to a method of engineering a B-domain truncated Factor VIII molecule according to the present invention, said method comprising (i) truncating the B-domain and optionally subjecting the amino acid sequence of this truncated Factor VIII molecule to an analysis identifying potential O-linked glycosylation sites, (ii) producing the molecule in a suitable host cell and (iii) selecting molecules having O-linked glycans in the truncated B-domain.

BRIEF DESCRIPTION OF THE DRAWINGS

In the figures, the size of the conjugated groups is sometimes referred to as "K", which is herein meant to be equivalent to KDa (kilo Dalton).

FIG. 2: Ion-exchange chromatography of the reaction mixture on Source 15Q (A). SDS-PAGE with molecular markers (left) of collected fraction (B).

FIG. 3: Purification of the capped product on superdex 200 size-exclusion chromatography.

FIG. 8 shows a representative branched PEG polymer of use in embodiments of the invention, referred to herein as "SA-glycerol-PEG. " FIG. 8A shows an exemplary SA-glycerol-PEG component of CMP-SA-glycerol-PEG or of a SA-glycerol-PEG linked to a glycan or an amino acid of a polypeptide. FIG. 8B shows the SA-glycerol-PEG moiety linked to a glycan or polypeptide through a Gal residue. FIG. 8C shows the SA-glycerol-PEG moiety linked to a glycan or polypeptide through a Gal-GalNAc residue. FIG. 8D shows the SA-glycerol-PEG moiety linked to an amino acid of a polypeptide through a Gal-GalNAc moiety.

EXAMPLES

Example 1

Figure 1:
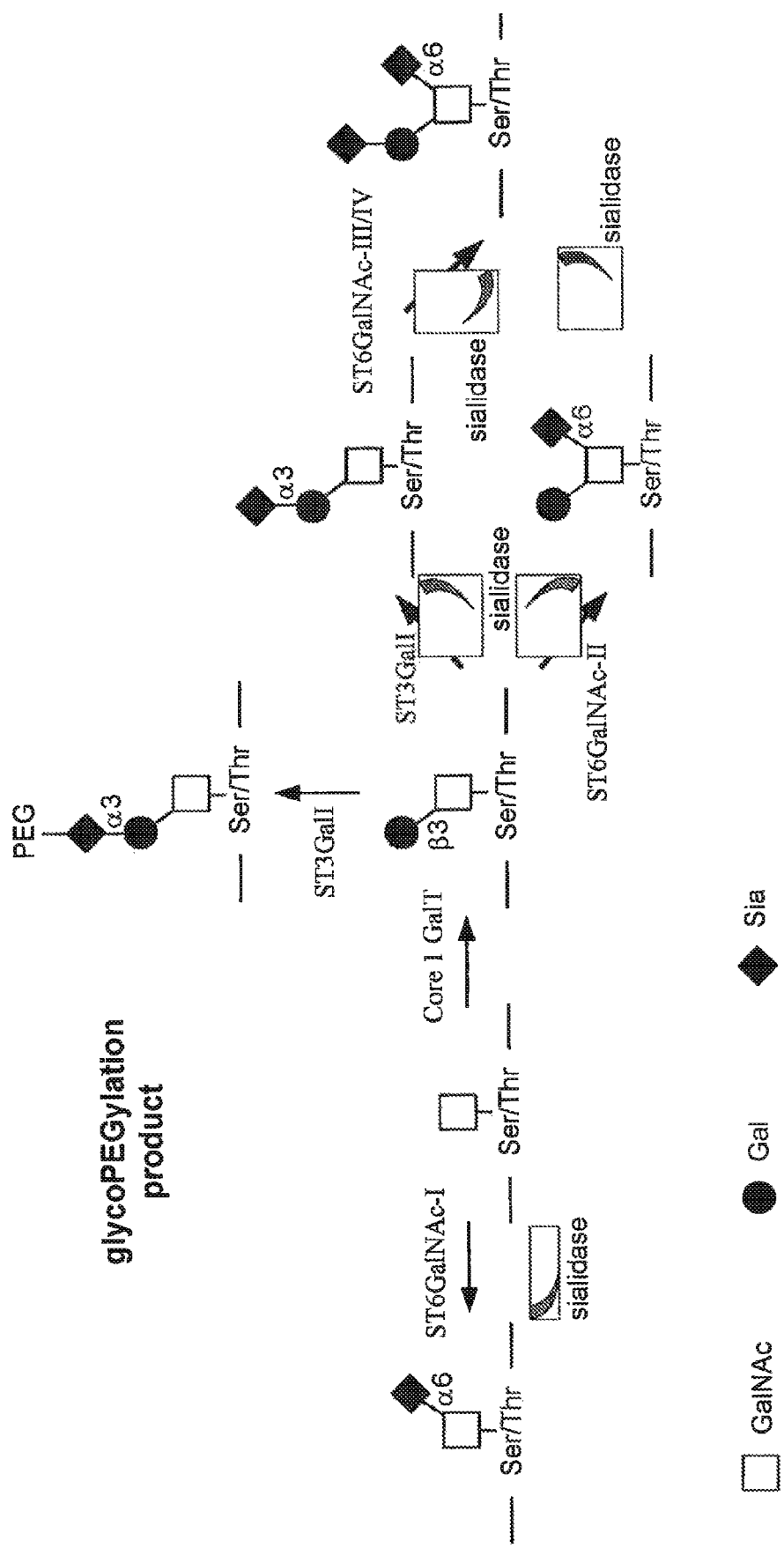
FIG. 1: Schematic drawing of glycol PEGylation process of O-linked oligosaccharides. The figure does not represent an exhaustive list of possible ways to arrive at the products obtained in the examples.

Production of Recombinant B Domain Truncated O-glycosylated Factor VIII

An example of the amino acid sequence of a B-domain deleted Factor VIII molecule is given in SEQ ID NO 2. This polypeptide may also be referred to as "N8". This molecule comprises a 21 amino acid residue linker sequence (SFSQN-SRHPSQNPPVLKRHQR (SEQ ID NO 3)—the underlined S is the Serine residue with the O-glygan that is pegylated in Example 2).

Factor VIII molecules according to the present invention may in the Examples be referred to in various ways—but all references to Factor VIII molecules refer to Factor VIII molecules according to the invention, or alternatively Factor VIII molecules in the process of being converted to Factor VIII molecules according to the invention.

SEQ ID NO 2:
ATRRYYLGAVELSWDYMQSDLGELPVDARFPPRVPKSFPFNTSVVYKKTLFVEFTDHLFNIA

KPRPPWMGLLGPTIQAEVYDTVVITLKNMASHPVSLHAVGVSYWKASEGAEYDDQTSQREK

EDDKVFPGGSHTYVWQVLKENGPMASDPLCLTYSYLSHVDLVKDLNSGLIGALLVCREGSL

AKEKTQTLHKFILLFAVFDEGKSWHSETKNSLMQDRDAASARAWPKMHTVNGYVNRSLPG

LIGCHRKSVYWHVIGMGTTPEVHSIFLEGHTFLVRNHRQASLEISPITFLTAQTLLMDLGQFLL

FCHISSHQHDGMEAYVKVDSCPEEPQLRMKNNEEAEDYDDDLTDSEMDVVRFDDDNSPSFI

QIRSVAKKHPKTWVHYIAAEEEDWDYAPLVLAPDDRSYKSQYLNNGPQRIGRKYKKVRFM

AYTDETFKTREAIQHESGILGPLLYGEVGDTLLIIFKNQASRPYNIYPHGITDVRPLYSRRLPKG

VKHLKDFPILPGEIFKYKWTVTVEDGPTKSDPRCLTRYYSSFVNMERDLASGLIGPLLICYKES

VDQRGNQIMSDKRNVILFSVFDENRSWYLTENIQRFLPNPAGVQLEDPEFQASNIMHSINGYV

FDSLQLSVCLHEVAYWYILSIGAQTDFLSVFFSGYTFKHKMVYEDTLTLFPFSGETVFMSMEN

PGLWILGCHNSDFRNRGMTALLKVSSCDKNTGDYYEDSYEDISAYLLSKNNAIEPRSFSQNSR

HPSQNPPVLKRHQREITRTTLQSDQEEIDYDDTISVEMKKEDFDIYDEDENQSPRSFQKKTRH

YFIAAVERLWDYGMSSSPHVLRNRAQSGSVPQFKKVVFQEFTDGSFTQPLYRGELNEHLGLL

GPYIRAEVEDNIMVTFRNQASRPYSFYSSLISYEEDQRQGAEPRKNFVKPNETKTYFWKVQH

HMAPTKDEFDCKAWAYFSDVDLEKDVHSGLIGPLLVCHTNTLNPAHGRQVTVQEFALFFTIF

DETKSWYFTENMERNCRAPCNIQMEDPTFKENYRFHAINGYIMDTLPGLVMAQDQRIRWYL

LSMGSNENIHSIHFSGHVFTVRKKEEYKMALYNLYPGVFETVEMLPSKAGIWRVECLIGEHL

HAGMSTLFLVYSNKCQTPLGMASGHIRDFQITASGQYGQWAPKLARLHYSGSINAWSTKEPF

SWIKVDLLAPMIIHGIKTQGARQKFSSLYISQFIIMYSLDGKKWQTYRGNSTGTLMVFFGNVD

SSGIKHNIFNPPIIARYIRLHPTHYSIRSTLRMELMGCDLNSCSMPLGMESKAISDAQITASSYFT

NMFATWSPSKARLHLQGRSNAWRPQVNNPKEWLQVDFQKTMKVTGVTTQGVKSLLTSMY

VKEFLISSSQDGHQWTLFFQNGKVKVFQGNQDSFTPVVNSLDPPLLTRYLRIHPQSWVHQIAL

RMEVLGCEAQDLY

Cell Line and Culture Process:

Using Factor VIII cDNA a mammalian expression plasmid encoding B-domain deleted Factor VIII having an amino acid sequence as set forth in SEQ ID NO 2 was constructed. The plasmid is encoding Factor VIII heavy chain comprising amino acid 1-740 of full length human Factor VIII and Factor VIII light chain comprising amino acid 1649-2332 of full length human Factor VIII. The heavy and light chain sequences are connected by a 21 amino acid linker with the sequence of amino acid 741-750 and 1638-1648 of full length human Factor VIII. Chinese hamster ovary (CHO) cells were transfected with the BDD Factor VIII coding plasmid and selected with the dihydrofolate reductase system eventually leading to a clonal suspension producer cell cultivated in animal component-free medium.

The first step in the process is the inoculation of a cell vial, from a working cell bank vial, into a chemically defined and animal component free growth medium. Initially after thawing, the cells are incubated in a T-flask. One or two days after thawing, the cells are transferred to a shaker flask, and the culture volume is expanded by successive dilutions in order to keep the cell density between $0.2$-$3.0 \times 10^6$ cells/ml. The next step is the transfer of the shaker flask culture into seed bioreactors. The culture volume is here further expanded before the final transfer to the production bioreactor. The same chemically defined and animal component free medium is used for all the inoculum expansion steps. After transfer to the production bioreactor, the medium is supplemented with components that increase the product concentration. In the production bioreactor the cells are cultured in a repeated batch process with a cycle time of three days. At harvest, 80-90% of the culture volume is transferred to a harvest tank. The remaining culture fluid is then diluted with fresh medium, in order to obtain the initial cell density, and then a new growth period is initiated.

The harvest batch is clarified by centrifugation and filtration and transferred to a holding tank before initiation of the purification process. A buffer is added to the cell free harvest in the holding tank to stabilise pH.

By the end of the production run, cells are collected and frozen down, in order to make an end of production cell bank. This cell bank is tested for mycoplasma, sterility and viral contamination.

Purification:

For the isolation of B-domain-deleted Factor VIII from cell culture media, a four step purification procedure was used including a concentration step on a Capto MMC column, an immunoabsorbent chromatography step, an anionic exchange chromatography and finally a gelfiltration step. Typically the following procedure was used: 11 liter of sterile filtered medium was pumped onto at column (1.6×12 cm) of Capto MMC (GE Healthcare, Sweden) equilibrated in buffer A: 20 mM imidazole, 10 mM CaCl$_2$, 50 mM NaCl, 0.02% Tween 80, pH=7.5 at a flow of 15 ml/min. The column was washed with 75 ml of buffer A followed by wash with 75 ml of buffer A containing 1.5 M NaCl. The protein was eluted with 20 mM imidazole, 10 mM CaCl$_2$, 0.02% Tween 80, 2.5 M NaCl, 8 M ethyleneglycol, pH=7.5 at a flow of 1 ml/min. Fractions of 8 ml were collected and assayed for Factor VIII activity (CoA-test). Factor VIII containing fractions were pooled and normally a pool volume of around 50 ml was obtained.

A monoclonal antibody against Factor VIII has been developed (Kjalke Eur J Biochem 234 773). By epitope mapping (results not shown) this antibody, F25, was found to recognise the far C-terminal sequence of the heavy chain from amino acid residue 725 to 740. The F25 antibody was coupled to NHS-activated Sepharose 4 FF (GE Healthcare, Bio-Sciences AB, Uppsala, Sweden) at a density of 2.4 mg per ml of gel essentially as described by the manufacturer. The pool from the previous step was diluted 10 times with 20 mM imidazole, 10 mM CaCl$_2$, 0.02% Tween 80, pH=7.3 and applied to the F25 Sepharose column (1.6×9.5 cm) equilibrated with 20 mM imidazole, 10 mM CaCl$_2$, 150 mM NaCl, 0.02% Tween 80, 1 M glycerol pH=7.3 at a flow of 0.5 ml/min. The column was washed with equilibration buffer until the UV signal was constant and then with 20 mM imidazole, 10 mM CaCl$_2$, 0.65 M NaCl, pH=7.3 until the UV signal was constant again. Factor VIII was eluted with 20 mM imidazole, 10 mM CaCl$_2$, 0.02% Tween 80, 2.5 M NaCl, 50% ethyleneglycol, pH=7.3 at a flow of 1 ml/min. Fractions of 1 ml were collected and assayed for Factor VIII activity (CoA-test). Factor VIII containing fractions were pooled and normally a pool volume of around 25 ml was obtained.

A buffer A: 20 mM imidazole, 10 mM CaCl$_2$, 0.02% Tween 80, 1 M glycerol, pH=7.3 and a buffer B: 20 mM imidazole, 10 mM CaCl$_2$, 0.02% Tween 80, 1 M glycerol, 1 M NaCl, pH=7.3 was prepared for the ion-exchange step. A column (1×10 cm) of Macro-Prep 25Q Support (Bio-Rad Laboratories, Hercules, Calif., USA) was equilibrated with 85% buffer A/15% Buffer B at a flow of 2 ml/min. The pool from the previous step was diluted 10 times with buffer A and pumped onto the column with a flow of 2 ml/min. The column was washed with 85% buffer A/15% buffer B at a flow of 2 ml/min and Factor VIII was eluted with a linear gradient from 15% buffer B to 70% buffer B over 120 ml at a flow of 2 ml/min. Fractions of 2 ml were collected and assayed for Factor VIII activity (CoA-test). Factor VIII containing fractions were pooled and normally a pool volume of around 36 ml was obtained.

The pool from the previous step was applied to a Superdex 200, prep grade (GE Healthcare, Bio-Sciences AB, Uppsala, Sweden) column (2.6×60 cm) equilibrated and eluted at 1 ml/min with 20 mM imidazole, 10 mM CaCl$_2$, 0.02% Tween 80, 1 M glycerol, 150 mM NaCl, pH=7.3. Fractions of 3 ml were collected and assayed for Factor VIII activity (CoA-test). Factor VIII containing fractions were pooled and normally a pool volume of around 57 ml was obtained. The pool containing Factor VIII was store at −80° C.

With the use of the above four-step purification procedure an overall yield of approximately 15% was obtained as judged by CoA activity and ELISA measurements.

The cell line used for manufacture of N8 is a recombinant Chinese hamster ovary (CHO) cell line stably transfected with expression plasmid #814 F8-500 in pTSV7 consisting of the pTSV7 expression vector with an insert containing cDNA encoding the F8-500 protein. "N8" is herein meant to correspond to a protein having an amino acid sequence as listed in SEQ ID NO 2. Starting at the N-terminus, the F8-500 protein (N8) consists of the FVIII signal peptide (amino acids −19 to −1) followed by the FVIII heavy chain without the B domain (amino acids 1-740), a 21 amino acid linker (SFSQN-SRHPSQNPPVLKRHQR), and the FVIII light chain (amino acids 1649-2332 of wild-type human FVIII). The sequence of the 21 amino acid linker is derived from the FVIII B domain and consists of amino acids 741-750 and 1638-1648 of full length FVIII.

CHO cells were transfected with 814 F8-500 in pTSV7 and selected with the dihydrofolate reductase system eventually leading to a clonal suspension producer cell cultivated in animal component-free medium. A production run is initiated by thawing a working cell bank vial and expanding the cells until transfer to a production bioreactor. The same chemically defined and animal component free medium is used for all the inoculum expansion steps. After transfer to the production bioreactor, the medium is supplemented with components that increase the product concentration. In the production bioreactor the cells are cultured in a repeated batch process with a cycle time of three days. At harvest, 80-90% of the culture volume is transferred to a harvest tank. The remaining culture fluid is then diluted with fresh medium, in order to obtain the initial cell density, and then a new growth period is initiated. The harvest batch is clarified by centrifugation and filtration and transferred to a holding tank before initiation of the purification process. A buffer is added to the cell free harvest in the holding tank to stabilize pH.

Example 2

PEGylation of Recombinant B Domain Truncated and O-Glycosylated Factor VIII

The recombinant Factor VIII molecules obtained in Example 1 are conjugated with polyethylenglycol (PEG) using the following procedure:

For the glycoPEGylation of the recombinant Factor VIII molecules obtained in Example 1 to be efficient a FVIII concentration >5 mg/ml is preferred. Since FVIII is not normally soluble at the concentration a screening of selected buffer compositions was conducted (see some of these results in table 1).

Based on these considerations, a buffer containing 50 mM MES, 50 mM CaCl$_2$, 150 mM NaCl, 20% glycerol, pH 6.0 was found to be a suitable reaction buffer.

TABLE 1

Evaluation of impact of reaction conditions on FVIII solubility and aggregation.

| Reaction buffer composition | Precipitate | % Aggregate |
| --- | --- | --- |
| 10 mM Histidine, 260 mM Glycine, 1% Sucrose, 10 mM CaCl2 | YES | n.d. |
| 50 mM HEPES, 10 mM CaCl2, 150 mM NaCl, pH 7; | YES | n.d. |
| 50 mM MES, 10 mM CaCl2, 150 mM NaCl, pH 6.0 | YES | n.d. |
| 50 mM MES, 50 mM CaCl2, 150 mM NaCl, pH 6.0 | NO | 8 |
| 50 mM MES, 50 mM CaCl2, 150 mM NaCl, 10% glycerol, pH 6.0 | NO | 5 |
| 50 mM MES, 50 mM CaCl2, 150 mM NaCl, 20% glycerol, pH 6.0 | NO | 1.0-1.7 |

Recombinant FVIII which had been purified as described above was concentrated in reaction buffer either by ion exchange on a Poros 50 HQ column using step elution, on a Sartorius Vivaspin (PES) filter, 10 kDa cut-off or on an Amicon 10 kDa MWCO PES filter to a concentration of 6-10 mg/mL. The glycoPEGylation of FVIII was initiated by mixing Factor VIII (BDD) (~4.7 mg/mL final) with Sialidase (*A. urifaciens*) (159 mU/mL), CMP-SA-glycerol-PEG-40 kDa (5 mol.eq.) and MBP-ST3Gal1 (540 mU) in reaction buffer (50 mM MES, 50 mM CaCl$_2$, 150 mM NaCl, 20% glycerol, 0.5 mM antipain, pH 6.0). The reaction mixture was incubated at 32° C. until a conversion yield of ~20-30% of total.

Following the incubation the sample was diluted with Buffer A (25 mM Tris, 5 mM CaCl$_2$, 20 mM NaCl, 20% glycerol, pH 7.5) and applied onto a Source 15Q column (1 cm id×6 cm, 4.7 mL, 1 mL/min, 280 nm). The bound material was washed with Buffer A and eluted using a step gradient with Buffer B (25 mM Tris, 5 mM CaCl$_2$, 1 M NaCl, 20% glycerol, pH 7.5). GlycoPEGylated Factor VIII-(O)-SA-glycerol-PEG-40 kDa was eluted from the column at ~25% Buffer B. FIG. 2 shows ion-exchange chromatography of the reaction mixture on Source 15Q.

In order to block free galactose moieties which had been exposed on the N-glycans during the sialidase treatment the pooled fraction of Factor VIII-SA-glycerol-PEG-40 kDa (1.0 mg/mL final) was mixed with CMP-SA (2,000 mol eq) and MBP-SBD-ST3Gal3 (400 mU/mL) in reaction buffer 50 mM MES, 20 mM CaCl$_2$, 150 mM NaCl, 10 mM MnCl$_2$, 20% glycerol, pH 6.0 and incubated at 32° C. for 11 hours.

The resulting capped, glycoPEGylated Factor VIII-SA-glycerol-PEG-40 kDa was separated from CMP-SA and ST3GalIII by gel-filtration on a Superdex 200 column (10 cm id×300 mm; 280 nm) equilibrated with 50 mM MES, 50 mM CaCl$_2$, 150 mM NaCl, 10% glycerol, pH 6.0; flow rate of 0.25 mL/min. The product Factor VIII-SA-glycerol-PEG-40 kDa elutes at 38 min. FIG. 3 shows purification of the capped product using Superdex 200 size-exclusion chromatography. The peak fraction was collected, aliquoted and subjected to subsequent analysis.

The purpose of the capping procedure is to reduce in vivo clearance of the conjugated Factor VIII molecule.

Example 3

Activity of O-glycan PEGylated rFVIII in Chromogenic FVIII Activity Assay

The activity of the O-glycoPEGylated rFVIII obtained in Example 2 was evaluated in a chromogenic FVIII assay using Coatest SP reagents (Chromogenix) as follows: rFVIII samples and calibrator (the 7th international FVIII standard from NIBSC) were diluted in Coatest assay buffer (50 mM Tris, 150 mM NaCl, 1% BSA, pH 7.3, with preservative). Fifty µl of samples, standards, and buffer negative control were added to 96-well microtiter plates (Nunc) in duplicates. The Factor IXa/Factor X reagent, the phospholipid reagent and CaCl$_2$ from the Coatest SP kit were mixed 5:1:3 (vol:vol:vol) and 75 µl of this added to the wells. After 15 min incubation at room temperature 50 µl of the Factor Xa substrate S-2765/thrombin inhibitor I-2581 mix was added and the reactions incubated 10 min at room temperature before 25 µl 1 M citric acid, pH 3, was added. The absorbance at 415 nm was measured on a Spectramax microtiter plate reader (Molecular Devices) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by size exclusion HPLC by integrating the light chain peak in the HPLC chromatogram, i.e. the PEG-moiety was not included. The data in table 2 demonstrate that the specific chromogenic activity was maintained for the O-glycoPEGylated rFVIII compounds, meaning that Factor VIII activity appear to be retained in the PEGylated variants.

TABLE 2

Specific chromogenic activity of O-glycoPEGylated rFVIII with different PEG group sizes.

| rFVIII compound | Specific chromogenic activity (IU/mg) |
| --- | --- |
| rFVIII | 11819 ± 727 (5) |
| 10KDa-PEG-[O]-rFVIII | Approx 8331 (1) |
| 40KDa-PEG-[O]-rFVIII | 9760 ± 886 (8) |
| 80KDa-PEG-[O]-rFVIII | 12129 ± 2643 (3) |

Data are mean and standard deviations of the numbers of independent determinations noted in parentheses Example 4

Activity of O-glycan PEGylated rFVIII in FVIII Clotting Activity Assay

The activity of the O-glycoPEGylated rFVIII was further evaluated in FVIII clotting assay. rFVIII samples were diluted in HBS/BSA (20 mM hepes, 150 mM NaCl, pH 7.4 with 1% BSA) to approximately 10 U/ml followed by 10-fold dilution in FVIII-deficient plasma containing VWF (Dade Behring). The samples and a calibrated plasma standard (HemosIL Calibration Plasma from Instrumentation Laboratory) were subsequently diluted in HBS/BSA to four (samples) or six (calibrator) different concentrations. The clotting time was measured on an ACL9000 instrument (Instrumentation laboratory) using the single factor program, where samples/standards were mixed with equal volumes of FVIII-deficient plasma with VWF (Dade Behring), calcium and aPTT reagents, and the clotting time measured. As reagents the following were used: Synthasil (HemosIL, Instrumentation Laboratory), Actin FS (Activated PTT Reagent, Dade Behring) Stago (STA® PTT-A, Stago), and dAPPTin (DAPPTIN®TC, Technoclone). The activities of the samples were calculated based on a semi-log plot of clotting time versus concentration of the calibrator.

The clotting activity (FIG. 4) of the O-glycoPEGyated rFVIII compounds (control, 10, 40, and 80 kDA PEG, respectively) was decreased to various extend depending on the PEG size and the aPTT reagents used. Using Synthasil or dAPPTin as aPTT reagents resulted in a gradual decrease in clotting activity with PEG-size. With Stago's aPTT reagent, a 50% lower specific clotting activity was observed for all three O-glycoPEGylated N8 compounds evaluated. When Actin FS was used as aPTT reagent a specific clotting activity around 10,000 IU/mg was maintained. The data indicates that the aPTT assay is influenced by the presence of a PEG moiety, however, using a selected aPTT reagents e.g. Actin FS the specific clotting activity of rFVIII is not impaired upon O-glycoPEGylation.

Example 5

Effect of O-Linked PEGylation of rFVIII on Co-Factor Activity and Rate of FVIII Activation Incorporation of activated FVIII into the FIXa-FVIIIa complex enhances the catalytic efficiency of FIXa-catalyzed FX activation five orders of magnitude (van Dieij en et al. (1981) *J Biol Chem* 256:3433) and characterization of FIXa-FVIIIa complex assembly and FX activation kinetics is a sensitive measure of the functional integrity of FVIIIa molecules. The co-factor activity of thrombin-activated rFVIII or PEG-rFVIII was characterized by determining the kinetic parameters of FIXa-catalyzed FX activation in the presence of phospholipids and thrombin-activated rFVIII or PEG-rFVIII. Using the FVIIIa activity assay (FIXa-cofactor activity assay), reciprocal titrations of FIXa and FVIIIa against a fixed concentration (0.1 nM) of rFVIIIa or FIXa, respectively, were performed to obtain apparent affinity of FIXa for rFVIIIa ($K_{1/2FIXa}$) and functional FVIIIa concentration. The Michaelis constant ($k_m$) and turn-over number ($k_{cat}$) of FX activation were obtained from titrations of FX against a fixed concentration of FIXa-FVIIIa complex.

The FIXa-cofactor activity assays was carried out as follows: Thrombin-activated rFVIII and PEG-rFVIII variants were prepared freshly for each test by incubating rFVIII (usually 0.7 nM, 1 U/mL) with 5 nM human α-thrombin for exactly 30 seconds at 37° C. Subsequently, the rate of FX activation was quantified by subsampling the activation reaction above into a prepared mixture of FIXa, phospholipid vesicles (Phospholipid TGT from Rossix [Mölndal, Sweden]), hirudin, Pefabloc Xa and $CaCl_2$; FX activation was initiated by addition of FX and allowed to proceed for either 30 seconds or 60 seconds at 37° C. Activation was stopped by dilution of the FX activation reaction into ice cold buffer containing EDTA. Using a FXa specific chromogenic substrate, the concentration of FXa was quantified by reading absorbance at 405 nM in an ELISA reader. A reference curve prepared using purified FXa was used to convert absorbance to FXa concentration. The turn-over number of FIXa-rFVIIIa complexes assembled from activated rFVIII or PEG-rFVIII variants was used to convert the rate of FX activation to rFVIIIa concentration.

The rate of thrombin-catalyzed rFVIII activation was measured by quantifying the initial (0 to 3 min) formation of rFVIIIa in a mixture containing 0.7 nM rFVIII or PEG-rFVIII and 0.13 nM human α-thrombin. Formation of FVIIIa was linear in time. The rate of FVIIIa activation was expressed as moles rFVIIIa formed per minute per mole of rFVIII initially present ($v/[rFVIII]_0$).

O-linked glycoPEGylation of rFVIII did not affect the rate of thrombin-catalyzed rFVIII activation or the $k_m$ or $k_{cat}$ of FIXa-catalyzed activation of FX in the presence of activated rFVIII (see Table 3). Furthermore, O-linked glycoPEGylation did not affect the apparent $K_d$ of rFVIIIa-FIXa interaction ($K_{1/2FIXa}$).

Figure 4A:
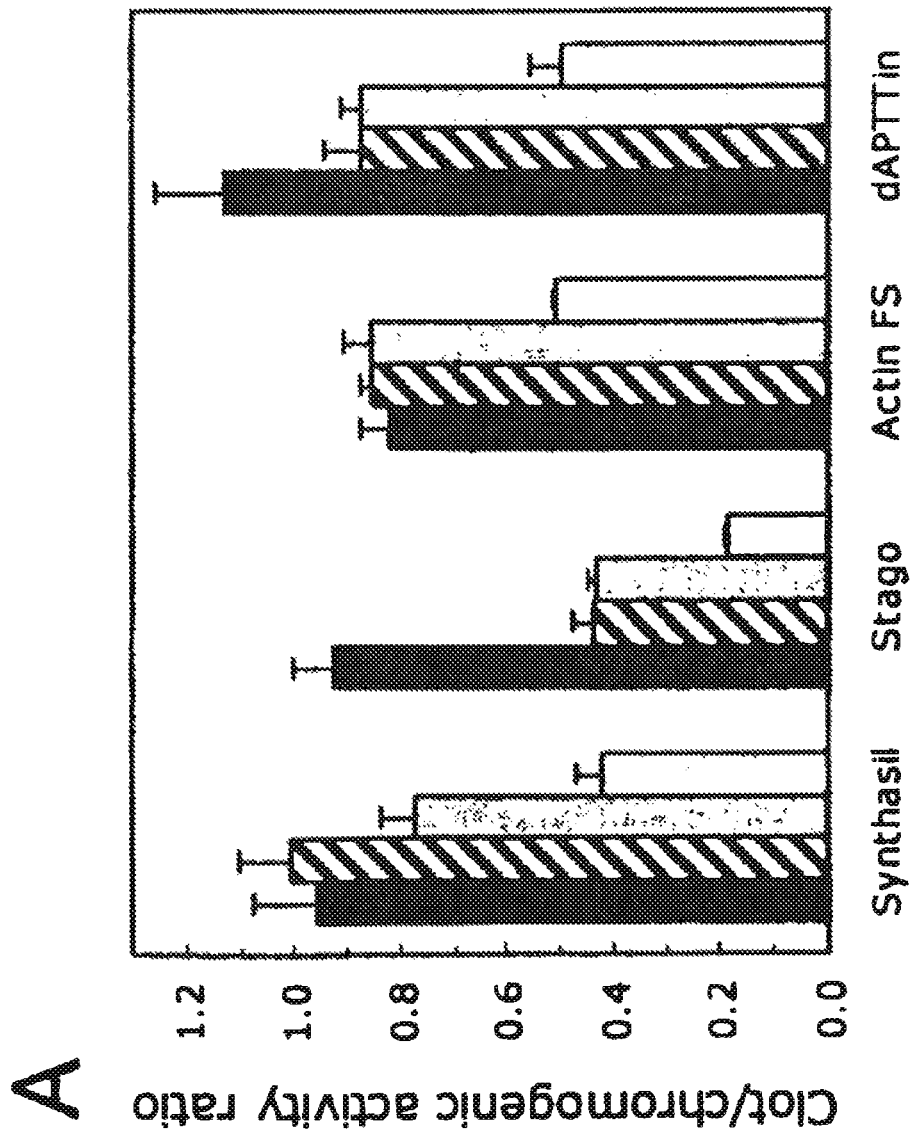
FIG. 4: Clotting activity of O-glycoPEGylated rFVIII using various aPTT reagents. (A) shos the ration between the clotting activity and the chromogenic activity. (B) shows the specific clotting activity.
Figure 4B:
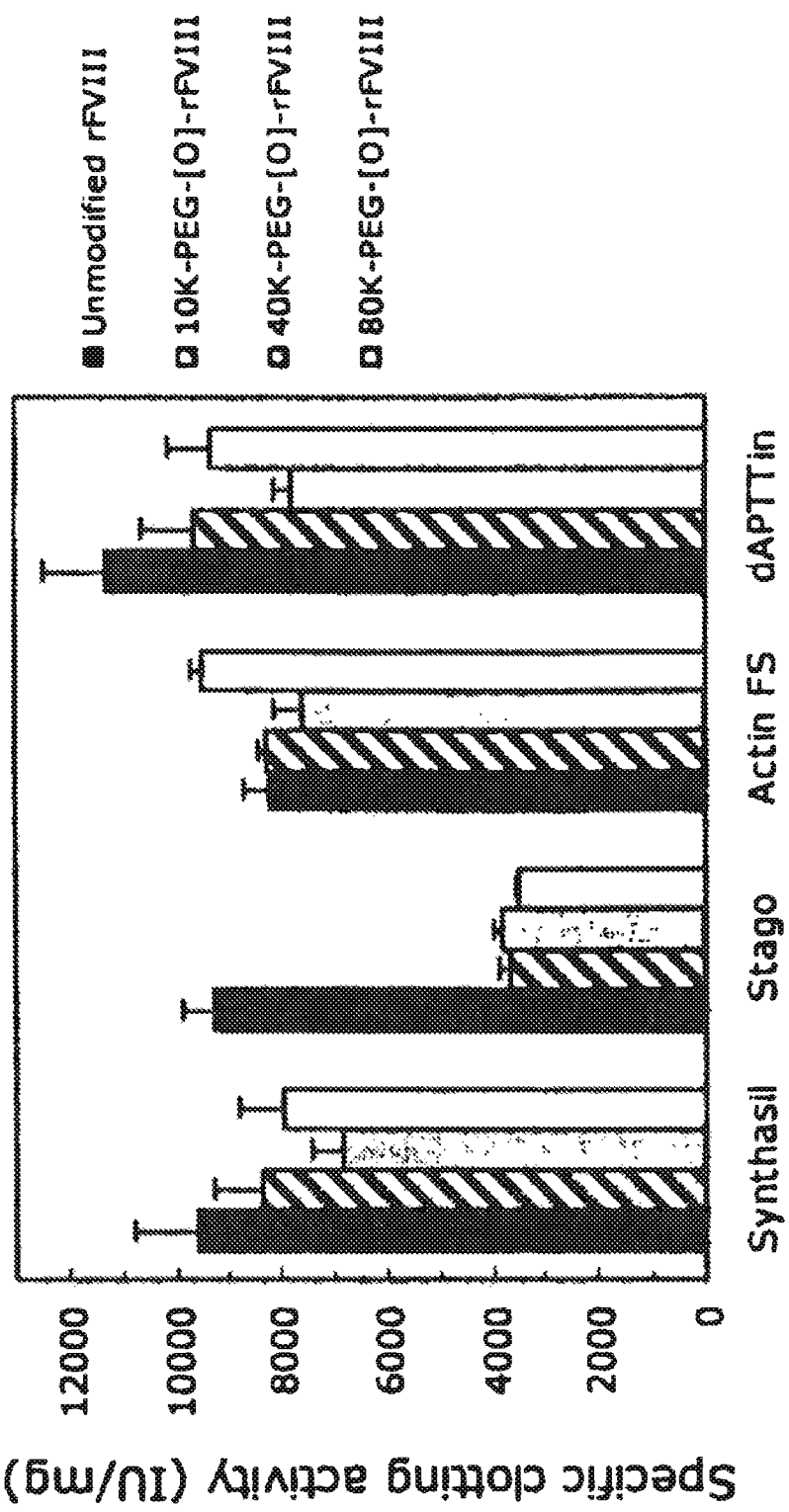
Figure 5:
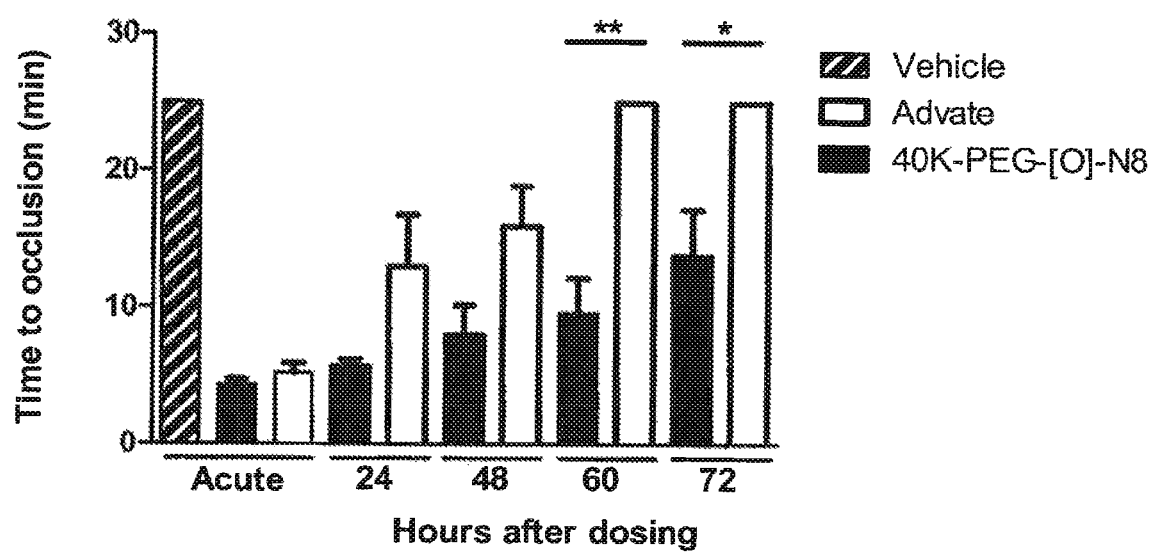
FIG. 5: In vivo effects (time to occlusion) in FVIII KO mice of 40K-PEG-[O]-N8
Figure 6:
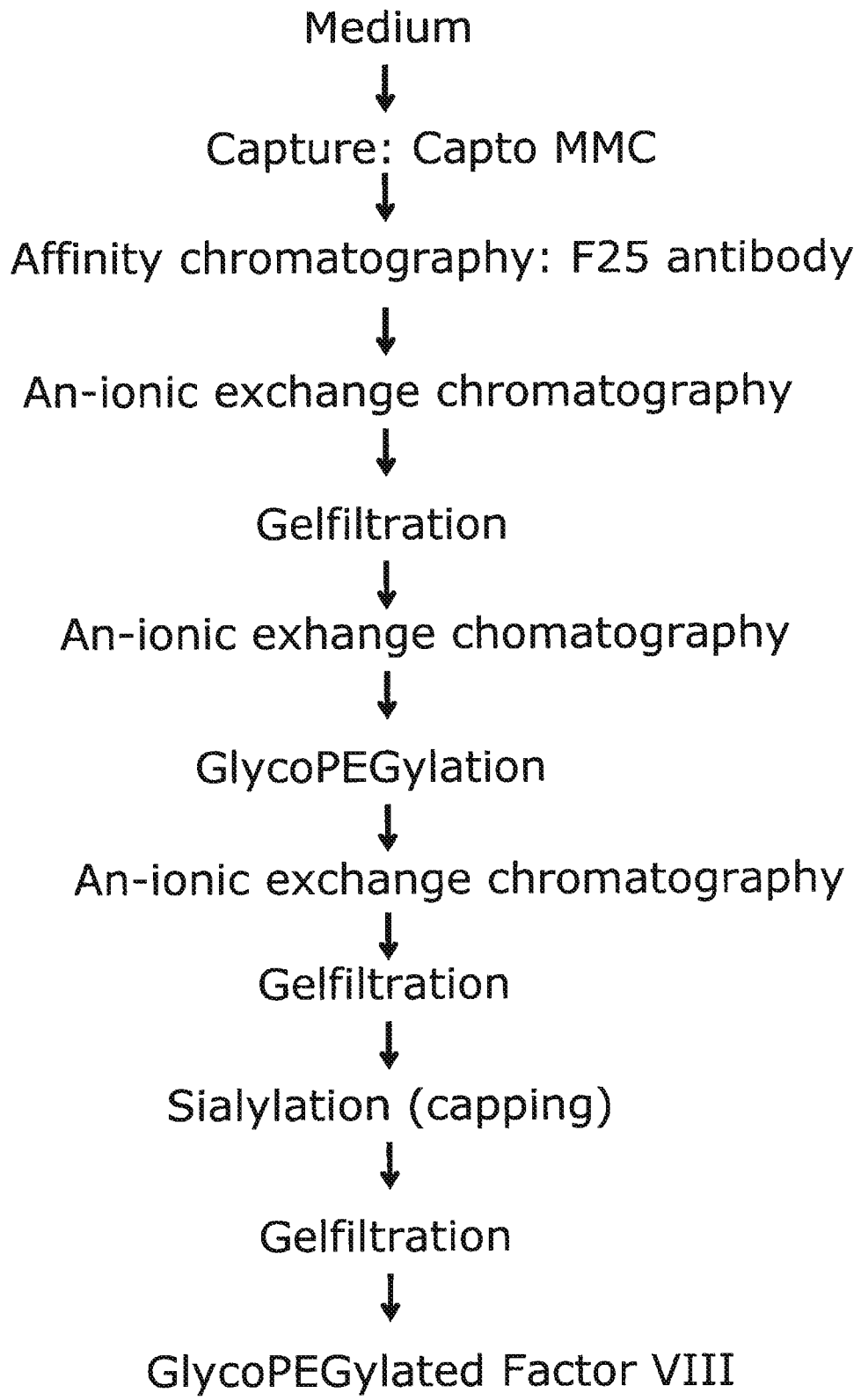
FIG. 6: Flow diagram showing the process steps involved in production of glycoPEGylated Factor FVIII according to the invention.
Figure 7:
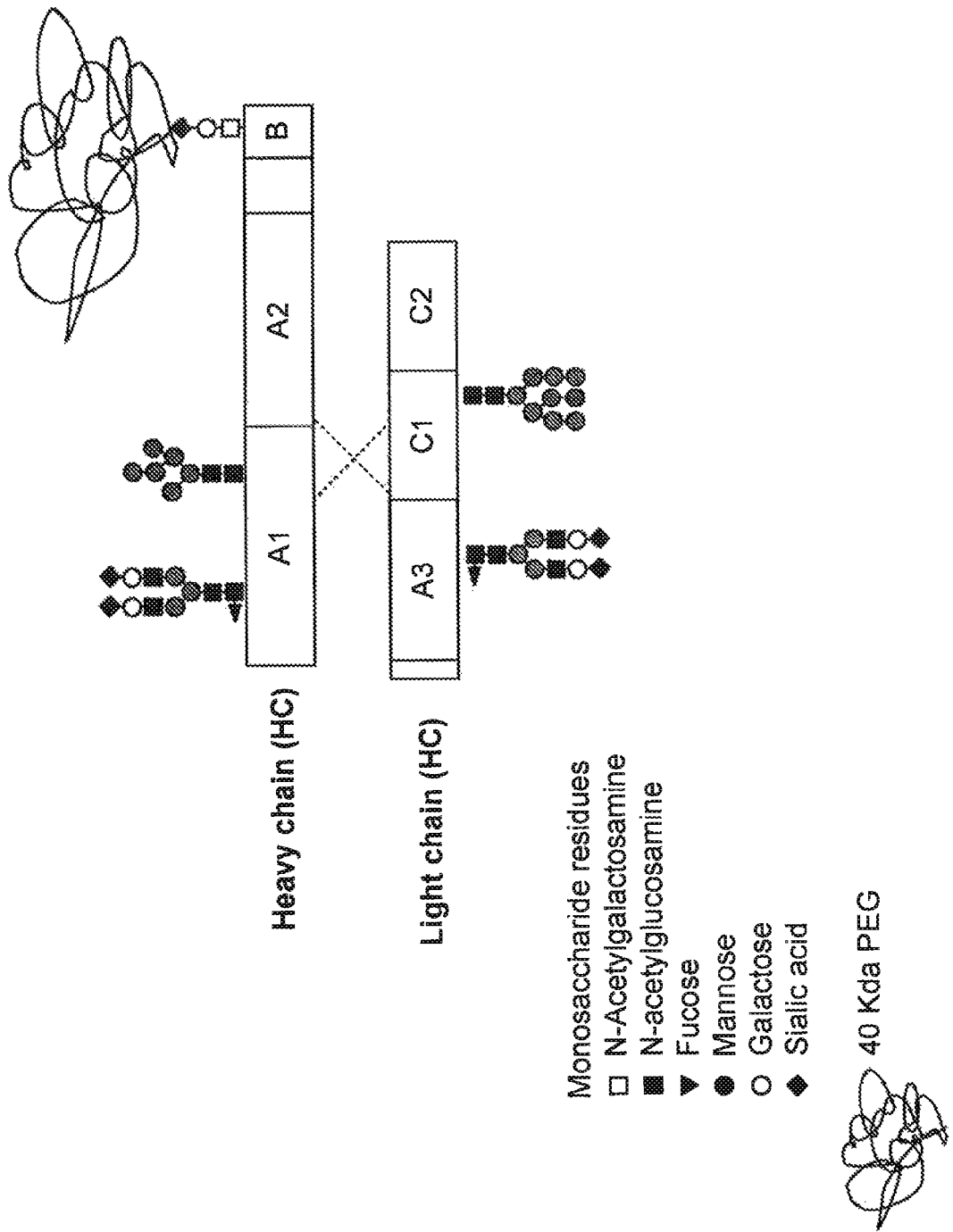
FIG. 7: Schematic representation of a Factor VIII molecule according to the present invention produced in the Examples.
Figure 8:
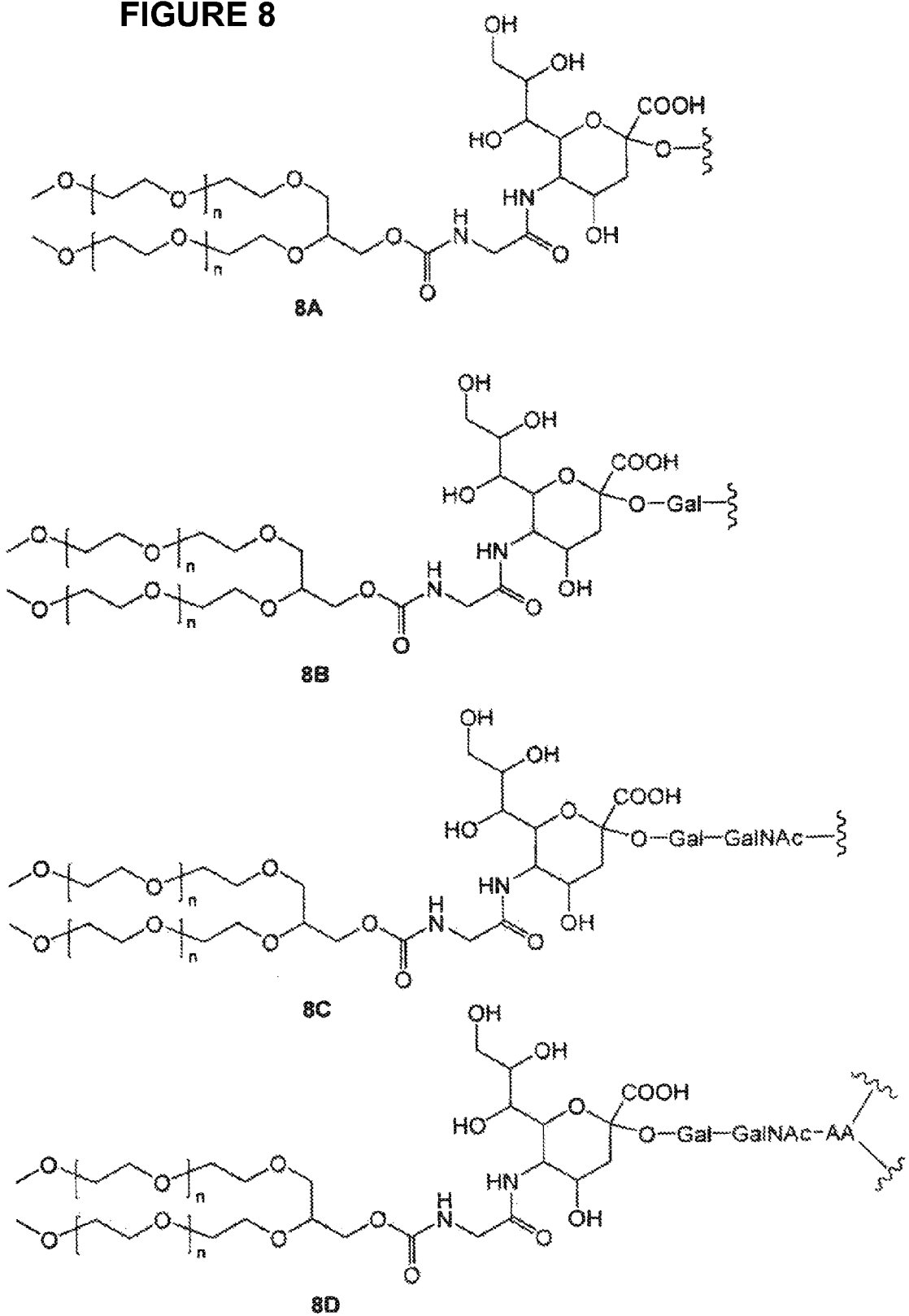
FIG. 8.

FIG. 4 shows clotting activity of O-glycoPEGylated rFVIII using various aPTT reagents. Data are shown as the ratio between the clotting activity and the chromogenic activity (A) or as the specific clotting activity (B). Mean and standard deviations of values from three independent experiments are shown.

TABLE 3

Rate of rFVIII activation and kinetic constants of FX activation by FIXa

| FVIII molecule | Rate of FVIII activation $10^{-3} \times min^{-1}$ | $K_{1/2FIXa}$ nM | FX Activation $K_m$ nM | $k_{cat}$ $s^{-1}$ |
|---|---|---|---|---|
| rFVIII | 10.4 ± 1.9 | 0.88 ± 0.46 | 7.9 ± 1.7 | 4.5 ± 1.9 |
| 40K-PEG-[O]-rFVIII | 9.9 ± 3.8 | 0.42 ± 0.02 | 6.4 ± 0.8 | 4.7 ± 0.2 |
| 80K-PEG-[O]-rFVIII | 9.8 ± 3.4 | 1.11 ± 0.12 | 8.2 ± 0.6 | 3.7 ± 0.4 |

Data are mean and standard deviations of 3-6 measurements.

Example 6

Pharmacokinetics of GlycoPEGylated B-domain Deleted (BDD)-FVIII in FVIII KO Mice and vWF KO Mice The pharmacokinetics of BDD-FVIII glycoPEGylated with various PEG sizes was studied following i.v. administration of 280 IU/kg to FVIII KO mice.

The following compounds were studied: BDD-FVIII, BDD-FVIII-10K PEG (O-glycan, 0129-0000-1005), BDD-FVIII-40K PEG (O-glycan, 0129-0000-1003), BDD-FVIII-2×40K PEG (O and N-glycan 0129-0000-1008-1A), BDD-FVIII-80K PEG (N-glycan, 0129-0000-1012, O-glycan 0129-0000-1009).

Design of Animal Studies:

Factor VIII knock out (FVIII KO) mice were bred at Taconic M&B, based on exon 16 KO in C57Bl/6 background. A mixture of male and female (app.1:1) with an approximate weight of 25 g and age range of 19-26 weeks were employed. The mice were not fully back-crossed. No FVIII is detected in this mouse strain.

The mice were given single i.v. injections of 280 IU/kg in the tail vein with the compounds listed above. If a mouse was dosed peri-veneously, the mouse was exchanged with another mouse. After dosing, orbital plexus blood samples were collected from pre-dose until 64 hours after dosing using non-coated capillary glass tubes. Three samples were taken from each mouse, and 2, 3 or 4 samples were collected at each time point. Blood was stabilised in sodium citrate (9:1) and diluted in FVIII COA SP buffer (1:4) before centrifugation for 5 minutes at 4000 g. Plasma obtained from diluted blood was frozen at dry ice at kept at −80° C. before quantitative analysis by means of FVIII chromogenic activity and/or FVIII antigen analysis.

Quantitative Plasma Analysis:

The FVIII chromogenic activity was determined by the use of reagents from the Coatest SP kit (Chromogenix). Diluted plasma samples, calibrators (ILS calibration plasma) in Coatest SP-buffer, and buffer negative control (50 µl) were added to 96-well microtiter plates (Nunc) in duplicates. The Factor IXa/Factor X reagent, the phospholipid reagent and $CaCl_2$ from the Coatest SP kit were mixed 5:1:3 (vol:vol:vol) and 75 µl of this added to the wells. After 15 min incubation at room temperature 50 µl of the Factor Xa substrate S-2765/thrombin inhibitor I-2581 mix was added and the reactions incubated 10 min at room temperature before 25 µl 2% citric acid was added. The absorbance at 405 nm was measured on a Spectramax microtiter plate reader (Molecular Devices). FVIII activity in the plasma samples was calculated from the calibration curve made by dilutions of the calibrated international plasma standard (ILS).

The FVIII antigen assay was a commercial available ELISA kit from Diagnostica Stago (Asserachrom VIII:CAg) using two monoclonal antibodies directed against the light chain of human FVIII. Calibrators (dilutions of the compounds) or plasma samples were diluted at least 50-fold in coatest SP dilution buffer supplied by the kit were applied to the precoated wells and the ELISA performed according to the manufactures instructions. The values used for reporting the pharmacokinetic study are based on the standard curve made from the compounds themselves.

Pharmacokinetic Parameters Estimations:

Pharmacokinetic analysis was carried out by non-compartmental methods (NCA) of data using ILS as calibrator (data based on chromogenic activity), using the compounds themselves as calibrator (data based on ELISA). From the data the following parameters were estimated: Cmax (maximum concentration, after i.v. administration this is at the first sampling time point), Tmax (time of maximum concentration, after i.v. administration this is the first time point), AUC0-∞ (area under the curve from time 0 to infinity), T½, (terminal half-live), CL (clearance) and Vss (volume of distribution at steady state). All calculations were performed using WinNonlin Pro version 4.1.

After i.v. injection of 280 IU/Kg BDD-FVIII, BDD-FVIII-10 KDa PEG, BDD-FVIII-40 KDa PEG, BDD-FVIII-2×40 KDa PEG and BDD-FVIII-80 KDa PEG to FVIII KO mice, the half-life increased along with increasing PEG size in the range of 7.8 h (BDD-FVIII) to 15-16 h (Table 4), which corresponds to a 2-fold increase. Similarly, the clearance was reduced and the MRT increased with increasing PEG sizes (Table 4).

TABLE 4

Pharmacokinetic parameters estimates of FVIII glycoPEGylated with different sizes of PEG after i.v. administration to FVIII KO mice based on chromogenic activity (BDD: B-domain deleted).

| Compound | Dose (IU/kg) | T½ (h) | CL (ml/h/kg) | MRT (h) | Prolongation (fold) |
|---|---|---|---|---|---|
| BDD-FVIII | 280 | 6.7-9.3 | 8.1-10 | 9.9-11 | 1 |
| BDD-FVIII 10 KDa PEG (O-glycan) | 280 | 10 | 8.5 | 16 | 1.3 |
| BDD-FVIII-2x40 KDa PEG | 280 | 13 | 5.8 | 19 | 1.9-2.1 |
| BDD-FVIII 40 KDa PEG (O-glycan) | 280 | 15-16 | 3.6-3.8 | 20-22 | 1.7 |
| BDD-FVIII 80 KDa PEG (O-glycan) | 280 | 15 | 6.4 | 21 | 1.9 |

Conclusion:

GlycoPEGylation of BDD-FVIII increased the T1/2 1.3-2.1 fold as compared to BDD-FVIII after i.v. administration of 280 IU/kg to FVIII KO mice. An increasing T1/2 was observed as the size of the PEG group was increased in the range of 10 KDa to 80 KDa PEG.

Example 7

Prolonged Haemostatic Effect of 40K-PEG-[O]-N8 Compared to Advate in a $FeCl_3$ Induced Injury Model in Haemophilia A Mice The duration of action of 40K-PEG-[O]-N8 vs. recombinant FVIII (Advate) was investigated in a FeCl3 induced injury model in haemophilia A (F8-KO) mice.

Mice were anesthetized and placed on a heating pad (37° C.) to maintain body temperature. The carotid artery was exposed and a flow-probe (0.5PSB Nanoprobe) that measures blood flow by ultrasound was placed around the artery. The injury (an iron-mediated chemical oxidation) was induced by applying a filter paper (2×5 mm) briefly soaked in a 10% FeCl3 solution around the exposed carotid artery. The filter paper was removed after 3 min. The artery was then washed three times with 0.9% NaCl and finally Surgilube (an acoustic coupler) was applied in order to displace air in the flow-probe and secure an optimised measurement of the blood flow. Blood flow (ml/min) was recorded for 25 min after removing the FeCl3 saturated filter paper and the time to occlusion was determined by measuring the time (in min) from removal of FeCl3 saturated filter paper until the blood flow was 0 ml/min. If occlusion did not occur after 25 min the occlusion time was reported as 25 min even though no occlusion occurred during the observation period. F8-KO mice (n=6-10) were treated with Advate (280 U/kg), 40K-PEG-[O]-N8 (280 U/kg), or vehicle. The FeCl3 induced injury was made 5 min (acute effect) or 24, 48, 60, and 72 hours after dosing. The blood flow (ml/min) was recorded for 25 min after removal of FeCl3, and subsequently the time to occlusion was determined.

No occlusion occurred in vehicle treated F8-KO mice, whereas occlusion occurred in all mice treated with 40 KDa-PEG-[O]-N8 and Advate 5 min after dosing (acute effect) with a mean occlusion time of 4.3±0.4 min and 5.2±0.7 min, respectively. In 40 KDa-PEG-[O]-N8 treated F8-KO mice the average occlusion time increased to 13.8±3.4 min at 72 hours after dosing. In contrast the Advate treated F8-KO mice had an occlusion time of 13.0±3.4 min and 15.9±2.9 min after 24 and 48 hours, respectively. Importantly no occlusions were observed 60 and 72 hours after administration of Advate. In all mice treated with 40 KDa-PEG-[O]-N8 occlusion was observed 24 hours after dosing whereas only 67% of the mice treated with Advate occluded. After 72 hours occlusion was still seen in 63% of the mice treated with 40 KDa-PEG-[O]-N8, whereas no occlusion was observed 60 and 72 hours after administration of Advate.

Prolonged Effect of 40 KDa-PEG-[O]-N8 in F8-KO Mice.

The FeCl3 induced injury was made 5 min (acute effect), 24, 48, 60, and 72 hours after dosing 280 IU/kg 40 KDa-PEG-[O]-N8, 280 IU/kg Advate, or vehicle. The blood flow (mL/min) was recorded for 25 min after removal of FeCl3, and subsequently the time to occlusion was determined. At 60 and 72 hours after dosing no occlusion occurred in mice dosed with Advate. Mean and SEM of 6-10 mice per group are shown. Time to occlusion between the different groups was compared using Kruskal-Wallis test including Dunn's post test. *: $p<0.05$; **: $p<0.01$.

In conclusion, the haemostatic effect of 40 KDa-PEG-[O]-N8 is significantly prolonged compared to Advate in a FeCl3 induced injury model in F8-KO mice.

What is claimed:

1. A B-domain truncated Factor VIII (FVIII) molecule, comprising: a heavy chain, a light chain, and a hydrophilic polymer; wherein (1) the heavy chain comprises a linker derived from the B-domain of a full-length FVIII molecule (SEQ ID NO:1) comprising a protease recognition site, (2) the hydrophilic polymer is covalently conjugated to the linker at Ser750 amino acid residue numbered relative to SEQ ID NO:1 via an O-linked oligosaccharide, (3) the length of the linker is 20-30 amino acids, and (4) activation of the molecule by thrombin results in removal of the linker and the hydrophilic polymer; wherein the B-domain truncated FVIII molecule has an increased circulatory half-life compared to a wild-type FVIII molecule.

2. The molecule according to claim 1, wherein the hydrophilic polymer is polyethylene glycol (PEG).

3. The molecule according to claim 2, wherein the size of the PEG is in a range of 10,000 to 160,000 Da.

4. The molecule according to claim 3, wherein the size of the PEG is 40,000 Da.

5. The molecule according to claim 1, wherein the hydrophilic polymer is a polysaccharide.

6. The molecule according to claim 5, wherein the polysaccharide is polysialic acid.

7. A pharmaceutical composition comprising a molecule according to claim 1.

8. A method of making a molecule according to claim 1, wherein said method comprises conjugating a B-domain truncated Factor VIII molecule with a hydrophilic polymer via an O-linked oligosaccharide in the truncated B domain.

9. A molecule obtained by a method according to claim 8.

10. A method of treating hemophilia comprising administering to a patient in need of such treatment a molecule according to claim 1.

11. A method according to claim 10, wherein said molecule is administered subcutaneously.

12. A method according to claim 10, wherein said molecule is administered intravenously.

* * * * *